(12) United States Patent
Chiorini

(10) Patent No.: US 9,833,519 B2
(45) Date of Patent: Dec. 5, 2017

(54) METHODS FOR THE DIAGNOSIS AND TREATMENT OF SJÖGREN'S SYNDROME

(71) Applicant: The United States of America, as represented by the Secretary, Department of Health and Human Services, Washington, DC (US)

(72) Inventor: John A. Chiorini, Dayton, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/428,929

(22) PCT Filed: Sep. 25, 2013

(86) PCT No.: PCT/US2013/061587
§ 371 (c)(1),
(2) Date: Mar. 17, 2015

(87) PCT Pub. No.: WO2014/052393
PCT Pub. Date: Apr. 3, 2014

(65) Prior Publication Data
US 2015/0273083 A1 Oct. 1, 2015

Related U.S. Application Data

(60) Provisional application No. 61/705,517, filed on Sep. 25, 2012.

(51) Int. Cl.
| | |
|---|---|
| *A61K 31/519* | (2006.01) |
| *A61K 49/00* | (2006.01) |
| *G01N 33/68* | (2006.01) |
| *A61K 38/17* | (2006.01) |
| *C07K 16/22* | (2006.01) |
| *C12N 15/113* | (2010.01) |
| *C12N 15/115* | (2010.01) |
| *C12Q 1/68* | (2006.01) |
| *G01N 33/74* | (2006.01) |

(52) U.S. Cl.
CPC ........ *A61K 49/0004* (2013.01); *A61K 31/519* (2013.01); *A61K 38/177* (2013.01); *A61K 38/179* (2013.01); *C07K 16/22* (2013.01); *C12N 15/115* (2013.01); *C12N 15/1136* (2013.01); *C12Q 1/6883* (2013.01); *G01N 33/6872* (2013.01); *G01N 33/6893* (2013.01); *G01N 33/74* (2013.01); *C07K 2317/622* (2013.01); *C07K 2317/76* (2013.01); *C12N 2320/30* (2013.01); *G01N 2333/4704* (2013.01); *G01N 2333/51* (2013.01); *G01N 2800/101* (2013.01)

(58) Field of Classification Search
CPC .............. A61K 49/0004; A61K 31/519; A61K 38/177; A61K 38/179; C07K 16/22; C07K 2317/622; C07K 2317/76; C12N 15/1136; C12N 15/115; C12N 2320/30; C12Q 1/6883; G01N 33/6872; G01N 33/6893; G01N 33/74; G01N 2333/4704; G01N 2333/51
See application file for complete search history.

(56) References Cited

U.S. PATENT DOCUMENTS

| | | |
|---|---|---|
| 7,477,947 B2 | 1/2009 | Pines et al. |
| 2004/0253652 A1 | 12/2004 | Davies |
| 2007/0170928 A1 | 7/2007 | Fedan et al. |
| 2009/0024678 A1 | 1/2009 | Milby et al. |
| 2010/0322948 A1 | 12/2010 | Mueller et al. |
| 2011/0046509 A1 | 2/2011 | Uematsu et al. |

FOREIGN PATENT DOCUMENTS

| | | |
|---|---|---|
| WO | WO 2006/105359 | 10/2006 |
| WO | WO 2011/079307 | 6/2011 |

OTHER PUBLICATIONS

Vaiman et al (otolaryngology and neck Surgery (2005) vol. 133, pp. 869-873.*
Heikinheimo (Cancer Research (1999) vol. 59, pp. 5815-5821) (IDS Mar. 17, 2015).*
Deligezer (Clinica Chimica Acta (2010) vol. 411, pp. 1452-1456).*
Cheung et al (Nature Genetics, 2003, vol. 33, pp. 422-425).*
Saito-Hisaminato et al. (DNA research (2002) vol. 9, pp. 35-45).*
Benner et al (Trends in Genetics (2001) vol. 17, pp. 414-418).*
Petersen (Electrophysiology of Salivary and Pancreatic acinar cells (Handbook of Physiology- Gastrointestinal System III(1989) pp. 25-50).*
Kusafuka (Pathology international (1999) vol. 49, pp. 1023-1027).*
May et al (Science (1988) vol. 241, p. 1441).*
Aoki et al., "Synergistic Effects of Different bone Morphogenetic Protein Type I Receptors on Alkaline Phosphatase Induction," *J. Cell Sci.*, vol. 114:1483-1489, 2001.

(Continued)

*Primary Examiner* — Steven Pohnert
(74) *Attorney, Agent, or Firm* — Klarquist Sparkman, LLP

(57) ABSTRACT

Described herein is the finding that patients with Sjögren's syndrome exhibit a statistically significant increase in expression of BMP6 in the salivary gland, relative to healthy control subjects. Also described herein is the finding that overexpression of BMP6 in the salivary glands of mice results in an increase in electrical potential across the salivary gland. Thus, provided herein are methods of diagnosing a subject as having Sjögren's syndrome, or at risk for developing Sjögren's syndrome, by measuring the level of BMP6 expression in a salivary gland of a subject, measuring electrical potential in a salivary gland of a subject, or both. Also provided herein are methods of treating a subject with Sjögren's syndrome by administering an agent that inhibits expression of BMP6 expression or activity. Also described herein is the use of XIST and MECP2 as diagnostic and therapeutic targets for male Sjögren's syndrome patients.

14 Claims, 23 Drawing Sheets

(56) References Cited

OTHER PUBLICATIONS

Ara et al., "Bone Morphogenetic Proteins 4, 6, and 7 are Up-Regulated in Mouse Spinal Cord during Experimental Autoimmune Encephalomyelitis," *J. Neurosci. Res.*, vol. 86:125-135, 2008.

Baker et al., "Proinflammatory cytokines tumor necrosis factor-α and interferon-γ alter tight junction structure and function in rat parotid gland ParC10 cell line," *Am J Physiol Cell Physiol* vol. 295:C1191-C121, 2008.

Beal, "Salivary Electrolyte Concentrations and Electrical Potential Difference across the Parotid Salivary Duct of Anaesthetized Sodium-replete Sheep," *Aust J Biol Sci* vol. 33:197-204, 1980.

Blessing et al., "Overexpression of Bone Morphogenetic Protein-6 (BMP-6) in the Epidermis of Transgenic Mice: Inhibition or Stimulation of Proliferation Depending on the Pattern of Transgene Expression and Formation of Psoriatic Lesions," *J Cell Biol* vol. 135(1):227-239, 1996.

Clarke et al., "Protein kinase C activation leads to dephosphorylation of occluding and tight junction permeability increase in LLC-PK1 epithelial cell sheets," *J Cell Sci* vol. 113:3187-3196, 2000.

Cobb et al., "Genetic Association between methyl-CpG-binding Protein 2 (MECP2) and Primary Sjögren's Syndrome," *Ann Rheum Dis*, vol. 69:1731-1732, 2010.

De Angelis et al., "Chimeric snRNA Molecules Carrying Antisense Sequences against the Splice Junctions of Exon 51 of the Dystrophin Pre-mRNA Induce Exon Skipping and Restoration of a Dystrophin Synthesis in 448-50 DMD Cells," *Proc. Natl. Acad. Sci. USA*, vol. 99:9456-9461, 2002.

Devauchelle-Pensec et al., "Gene Expression Profile in the Salivary Glands of Primary Sjögren's Syndrome Patients Before and After Treatment with Rituximab," *Arthritis Rheum.*, vol. 62:2262-2271, 2010.

Duperrex et al., "A new device for in vivo measurement of nasal transepithelial potential difference in cystic fibrosis patients and normal subjects," *Eur Respir J* vol. 10:1631-1636, 1997.

Ebisawa et al., "Characterization of Bone Morphogenetic Protein-6 Signaling Pathways in Osteoblast Differentiation," *J. Cell Sci.*, vol. 112:3519-3527, 1999.

Ewert et al., "Disruption and Tight Junction Structure in Salivary Glands From Sjögren's Syndrome Patients Is Linked to Proinflammatory Cytokine Exposure," *Arthritis Rheum* vol. 62(5):1280-1289, 2010.

Ferrell et al., "A Microfluidic Bioreactor With Integrated Transepithelial Electrical Resistance (TEER) Measurement Electrodes for Evaluation of Renal Epithelial Cells," *Biotechnol Bioeng* vol. 107:707-716, 2010.

Goyenvalle et al., "Enhanced Exon-Skipping Induced by U7 snRNA Carrying a Splicing Silencer Sequence: Promising Tool for DMD Therapy," *Mol. Therapy*, vol. 17:1234-1240, 2009.

Hayashi et al., "Dysfunction of Lacrimal and Salivary Glands in Sjögren's Syndrome: Nonimmunologic Injury in Preinflammatory Phase and Mouse Model," *J Biomed Biotechnol*, vol. 2011, Article ID 407031, 15 pp., Epub Jun. 1, 2011.

Heikinheimo et al., "Bone Morphogenetic Protein-6 is a Marker of Serous Acinar Cell Differentiation in Normal and Neoplastic Human Salivary Gland," *Cancer Res* vol. 59:5815-5821, 1999.

Henricsson et al., "Evaluation of some electrical methods for objective assessment of oral mucosal dryness," *Scand J Dent Res* vol. 98(6):5200-528, 1990 (abstract only).

Hjelmervik et al., "Gene Expression Profiling of Minor Salivary Glands Clearly Distinguishes Primary Sjogren's Syndrome Patients from Healthy Control Subjects," *Arthritis Rheum.*, vol. 52:1534-1544, 2005.

Kainuma et al., "Identification of Differentially Expressed Genes in Salivary Gland Tumors with cDNA Microarray," *Auris Nasus Larynx*, vol. 31:261-268, 2004.

Kersten et al., "Bmp-6 Inhibits Growth of Mature Human B Cells; Induction of Smad Phosphorylation and Upregulation of Id I," *BMC Immunol*, vol. 6:1471-2172, 2005.

Kusafuka et al., "Immunohistochemical Evaluation of Cartilage-Derived Morphogenic Protein-1 and -2 in Normal Human Salivary Glands and Pleomorphic Adenomas," *Virchows Arch.*, vol. 442:482-490, 2003.

List et al., "Epithelial Integrity is Maintained by a Matriptase-Dependent Proteolytic Pathway," *Am. J. Pathol.*, vol. 175:1453-1463, 2009.

Lories et al., "Bone Morphogenetic Proteins 2 and 6, Expressed in Arthritic Synovium, are Regulated by Proinflammatory Cytokines and Differentially Modulate Fibroblast-Like Synoviocyte Apoptosis," *Arthritis Rheum.*, vol. 48:2807-2818, 2003.

Madocsai et al., "Correction of SMN2 Pre-mRNA Splicing by Antisense U7 Small Nuclear RNAs," *Mol. Therapy*, vol. 12:1013-1022, 2005.

Maria et al., "Distribution of Tight Junction Proteins in Adult Human Salivary Glands," *J Histochem Cytochem* vol. 56:1093-1098, 2008.

Micflikier et al., "Potential difference of the pancreatobiliary mucosa during endoscopic retrograde cholangiopancreatography," *CMA J* vol. 122:798-799, 1980.

Rosendahl et al., "Activation of Bone Morphogenetic Protein/Smad Signaling in Bronchial Epithelial Cells during Airway Inflammation," *Am. J. Respir. Cell Mol. Biol.*, vol. 27:160-169, 2002.

Schneyer and Schneyer, "Membrane potentials of salivary gland cells of rat," *Am J Physiol* vol. 209(6):1304-1310, 1965.

Sobakin and Makhnev, "Electrical Potentials of the Parotid Salivary Gland Recorded from the Body Surface in Cats," *Bull Exp Biol Med* vol. 86(6):1563-1565, 1978.

Tamaoki et al., "Cholinergic control of rabbit tracheal transepithelial potential difference in vivo," *Eur Respir J* vol. 9:1632-1636, 1996.

Wang et al., "The Bone Morphogenetic Protein-Hepcidin Axis as a Therapeutic Target in Inflammatory Bowel Disease," *Inflamm Bowel Dis.*, vol. 18:112-119, 2012.

Wegener et al., "Automated multi-well device to measure transepithelial electrical resistances under physiological conditions," *BioTechniques* vol. 37:590-597, 2004.

Hao et al., "In Vivo Structure-Activity Relationship Study of Dorsomorphin Analogues Identifies Selective VEGF and BMP Inhibitors," *ACS Chem Biol.* 5:245-253, 2010.

Mohedas et al., "Development of an ALK2-Biased BMP Type I Receptor Kinase Inhibitor," *ACS Chem Biol.* 8:1291-1302, 2013.

* cited by examiner

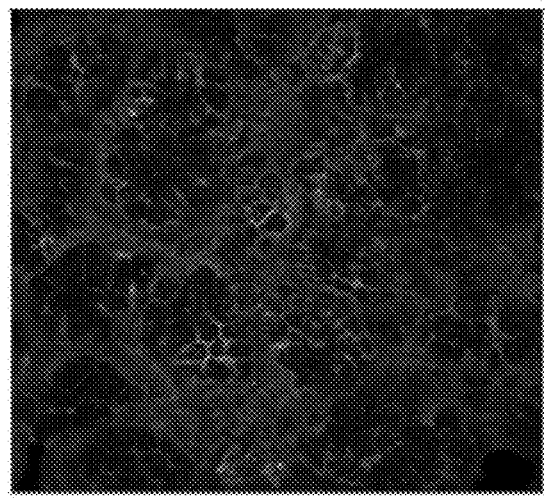
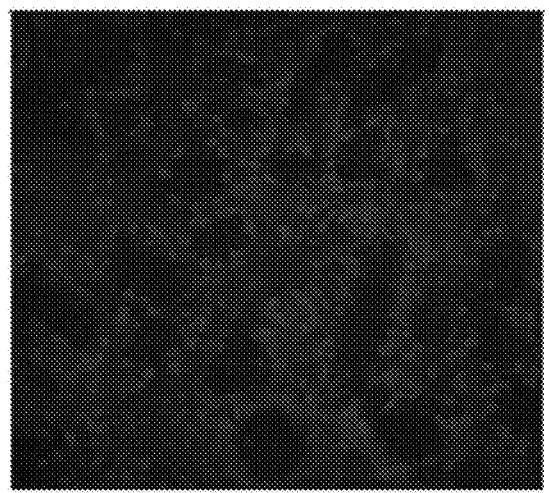
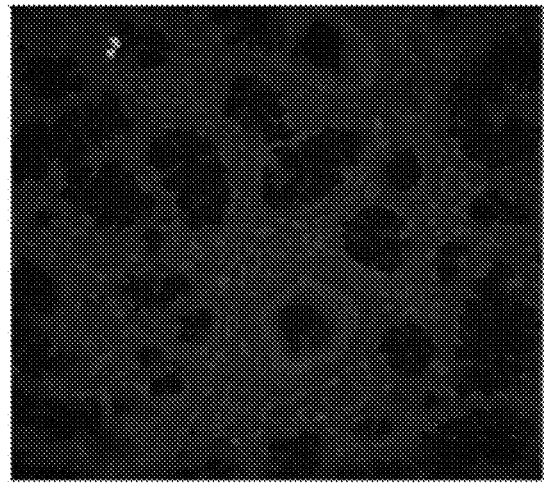
FIG. 2A

* p=0.0046 at day 15, p=0.18 at day 30, p=0.0257 at day 45 and p=0.0077 at day 60, Mann-Whitney-U

FIG. 9

Cytokine production in serum and salivary gland

| | | mIFNg | mIL10 | mIL1b | mIL4 | mTNFa | mIL13 | mIL5 | mIL6 | mKC | mJE | | mMCP5 |
|---|---|---|---|---|---|---|---|---|---|---|---|---|---|
| SG protein | GFP | 110.30 | 60.29 | 87.28 | 16.72 | 30.88 | 4.96 | 11.60 | 10.33 | | 65.52 | | 29.01 | 48.28 |
| | BMP-6 | 61.17 | 40.70 | 90.12 | 8.59 | 17.50 | 4.81 | 0.94 | 21.32 | | 38.49 | | 37.62 | 60.48 |
| | Changing | | | | | | ↓ | | | | | | | |
| | T test | 0.43 | 0.26 | 0.77 | 0.06 | 0.25 | 0.97 | 0.15 | 0.60 | | 0.33 | | 0.39 | 0.54 |
| Serum | GFP | n/a | n/a | n/a | n/a | n/a | n/a | n/a | n/a | n/a | | | 29.63 | 26.20 |
| | BMP-6 | n/a | n/a | n/a | n/a | n/a | n/a | n/a | n/a | n/a | | | 50.21 | 17.96 |
| | Changing | n/a | n/a | n/a | n/a | n/a | n/a | n/a | n/a | n/a | | | | |
| | T-test | n/a | n/a | n/a | n/a | n/a | n/a | n/a | n/a | n/a | | | 0.25 | 0.62 |

| | | mMIP1b | mMMP9 | mIL12p70 | mIL17 | mIL18 | mIL2 | mIL12p40 | mIL23 | | mLSelectin | mRANTES | mTGFb1 |
|---|---|---|---|---|---|---|---|---|---|---|---|---|---|
| SG protein | GFP | 31.39 | 2149.29 | 8.60 | 5.64 | 117.68 | 19.91 | 1.10 | 1909.78 | | 16753.17 | 125.69 | 1202.59 |
| | BMP-6 | 49.24 | 943.62 | 6.98 | 6.82 | 91.74 | 14.67 | 1.92 | 1276.68 | | 18326.00 | 174.15 | 1096.96 |
| | Changing | | ↓ | | | | | | | | | | |
| | T-test | 0.17 | 0.25 | 0.56 | 0.70 | 0.25 | 0.39 | 0.18 | 0.61 | | 0.77 | 0.42 | 0.81 |
| Serum | GFP | 30.61 | 52672.12 | n/a | n/a | 107.09 | | 3.05 | 39.82 | | 1408097.99 | 8.36 | 342534.04 |
| | BMP-6 | 40.58 | 49284.61 | n/a | n/a | 166.30 | | 3.39 | 147.67 | | 1358330.97 | 9.22 | 348898.51 |
| | Changing | | | n/a | | ↑ | | -0.11 ↑ | | | ↓ | | |
| | T-test | 0.12 | 0.84 | | | 0.47 | | 0.88 | 0.54 | | 0.83 | | 0.94 |

↑/↓: increase / decrease of mean of BMP-6 group is more than 50%.

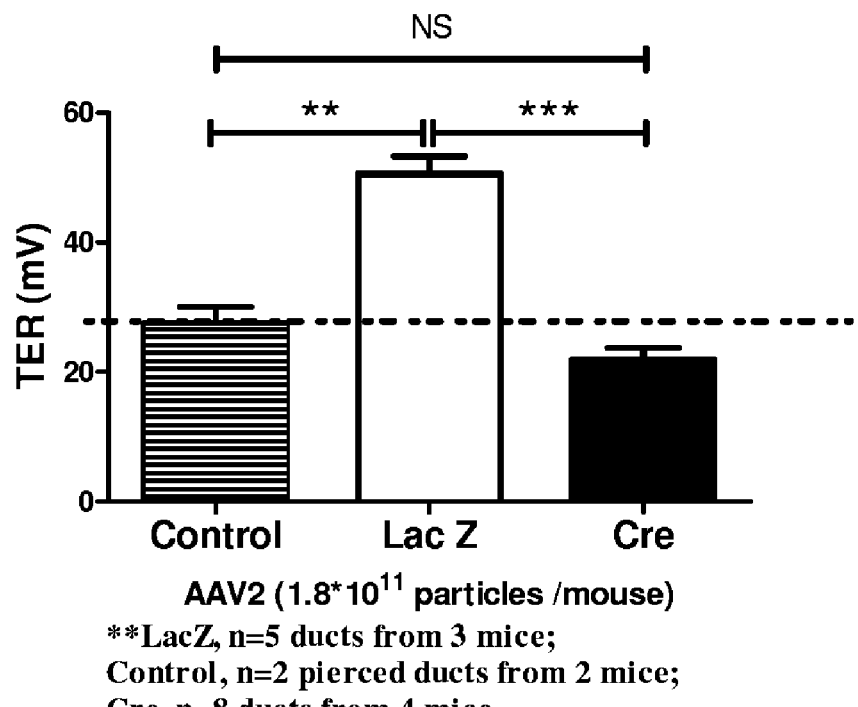
**LacZ, n=5 ducts from 3 mice;
Control, n=2 pierced ducts from 2 mice;
Cre, n=8 ducts from 4 mice
FIG. 11B
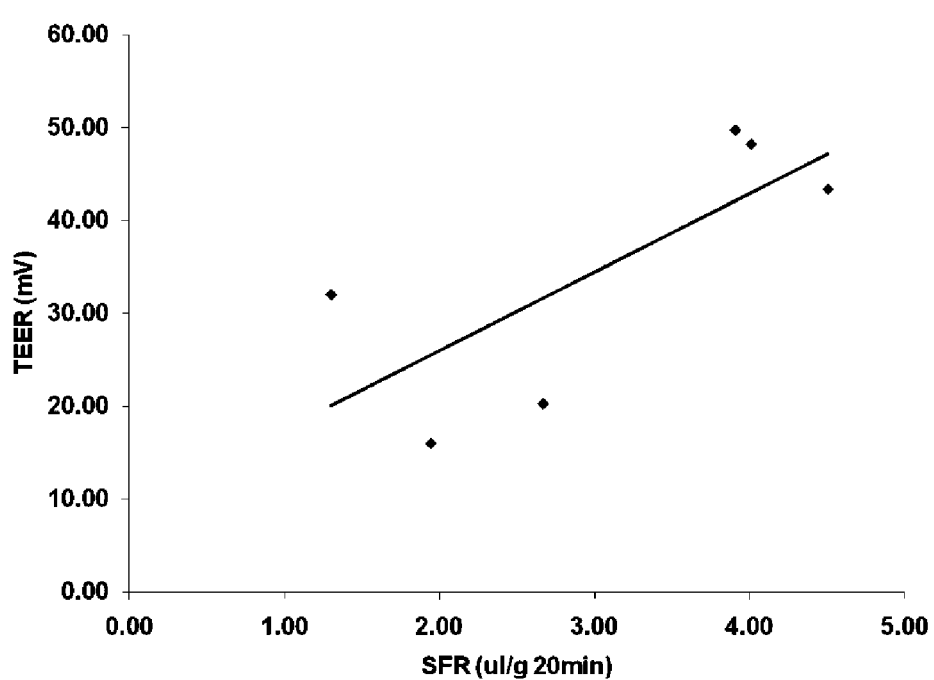

Sup fig 2.

FIG. 16 Comparative Genomic Hybridization to detect copy number variance (CNV)

Deletions

| Nearest Gene | Chromosome Position | #Unchanged pSS | #Unchanged Control | #Del pSS | #Del Control | Fisher's 3x2 Exact Test p value |
|---|---|---|---|---|---|---|
| OPN1MW2 (+) | chrX:153111311-153148420 | 7 | 10 | 6 | 1 | 0.0498 |
| TEX28 (-) | chrX:153148420-153163206 | 8 | 11 | 6 | 1 | 0.0392 |
| TMLHE (-) | chrX:154447033-154453742 | 2 | 12 | 13 | 5 | 0.0016 |

14 PSS / 15 CTRL

No whole chromosome duplication in majority of Male pSS tested
Regional CNV detected in X-chromosome
  No change to XIST copy number
  No change to XIC area copy number CNV detected covering OPN1LW-TEX28
  Upstream from MECP2
  Opsin (CNV associated with color vision dysfunction)
  Triplicate Opsin genes

SEQUENCE LISTING

```
<160> NUMBER OF SEQ ID NOS: 15

<210> SEQ ID NO 1
<211> LENGTH: 3105
<212> TYPE: DNA
<213> ORGANISM: Homo sapiens
<220> FEATURE:
<221> NAME/KEY: CDS
<222> LOCATION: (179)..(1720)

<400> SEQUENCE: 1
caactggggg cgccccggac gaccatgaga gataaggact gagggccagg aaggggaagc        60
gagcccgccg agaggtggcg gggactgctc acgccaaggg ccacagcggc cgcgctccgg       120
cctcgctccg ccgctccacg cctcgcggga tccgcggggg cagcccggcc gggcgggg        178 atg ccg ggg ctg ggg cgg agg gcg cag tgg ctg tgc tgg tgg tgg ggg        226
Met Pro Gly Leu Gly Arg Arg Ala Gln Trp Leu Cys Trp Trp Trp Gly
1               5                   10                  15 ctg ctg tgc agc tgc tgc ggg ccc ccg ccg ctg cgg ccg ccc ttg ccc        274
Leu Leu Cys Ser Cys Cys Gly Pro Pro Pro Leu Arg Pro Pro Leu Pro
            20                  25                  30 gct gcc gcg gcc gcc gcc gcc ggg ggg cag ctg ctg ggg gac ggc ggg        322
Ala Ala Ala Ala Ala Ala Ala Gly Gly Gln Leu Leu Gly Asp Gly Gly
        35                  40                  45 agc ccc ggc cgc acg gag cag ccg ccg ccg tcg ccg cag tcc tcc tcg        370
Ser Pro Gly Arg Thr Glu Gln Pro Pro Pro Ser Pro Gln Ser Ser Ser
    50                  55                  60 ggc ttc ctg tac cgg cgg ctc aag acg cag gag aag cgg gag atg cag        418
Gly Phe Leu Tyr Arg Arg Leu Lys Thr Gln Glu Lys Arg Glu Met Gln
65                  70                  75                  80 aag gag atc ttg tcg gtg ctg ggg ctc ccg cac cgg ccc cgg ccc ctg        466
Lys Glu Ile Leu Ser Val Leu Gly Leu Pro His Arg Pro Arg Pro Leu
                85                  90                  95 cac ggc ctc caa cag ccg cag ccc ccg gcg ctc cgg cag cag gag gag        514
His Gly Leu Gln Gln Pro Gln Pro Pro Ala Leu Arg Gln Gln Glu Glu
            100                 105                 110 cag cag cag cag cag cag ctg cct cgc gga gag ccc cct ccc ggg cga        562
```

|     |     |     |     |     |     |     |     |     |     |     |     |     |     |      |
|-----|-----|-----|-----|-----|-----|-----|-----|-----|-----|-----|-----|-----|-----|------|
| Gln | Gln | Gln | Gln | Gln | Gln | Leu | Pro | Arg | Gly | Glu | Pro | Pro | Gly | Arg  |
|     |     | 115 |     |     |     |     | 120 |     |     |     | 125 |     |     |      |

```
ctg aag tcc gcg ccc ctc ttc atg ctg gat ctg tac aac gcc ctg tcc      610
Leu Lys Ser Ala Pro Leu Phe Met Leu Asp Leu Tyr Asn Ala Leu Ser
130                 135                 140 gcc gac aac gac gag gac ggg gcg tcg gag ggg gag agg cag cag tcc      658
Ala Asp Asn Asp Glu Asp Gly Ala Ser Glu Gly Glu Arg Gln Gln Ser
145                 150                 155                 160 tgg ccc cac gaa gca gcc agc tcg tcc cag cgt cgg cag ccg ccc ccg      706
Trp Pro His Glu Ala Ala Ser Ser Ser Gln Arg Arg Gln Pro Pro Pro
                165                 170                 175 ggc gcc gcg cac ccg ctc aac cgc aag agc ctt ctg gcc ccc gga tct      754
Gly Ala Ala His Pro Leu Asn Arg Lys Ser Leu Leu Ala Pro Gly Ser
            180                 185                 190 ggc agc ggc ggc gcg tcc cca ctg acc agc gcg cag gac agc gcc ttc      802
Gly Ser Gly Gly Ala Ser Pro Leu Thr Ser Ala Gln Asp Ser Ala Phe
        195                 200                 205 ctc aac gac gcg gac atg gtc atg agc ttt gtg aac ctg gtg gag tac      850
Leu Asn Asp Ala Asp Met Val Met Ser Phe Val Asn Leu Val Glu Tyr
210                 215                 220 gac aag gag ttc tcc cct cgt cag cga cac cac aaa gag ttc aag ttc      898
Asp Lys Glu Phe Ser Pro Arg Gln Arg His His Lys Glu Phe Lys Phe
225                 230                 235                 240 aac tta tcc cag att cct gag ggt gag gtg gtg acg gct gca gaa ttc      946
Asn Leu Ser Gln Ile Pro Glu Gly Glu Val Val Thr Ala Ala Glu Phe
                245                 250                 255 cgc atc tac aag gac tgt gtt atg ggg agt ttt aaa aac caa act ttt      994
Arg Ile Tyr Lys Asp Cys Val Met Gly Ser Phe Lys Asn Gln Thr Phe
            260                 265                 270 ctt atc agc att tat caa gtc tta cag gag cat cag cac aga gac tct     1042
Leu Ile Ser Ile Tyr Gln Val Leu Gln Glu His Gln His Arg Asp Ser
        275                 280                 285 gac ctg ttt ttg ttg gac acc cgt gta gta tgg gcc tca gaa gaa ggc     1090
Asp Leu Phe Leu Leu Asp Thr Arg Val Val Trp Ala Ser Glu Glu Gly
290                 295                 300 tgg ctg gaa ttt gac atc acg gcc act agc aat ctg tgg gtt gtg act     1138
Trp Leu Glu Phe Asp Ile Thr Ala Thr Ser Asn Leu Trp Val Val Thr
305                 310                 315                 320 cca cag cat aac atg ggg ctt cag ctg agc gtg gtg aca agg gat gga     1186
Pro Gln His Asn Met Gly Leu Gln Leu Ser Val Val Thr Arg Asp Gly
                325                 330                 335 gtc cac gtc cac ccc cga gcc gca ggc ctg gtg ggc aga gac ggc cct     1234
Val His Val His Pro Arg Ala Ala Gly Leu Val Gly Arg Asp Gly Pro
            340                 345                 350 tac gac aag cag ccc ttc atg gtg gct ttc ttc aaa gtg agt gag gtg     1282
Tyr Asp Lys Gln Pro Phe Met Val Ala Phe Phe Lys Val Ser Glu Val
        355                 360                 365 cac gtg cgc acc acc agg tca gcc tcc agc cgg cgc cga caa cag agt     1330
His Val Arg Thr Thr Arg Ser Ala Ser Ser Arg Arg Arg Gln Gln Ser
370                 375                 380 cgt aat cgc tct acc cag tcc cag gac gtg gcg cgg gtc tcc agt gct     1378
Arg Asn Arg Ser Thr Gln Ser Gln Asp Val Ala Arg Val Ser Ser Ala
385                 390                 395                 400 tca gat tac aac agc agt gaa ttg aaa aca gcc tgc agg aag cat gag     1426
Ser Asp Tyr Asn Ser Ser Glu Leu Lys Thr Ala Cys Arg Lys His Glu
                405                 410                 415 ctg tat gtg agt ttc caa gac ctg gga tgg cag gac tgg atc att gca     1474
Leu Tyr Val Ser Phe Gln Asp Leu Gly Trp Gln Asp Trp Ile Ile Ala
            420                 425                 430
```

| | | | |
|---|---|---|---|
| ccc aag ggc tat gct gcc aat tac tgt gat gga gaa tgc tcc ttc cca | | | 1522 |
| Pro Lys Gly Tyr Ala Ala Asn Tyr Cys Asp Gly Glu Cys Ser Phe Pro | | | |
| 435 440 445 | | | |
| ctc aac gca cac atg aat gca acc aac cac gcg att gtg cag acc ttg | | | 1570 |
| Leu Asn Ala His Met Asn Ala Thr Asn His Ala Ile Val Gln Thr Leu | | | |
| 450 455 460 | | | |
| gtt cac ctt atg aac ccc gag tat gtc ccc aaa ccg tgc tgt gcg cca | | | 1618 |
| Val His Leu Met Asn Pro Glu Tyr Val Pro Lys Pro Cys Cys Ala Pro | | | |
| 465 470 475 480 | | | |
| act aag cta aat gcc atc tcg gtt ctt tac ttt gat gac aac tcc aat | | | 1666 |
| Thr Lys Leu Asn Ala Ile Ser Val Leu Tyr Phe Asp Asp Asn Ser Asn | | | |
| 485 490 495 | | | |
| gtc att ctg aaa aaa tac agg aat atg gtt gta aga gct tgt gga tgc | | | 1714 |
| Val Ile Leu Lys Lys Tyr Arg Asn Met Val Val Arg Ala Cys Gly Cys | | | |
| 500 505 510 | | | |
| cac taa ctcgaaacca gatgctgggg acacacattc tgccttggat cctagatta | | | 1770 |
| His | | | |
| catctgcctt aaaaaaacac ggaagcacag ttggaggtgg gacgatgaga ctttgaaact | | | 1830 |
| atctcatgcc agtgccttat tacccaggaa gattttaaag gacctcatta ataatttgct | | | 1890 |
| cacttggtaa atgacgtgag tagttgttgg tctgtagcaa gctgagtttg gatgtctgta | | | 1950 |
| gcataaggtc tggtaactgc agaaacataa ccgtgaagct cttcctaccc tcctccccca | | | 2010 |
| aaaacccacc aaaattagtt ttagctgtag atcaagctat ttgggggtgtt tgttagtaaa | | | 2070 |
| tagggaaaat aatctcaaag gagttaaatg tattcttggc taaaggatca gctggttcag | | | 2130 |
| tactgtctat caaaggtaga ttttacagag aacagaaatc ggggaagtgg ggggaacgcc | | | 2190 |
| tctgttcagt tcattcccag aagtccacag gacgcacagc ccaggccaca gccagggctc | | | 2250 |
| cacggggcgc ccttgtctca gtcattgctg ttgtatgttc gtgctggagt tttgttggtg | | | 2310 |
| tgaaaataca cttatttcag ccaaaacata ccatttctac acctcaatcc tccatttgct | | | 2370 |
| gtactctttg ctagtaccaa aagtagactg attacactga ggtgaggcta caaggggtgt | | | 2430 |
| gtaaccgtgt aacacgtgaa ggcaatgctc acctcttctt taccagaacg gttctttgac | | | 2490 |
| cagcacatta acttctggac tgccggctct agtacctttt cagtaaagtg gttctctgcc | | | 2550 |
| tttttactat acagcatacc acgccacagg gttagaacca acgaagaaaa taaaatgagg | | | 2610 |
| gtgcccagct tataagaatg gtgttagggg gatgagcatg ctgtttatga acggaaatca | | | 2670 |
| tgatttccct tgtagaaagt gaggctcaga ttaaatttta gaatattttc taaatgtctt | | | 2730 |
| tttcacaatc atgtactggg aaggcaattt catactaaac tgattaaata atacatttat | | | 2790 |
| aatctacaac tgtttgcact tacagctttt tttgtaaata taaactataa tttattgtct | | | 2850 |
| attttatatc tgttttgctg taacattgaa ggaaagacca gacttttaaa aaaaagagt | | | 2910 |
| ttatttagaa agtatcatag tgtaaacaaa caaattgtac cactttgatt ttcttggaat | | | 2970 |
| acaagactcg tgatgcaaag ctgaagttgt gtgtacaaga ctcttgacag ttgtgcttct | | | 3030 |
| ctaggaggtt gggtttttttt aaaaaagaa ttatctgtga accatacgtg attaataaag | | | 3090 |
| atttccttta aggca | | | 3105 |

<210> SEQ ID NO 2
<211> LENGTH: 513
<212> TYPE: PRT
<213> ORGANISM: Homo sapiens

<400> SEQUENCE: 2

Met Pro Gly Leu Gly Arg Arg Ala Gln Trp Leu Cys Trp Trp Trp Gly
1               5                   10                  15

```
Leu Leu Cys Ser Cys Cys Gly Pro Pro Leu Arg Pro Pro Leu Pro
            20              25              30

Ala Ala Ala Ala Ala Ala Gly Gln Leu Leu Gly Asp Gly Gly
        35              40              45

Ser Pro Gly Arg Thr Glu Gln Pro Pro Ser Pro Gln Ser Ser Ser
 50              55              60

Gly Phe Leu Tyr Arg Arg Leu Lys Thr Gln Glu Lys Arg Glu Met Gln
 65              70              75              80

Lys Glu Ile Leu Ser Val Leu Gly Leu Pro His Arg Pro Arg Pro Leu
                85              90              95

His Gly Leu Gln Gln Pro Gln Pro Ala Leu Arg Gln Glu Glu
            100             105             110

Gln Gln Gln Gln Gln Gln Leu Pro Arg Gly Glu Pro Pro Gly Arg
            115             120             125

Leu Lys Ser Ala Pro Leu Phe Met Leu Asp Leu Tyr Asn Ala Leu Ser
 130             135             140

Ala Asp Asn Asp Glu Asp Gly Ala Ser Glu Gly Glu Arg Gln Gln Ser
145             150             155             160

Trp Pro His Glu Ala Ala Ser Ser Ser Gln Arg Arg Gln Pro Pro
            165             170             175

Gly Ala Ala His Pro Leu Asn Arg Lys Ser Leu Leu Ala Pro Gly Ser
            180             185             190

Gly Ser Gly Gly Ala Ser Pro Leu Thr Ser Ala Gln Asp Ser Ala Phe
    195             200             205

Leu Asn Asp Ala Asp Met Val Met Ser Phe Val Asn Leu Val Glu Tyr
    210             215             220

Asp Lys Glu Phe Ser Pro Arg Gln Arg His His Lys Glu Phe Lys Phe
225             230             235             240

Asn Leu Ser Gln Ile Pro Glu Gly Glu Val Val Thr Ala Ala Glu Phe
            245             250             255

Arg Ile Tyr Lys Asp Cys Val Met Gly Ser Phe Lys Asn Gln Thr Phe
            260             265             270

Leu Ile Ser Ile Tyr Gln Val Leu Gln Glu His Gln His Arg Asp Ser
            275             280             285

Asp Leu Phe Leu Leu Asp Thr Arg Val Val Trp Ala Ser Glu Glu Gly
    290             295             300

Trp Leu Glu Phe Asp Ile Thr Ala Thr Ser Asn Leu Trp Val Val Thr
305             310             315             320

Pro Gln His Asn Met Gly Leu Gln Leu Ser Val Val Thr Arg Asp Gly
            325             330             335

Val His Val His Pro Arg Ala Ala Gly Leu Val Gly Arg Asp Gly Pro
            340             345             350

Tyr Asp Lys Gln Pro Phe Met Val Ala Phe Phe Lys Val Ser Glu Val
            355             360             365

His Val Arg Thr Thr Arg Ser Ala Ser Ser Arg Arg Arg Gln Gln Ser
            370             375             380

Arg Asn Arg Ser Thr Gln Ser Gln Asp Val Ala Arg Val Ser Ser Ala
385             390             395             400

Ser Asp Tyr Asn Ser Ser Glu Leu Lys Thr Ala Cys Arg Lys His Glu
            405             410             415

Leu Tyr Val Ser Phe Gln Asp Leu Gly Trp Gln Asp Trp Ile Ile Ala
            420             425             430
```

```
Pro Lys Gly Tyr Ala Ala Asn Tyr Cys Asp Gly Glu Cys Ser Phe Pro
            435                 440                 445
Leu Asn Ala His Met Asn Ala Thr Asn His Ala Ile Val Gln Thr Leu
450                 455                 460
Val His Leu Met Asn Pro Glu Tyr Val Pro Lys Pro Cys Cys Ala Pro
465                 470                 475                 480
Thr Lys Leu Asn Ala Ile Ser Val Leu Tyr Phe Asp Asp Asn Ser Asn
                485                 490                 495
Val Ile Leu Lys Lys Tyr Arg Asn Met Val Val Arg Ala Cys Gly Cys
            500                 505                 510
His
```

<210> SEQ ID NO 3
<211> LENGTH: 2410
<212> TYPE: DNA
<213> ORGANISM: Mus musculus
<220> FEATURE:
<221> NAME/KEY: CDS
<222> LOCATION: (218)..(1750)

<400> SEQUENCE: 3

| | |
|---|---|
| gatcctggcc gtcgcccgt cgtctcttct ccacccgggc ttctgggggc gccgcggatg | 60 |
| accatgagag ataaggactg agtgccagga ccgggaagag agcccgccga gaggtggcgg | 120 |
| gggctgccca ctccgagggc acagcctcc gcgctccggc ctcgctccgc cgctcgacgc | 180 |

```
ctcgcgggcc ccgcgggggc agccgggctg ggcggcg atg ccc ggg ctg ggg cgg    235
                                        Met Pro Gly Leu Gly Arg
                                        1               5 agg gcg cag tgg ctg tgc tgg tgg tgg ggg ttg ctg tgc agc tgc ggc    283
Arg Ala Gln Trp Leu Cys Trp Trp Trp Gly Leu Leu Cys Ser Cys Gly
         10                  15                  20 ccc ccg cca ctg cgg ccc cct ctg ccg gta gcc gcg gcc gcc ggg          331
Pro Pro Pro Leu Arg Pro Pro Leu Pro Val Ala Ala Ala Ala Gly
             25                  30                  35 ggg cag ctg ctg gga gcc ggc ggg agc ccg gtg cgc gct gag cag cca    379
Gly Gln Leu Leu Gly Ala Gly Gly Ser Pro Val Arg Ala Glu Gln Pro
    40                  45                  50 ccg cca cag tcc tct tct tcg ggc ttc ctc tat cgg cgg ctc aag acc    427
Pro Pro Gln Ser Ser Ser Ser Gly Phe Leu Tyr Arg Arg Leu Lys Thr
55                  60                  65                  70 cac gag aag cgg gag atg caa aag gag atc ctg tcg gtg ctg ggc ctc    475
His Glu Lys Arg Glu Met Gln Lys Glu Ile Leu Ser Val Leu Gly Leu
                75                  80                  85 ccg cac agg ccg cgg ccc ctg cac ggt ctc cag cag cct cag ccc ccg    523
Pro His Arg Pro Arg Pro Leu His Gly Leu Gln Gln Pro Gln Pro Pro
            90                  95                 100 gtg ctc ccg cca cag cag cag cag cag cag cag cag cag acg gcc       571
Val Leu Pro Pro Gln Gln Gln Gln Gln Gln Gln Gln Gln Thr Ala
        105                 110                 115 cgc gag gag ccc cct cca ggg cgg ctg aag tcc gct cca ctc ttc atg    619
Arg Glu Glu Pro Pro Pro Gly Arg Leu Lys Ser Ala Pro Leu Phe Met
    120                 125                 130 ctg gat ctc tac aac gcc ctg tcc aat gac gac gaa gag gat ggg gca    667
Leu Asp Leu Tyr Asn Ala Leu Ser Asn Asp Asp Glu Glu Asp Gly Ala
135                 140                 145                 150 tcg gag ggt gtg ggg caa gag cct ggg tcc cac gga ggg gcc agc tcg    715
Ser Glu Gly Val Gly Gln Glu Pro Gly Ser His Gly Gly Ala Ser Ser
                155                 160                 165 tcc cag ctc agg cag ccg tct ccc ggc gct gca cac tcc ttg aac cgc    763
```

```
              Ser Gln Leu Arg Gln Pro Ser Pro Gly Ala Ala His Ser Leu Asn Arg
                          170                 175                 180 aag agt ctc ctg gcc ccg gga ccc ggt ggc ggt gcg tcc cca ctg act          811
Lys Ser Leu Leu Ala Pro Gly Pro Gly Gly Gly Ala Ser Pro Leu Thr
            185                 190                 195 agc gcg cag gac agc gct ttc ctc aac gac gcg gac atg gtc atg agc          859
Ser Ala Gln Asp Ser Ala Phe Leu Asn Asp Ala Asp Met Val Met Ser
200                 205                 210 ttt gtg aac ctg gtg gag tac gac aag gag ttc tcc cca cat caa cga          907
Phe Val Asn Leu Val Glu Tyr Asp Lys Glu Phe Ser Pro His Gln Arg
215                 220                 225                 230 cac cac aaa gag ttc aag ttc aac cta tcc cag att cct gag ggt gag          955
His His Lys Glu Phe Lys Phe Asn Leu Ser Gln Ile Pro Glu Gly Glu
                235                 240                 245 gcg gtg acg gct gct gag ttc cgc gtc tac aag gac tgt gtg gtg ggg         1003
Ala Val Thr Ala Ala Glu Phe Arg Val Tyr Lys Asp Cys Val Val Gly
            250                 255                 260 agt ttt aaa aac caa acc ttt ctt atc agc att tac caa gtc ttg cag         1051
Ser Phe Lys Asn Gln Thr Phe Leu Ile Ser Ile Tyr Gln Val Leu Gln
265                 270                 275 gag cat cag cac aga gac tct gac cta ttt ttg ttg gac acc cgg gtg         1099
Glu His Gln His Arg Asp Ser Asp Leu Phe Leu Leu Asp Thr Arg Val
280                 285                 290 gtg tgg gcc tca gaa gaa ggt tgg ctg gaa ttt gac atc aca gca act         1147
Val Trp Ala Ser Glu Glu Gly Trp Leu Glu Phe Asp Ile Thr Ala Thr
295                 300                 305                 310 agc aat ctg tgg gtg gtg aca ccg cag cac aac atg ggg ctc cag ctg         1195
Ser Asn Leu Trp Val Val Thr Pro Gln His Asn Met Gly Leu Gln Leu
            315                 320                 325 agt gtg gtg act cgg gat gga ctc cac gtc aac ccc cgt gcg gcg ggc         1243
Ser Val Val Thr Arg Asp Gly Leu His Val Asn Pro Arg Ala Ala Gly
                330                 335                 340 ctg gtg ggc aga gac ggc cct tac gac aag cag ccc ttc atg gtg gcc         1291
Leu Val Gly Arg Asp Gly Pro Tyr Asp Lys Gln Pro Phe Met Val Ala
            345                 350                 355 ttc ttc aag gtg agc gag gtc cac gtg cgc acc acc agg tca gcc tcc         1339
Phe Phe Lys Val Ser Glu Val His Val Arg Thr Thr Arg Ser Ala Ser
360                 365                 370 agt cgg cgg cgg cag cag agt cgc aac cgg tcc acc cag tcg cag gac         1387
Ser Arg Arg Arg Gln Gln Ser Arg Asn Arg Ser Thr Gln Ser Gln Asp
375                 380                 385                 390 gtg tcc cgg ggc tcc ggt tct tca gac tac aac ggc agt gag tta aaa         1435
Val Ser Arg Gly Ser Gly Ser Ser Asp Tyr Asn Gly Ser Glu Leu Lys
            395                 400                 405 aca gct tgc aag aag cat gag ctc tat gtg agc ttc cag gac ctg gga         1483
Thr Ala Cys Lys Lys His Glu Leu Tyr Val Ser Phe Gln Asp Leu Gly
                410                 415                 420 tgg cag gac tgg atc att gca ccc aaa ggc tac gct gcc aac tac tgt         1531
Trp Gln Asp Trp Ile Ile Ala Pro Lys Gly Tyr Ala Ala Asn Tyr Cys
            425                 430                 435 gat gga gag tgt tcc ttc cca ctc aac gca cac atg aat gcc acc aac         1579
Asp Gly Glu Cys Ser Phe Pro Leu Asn Ala His Met Asn Ala Thr Asn
440                 445                 450 cac gcc att gta cag acc ttg gtc cac ctt atg aat ccc gag tac gtc         1627
His Ala Ile Val Gln Thr Leu Val His Leu Met Asn Pro Glu Tyr Val
455                 460                 465                 470 ccc aaa cca tgc tgc gca cca acc aaa ctg aat gcc atc tcg gtt ctt         1675
Pro Lys Pro Cys Cys Ala Pro Thr Lys Leu Asn Ala Ile Ser Val Leu
            475                 480                 485
```

```
tac ttc gat gat aac tcc aat gtc atc ttg aaa aag tac agg aat atg      1723
Tyr Phe Asp Asp Asn Ser Asn Val Ile Leu Lys Lys Tyr Arg Asn Met
            490                 495                 500 gtc gtg aga gct tgt ggt tgc cat taa gttgaagctg gtgtgtgt              1770
Val Val Arg Ala Cys Gly Cys His
505             510 gtgggtgggg gcatggttct gccttggatt cctaacaaca acatctgcct taaaccacga    1830
acaacagcac agcgaagcgg gatggtgaca cacagaggga tcgtgacacg cagacacatc    1890
tcccgctggt gccttaccca cggaggcttt tatgaggacc ttgtcaaggg ctttcccagt    1950
tcctaactga gcagttgctg gtctgcagga agctggaagg cttgtagtac aggcctggaa    2010
actgcagtta cctaatgttc gcctccccca accccgcccg gagtagtttt agcttttaga    2070
tctagctgct tgtggtgtaa gtagagagta aacttgaagg aatattaaat atccctgggt    2130
tgaaagaccc ggtggtggct ctacagcacc catcccaggg agattttgc agacatccga     2190 atggagggga aagggcact ctttcaggtt ccattcccag caagggcagc tcacacagga     2250
cctgcagcct ggccatcagc aggctctgtg gaggtgcctt ctgtctactg ttgtagttac    2310
gtgttttgtg ttgactctcg gtggtgtgag aatgtactaa tctctgtcaa gacaaactgt    2370
agcatttcca ccccatcctc ctccctccct cacagaattc                          2410
```

<210> SEQ ID NO 4
<211> LENGTH: 510
<212> TYPE: PRT
<213> ORGANISM: Mus musculus

<400> SEQUENCE: 4

```
Met Pro Gly Leu Gly Arg Arg Ala Gln Trp Leu Cys Trp Trp Trp Gly
1               5                   10                  15

Leu Leu Cys Ser Cys Gly Pro Pro Leu Arg Pro Pro Leu Pro Val
                20                  25                  30

Ala Ala Ala Ala Gly Gly Gln Leu Leu Gly Ala Gly Gly Ser Pro
            35                  40                  45

Val Arg Ala Glu Gln Pro Pro Pro Gln Ser Ser Ser Ser Gly Phe Leu
50                  55                  60

Tyr Arg Arg Leu Lys Thr His Glu Lys Arg Glu Met Gln Lys Glu Ile
65                  70                  75                  80

Leu Ser Val Leu Gly Leu Pro His Arg Pro Arg Pro Leu His Gly Leu
                85                  90                  95

Gln Gln Pro Gln Pro Pro Val Leu Pro Pro Gln Gln Gln Gln Gln Gln
            100                 105                 110

Gln Gln Gln Gln Thr Ala Arg Glu Glu Pro Pro Pro Gly Arg Leu Lys
        115                 120                 125

Ser Ala Pro Leu Phe Met Leu Asp Leu Tyr Asn Ala Leu Ser Asn Asp
    130                 135                 140

Asp Glu Glu Asp Gly Ala Ser Glu Gly Val Gly Gln Glu Pro Gly Ser
145                 150                 155                 160

His Gly Gly Ala Ser Ser Ser Gln Leu Arg Gln Pro Ser Pro Gly Ala
                165                 170                 175

Ala His Ser Leu Asn Arg Lys Ser Leu Leu Ala Pro Gly Pro Gly Gly
            180                 185                 190

Gly Ala Ser Pro Leu Thr Ser Ala Gln Asp Ser Ala Phe Leu Asn Asp
        195                 200                 205

Ala Asp Met Val Met Ser Phe Val Asn Leu Val Glu Tyr Asp Lys Glu
    210                 215                 220
```

```
Phe Ser Pro His Gln Arg His His Lys Glu Phe Lys Phe Asn Leu Ser
225                 230                 235                 240

Gln Ile Pro Glu Gly Glu Ala Val Thr Ala Ala Glu Phe Arg Val Tyr
            245                 250                 255

Lys Asp Cys Val Val Gly Ser Phe Lys Asn Gln Thr Phe Leu Ile Ser
        260                 265                 270

Ile Tyr Gln Val Leu Gln Glu His Gln His Arg Asp Ser Asp Leu Phe
    275                 280                 285

Leu Leu Asp Thr Arg Val Val Trp Ala Ser Glu Glu Gly Trp Leu Glu
290                 295                 300

Phe Asp Ile Thr Ala Thr Ser Asn Leu Trp Val Val Thr Pro Gln His
305                 310                 315                 320

Asn Met Gly Leu Gln Leu Ser Val Val Thr Arg Asp Gly Leu His Val
                325                 330                 335

Asn Pro Arg Ala Ala Gly Leu Val Gly Arg Asp Gly Pro Tyr Asp Lys
            340                 345                 350

Gln Pro Phe Met Val Ala Phe Phe Lys Val Ser Glu Val His Val Arg
        355                 360                 365

Thr Thr Arg Ser Ala Ser Ser Arg Arg Arg Gln Ser Arg Asn Arg
370                 375                 380

Ser Thr Gln Ser Gln Asp Val Ser Arg Gly Ser Gly Ser Ser Asp Tyr
385                 390                 395                 400

Asn Gly Ser Glu Leu Lys Thr Ala Cys Lys Lys His Glu Leu Tyr Val
                405                 410                 415

Ser Phe Gln Asp Leu Gly Trp Gln Asp Trp Ile Ile Ala Pro Lys Gly
            420                 425                 430

Tyr Ala Ala Asn Tyr Cys Asp Gly Glu Cys Ser Phe Pro Leu Asn Ala
        435                 440                 445

His Met Asn Ala Thr Asn His Ala Ile Val Gln Thr Leu Val His Leu
    450                 455                 460

Met Asn Pro Glu Tyr Val Pro Lys Pro Cys Cys Ala Pro Thr Lys Leu
465                 470                 475                 480

Asn Ala Ile Ser Val Leu Tyr Phe Asp Asp Asn Ser Asn Val Ile Leu
                485                 490                 495

Lys Lys Tyr Arg Asn Met Val Val Arg Ala Cys Gly Cys His
            500                 505                 510

<210> SEQ ID NO 5
<211> LENGTH: 2234
<212> TYPE: DNA
<213> ORGANISM: Homo sapiens
<220> FEATURE:
<221> NAME/KEY: CDS
<222> LOCATION: (326)..(1606)

<400> SEQUENCE: 5
accgtcaact cagtagccac ctccctccct gctcagctgt ccagtactct ggccagccat      60
atactccccc ttcccccccat accaaacctt ctctggttcc ctgacctcag tgagacagca    120
gccggcctgg ggacctgggg gagacacgga ggaccccctg gctggagctg acccacagag    180
tagggaatca tggctggaga attggatagc agagtaatgt ttgacctctg gaaacatcac    240
ttacagggct tccggtcaaa attcactagg taggagggtc atcagctggg aagaaccggc    300
gcctgggaaa cctggctgga taggt atg ggg gag cca ggc cag tcc cct agt      352
                            Met Gly Glu Pro Gly Gln Ser Pro Ser
                              1               5
```

| | | |
|---|---|---|
| ccc agg tcc tcc cat ggc agt ccc cca act cta agc act ctc act ctc<br>Pro Arg Ser Ser His Gly Ser Pro Pro Thr Leu Ser Thr Leu Thr Leu<br>10                      15                    20                   25 | 400 |
| ctg ctg ctc ctc tgt gga cat gct cat tct caa tgc aag atc ctc cgc<br>Leu Leu Leu Leu Cys Gly His Ala His Ser Gln Cys Lys Ile Leu Arg<br>                  30                    35                    40 | 448 |
| tgc aat gct gag tac gta tcg tcc act ctg agc ctt aga ggt ggg ggt<br>Cys Asn Ala Glu Tyr Val Ser Ser Thr Leu Ser Leu Arg Gly Gly Gly<br>            45                    50                    55 | 496 |
| tca gga gca ctt cga gga gga gga gga ggc cgg ggt gga ggg<br>Ser Gly Ala Leu Arg Gly Gly Gly Gly Gly Arg Gly Gly Gly<br>        60                    65                    70 | 544 |
| gtg ggc tct ggc ggc ctc tgt cga gcc ctc cgc tcc tat gcg ctc tgc<br>Val Gly Ser Gly Gly Leu Cys Arg Ala Leu Arg Ser Tyr Ala Leu Cys<br>      75                    80                    85 | 592 |
| act cgg cgc acc gcc cgc acc tgc cgc ggg gac ctc gcc ttc cat tcg<br>Thr Arg Arg Thr Ala Arg Thr Cys Arg Gly Asp Leu Ala Phe His Ser<br>90                      95                   100              105 | 640 |
| gcg gta cat ggc atc gaa gac ctg atg atc cag cac aac tgc tcc cgc<br>Ala Val His Gly Ile Glu Asp Leu Met Ile Gln His Asn Cys Ser Arg<br>                  110                 115               120 | 688 |
| cag ggc cct aca gcc cct ccc ccg ccc cgg ggc ccc gcc ctt cca ggc<br>Gln Gly Pro Thr Ala Pro Pro Pro Pro Arg Gly Pro Ala Leu Pro Gly<br>            125                    130                 135 | 736 |
| gcg ggc tcc ggc ctc cct gcc ccg gac cct tgt gac tat gaa ggc cgg<br>Ala Gly Ser Gly Leu Pro Ala Pro Asp Pro Cys Asp Tyr Glu Gly Arg<br>        140                    145                    150 | 784 |
| ttt tcc cgg ctg cat ggt cgt ccc ccg ggg ttc ttg cat tgc gct tcc<br>Phe Ser Arg Leu His Gly Arg Pro Pro Gly Phe Leu His Cys Ala Ser<br>      155                    160                    165 | 832 |
| ttc ggg gac ccc cat gtg cgc agc ttc cac cat cac ttt cac aca tgc<br>Phe Gly Asp Pro His Val Arg Ser Phe His His His Phe His Thr Cys<br>170                     175                   180              185 | 880 |
| cgt gtc caa gga gct tgg cct cta ctg gat aat gac ttc ctc ttt gtc<br>Arg Val Gln Gly Ala Trp Pro Leu Leu Asp Asn Asp Phe Leu Phe Val<br>            190                    195                    200 | 928 |
| caa gcc acc agc tcc ccc atg gcg ttg ggg gcc aac gct acc gcc acc<br>Gln Ala Thr Ser Ser Pro Met Ala Leu Gly Ala Asn Ala Thr Ala Thr<br>        205                    210                    215 | 976 |
| cgg aag ctc acc atc ata ttt aag aac atg cag gaa tgc att gat cag<br>Arg Lys Leu Thr Ile Ile Phe Lys Asn Met Gln Glu Cys Ile Asp Gln<br>      220                    225                    230 | 1024 |
| aag gtg tat cag gct gag gtg gat aat ctt cct gta gcc ttt gaa gat<br>Lys Val Tyr Gln Ala Glu Val Asp Asn Leu Pro Val Ala Phe Glu Asp<br>      235                    240                    245 | 1072 |
| ggt tct atc aat gga ggt gac cga cct ggg gga tcc agt ttg tcg att<br>Gly Ser Ile Asn Gly Gly Asp Arg Pro Gly Gly Ser Ser Leu Ser Ile<br>250                     255                   260              265 | 1120 |
| caa act gct aac cct ggg aac cat gtg gag atc caa gct gcc tac att<br>Gln Thr Ala Asn Pro Gly Asn His Val Glu Ile Gln Ala Ala Tyr Ile<br>        270                    275                    280 | 1168 |
| ggc aca act ata atc att cgg cag aca gct ggg cag ctc tcc ttc tcc<br>Gly Thr Thr Ile Ile Ile Arg Gln Thr Ala Gly Gln Leu Ser Phe Ser<br>            285                    290                 295 | 1216 |
| atc aag gta gca gag gat gtg gcc atg gcc ttc tca gct gaa cag gac<br>Ile Lys Val Ala Glu Asp Val Ala Met Ala Phe Ser Ala Glu Gln Asp<br>            300                    305                 310 | 1264 |
| ctg cag ctc tgt gtt ggg ggg tgc cct cca agt cag cga ctc tct cga<br>Leu Gln Leu Cys Val Gly Gly Cys Pro Pro Ser Gln Arg Leu Ser Arg | 1312 |

```
                   315                 320                 325
tca gag cgc aat cgt cgg gga gct ata acc att gat act gcc aga cgg     1360
Ser Glu Arg Asn Arg Arg Gly Ala Ile Thr Ile Asp Thr Ala Arg Arg
330                 335                 340                 345 ctg tgc aag gaa ggg ctt cca gtg gaa gat gct tac ttc cat tcc tgt     1408
Leu Cys Lys Glu Gly Leu Pro Val Glu Asp Ala Tyr Phe His Ser Cys
                350                 355                 360 gtc ttt gat gtt tta att tct ggt gat ccc aac ttt acc gtg gca gct     1456
Val Phe Asp Val Leu Ile Ser Gly Asp Pro Asn Phe Thr Val Ala Ala
            365                 370                 375 cag gca gca ctg gag gat gcc cga gcc ttc ctg cca gac tta gag aag     1504
Gln Ala Ala Leu Glu Asp Ala Arg Ala Phe Leu Pro Asp Leu Glu Lys
        380                 385                 390 ctg cat ctc ttc ccc tca gat gct ggg gtt cct ctt tcc tca gca acc     1552
Leu His Leu Phe Pro Ser Asp Ala Gly Val Pro Leu Ser Ser Ala Thr
    395                 400                 405 ctc tta gct cca ctc ctt tct ggg ctc ttt gtt ctg tgg ctt tgc att     1600
Leu Leu Ala Pro Leu Leu Ser Gly Leu Phe Val Leu Trp Leu Cys Ile
410                 415                 420                 425 cag taa gggaccatc agtcccatta ctagtttgga aatgatttgg agatacagat      1656
Gln tggcatagaa gaatgtaaag aatcattaaa ggaagcaggg cctaggagac acgtgaaaca   1716
atgacattat ccagagtcag atgaggctgc agtccaggtt gaaattatc acagaataag   1776 gattctgggc aaggttactg cattccggat ctctgtgggg ctcttcacca attttccag   1836 cctcattat agtaaacaaa ttgttctaat ccatttactg cagatttcac ccttataagt   1896
ttagaggtca tgaaggtttt aatgatcagt aaagatttaa gggttgagat ttttaagagg   1956
caagagctga aagcagaaga catgatcatt agccataaga aactcaaagg aggaagacat   2016
aattagggaa agaagtctat ttgatgaata tgtgtgtgta aggtatgttc tgctttcttg   2076
attcaaaaat gaagcaggca ttgtctagct cttaggtgaa gggagtctct gcttttgaag   2136
aatggcacag gtaggacaga agtatcatcc ctacccccta actaatctgt tattaaagct   2196
acaaattctt cacaccatca aaaaaaaaaa aaaaaaaa                          2234
```

<210> SEQ ID NO 6
<211> LENGTH: 426
<212> TYPE: PRT
<213> ORGANISM: Homo sapiens

<400> SEQUENCE: 6

```
Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Ser Gly Ala Leu Arg Gly
    50                  55                  60

Gly Gly Gly Gly Arg Gly Gly Val Gly Ser Gly Gly Leu Cys
65                  70                  75                  80

Arg Ala Leu Arg Ser Tyr Ala Leu Cys Thr Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
```

```
            115                 120                 125
Pro Pro Arg Gly Pro Ala Leu Pro Gly Ala Gly Ser Gly Leu Pro Ala
130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
                180                 185                 190

Leu Leu Asp Asn Asp Phe Leu Phe Val Gln Ala Thr Ser Ser Pro Met
            195                 200                 205

Ala Leu Gly Ala Asn Ala Thr Ala Arg Lys Leu Thr Ile Ile Phe
210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
                260                 265                 270

His Val Glu Ile Gln Ala Ala Tyr Ile Gly Thr Thr Ile Ile Ile Arg
            275                 280                 285

Gln Thr Ala Gly Gln Leu Ser Phe Ser Ile Lys Val Ala Glu Asp Val
290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
                340                 345                 350

Val Glu Asp Ala Tyr Phe His Ser Cys Val Phe Asp Val Leu Ile Ser
            355                 360                 365

Gly Asp Pro Asn Phe Thr Val Ala Ala Gln Ala Ala Leu Glu Asp Ala
370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425

<210> SEQ ID NO 7
<211> LENGTH: 1732
<212> TYPE: DNA
<213> ORGANISM: Homo sapiens
<220> FEATURE:
<221> NAME/KEY: CDS
<222> LOCATION: (404)..(1186)

<400> SEQUENCE: 7
tttacggcgc ggagccggag agacctgggc tggcgcgggc gggagctgcg gcggataccc        60
ttgcgtgctg tggagaccct actctcttcg ctgagaacgg ccgctagcgg ggactgaagg       120
ccgggagccc actcccgacc cggggctagc gtgcgtccct agagtcgagc ggggcaaggg       180
agccagtggc cgccgacggg ggaccgggaa acttttctgg gctcctgggc gcgcctgta        240 gccgcgctcc atgctccggc agcggcccga aacccagccc cgccgctgac ggcgcccgcc       300
```

```
gctccgggca gggcccatgc cctgcgcgct ccggggtcg taggctgccg ccgagccggg      360
gctccggaag ccggcggggg cgccgcggcc gtgcggggcg tca atg gat cgc cac      415
                                              Met Asp Arg His
                                               1 tcc agc tac atc ttc atc tgg ctg cag ctg gag ctc tgc gcc atg gcc      463
Ser Ser Tyr Ile Phe Ile Trp Leu Gln Leu Glu Leu Cys Ala Met Ala
 5              10                  15                  20 gtg ctg ctc acc aaa ggt gaa att cga tgc tac tgt gat gct gcc cac      511
Val Leu Leu Thr Lys Gly Glu Ile Arg Cys Tyr Cys Asp Ala Ala His
                25                  30                  35 tgt gta gcc act ggt tat atg tgt aaa tct gag ctc agc gcc tgc ttc      559
Cys Val Ala Thr Gly Tyr Met Cys Lys Ser Glu Leu Ser Ala Cys Phe
            40                  45                  50 tct aga ctt ctt gat cct cag aac tca aat tcc cca ctc acc cat ggc      607
Ser Arg Leu Leu Asp Pro Gln Asn Ser Asn Ser Pro Leu Thr His Gly
        55                  60                  65 tgc ctg gac tct ctt gca agc acg aca gac atc tgc caa gcc aaa cag      655
Cys Leu Asp Ser Leu Ala Ser Thr Thr Asp Ile Cys Gln Ala Lys Gln
 70                  75                  80 gcc cga aac cac tct ggc acc acc ata ccc aca ttg gaa tgc tgt cat      703
Ala Arg Asn His Ser Gly Thr Thr Ile Pro Thr Leu Glu Cys Cys His
 85                  90                  95                 100 gaa gac atg tgc aat tac aga ggg ctg cac gat gtt ctc tct cct ccc      751
Glu Asp Met Cys Asn Tyr Arg Gly Leu His Asp Val Leu Ser Pro Pro
                105                 110                 115 agg ggt gag gcc tca gga caa gga aac agg tat cag cat gat ggt agc      799
Arg Gly Glu Ala Ser Gly Gln Gly Asn Arg Tyr Gln His Asp Gly Ser
            120                 125                 130 aga aac ctt atc acc aag gtg cag gag ctg act tct tcc aaa gag ttg      847
Arg Asn Leu Ile Thr Lys Val Gln Glu Leu Thr Ser Ser Lys Glu Leu
        135                 140                 145 tgg ttc cgg gca gcg gtc att gcc gtg ccc att gct gga ggg ctg att      895
Trp Phe Arg Ala Ala Val Ile Ala Val Pro Ile Ala Gly Gly Leu Ile
150                 155                 160 tta gtg ttg ctt att atg ttg gcc ctg agg atg ctt cga agt gaa aat      943
Leu Val Leu Leu Ile Met Leu Ala Leu Arg Met Leu Arg Ser Glu Asn
165                 170                 175                 180 aag agg ctg cag gat cag cgg caa cag atg ctc tcc cgt ttg cac tac      991
Lys Arg Leu Gln Asp Gln Arg Gln Gln Met Leu Ser Arg Leu His Tyr
                185                 190                 195 agc ttt cac gga cac cat tcc aaa aag ggg cag gtt gca aag tta gac      1039
Ser Phe His Gly His His Ser Lys Lys Gly Gln Val Ala Lys Leu Asp
            200                 205                 210 ttg gaa tgc atg gtg ccg gtc agt ggg cac gag aac tgc tgt ctg acc      1087
Leu Glu Cys Met Val Pro Val Ser Gly His Glu Asn Cys Cys Leu Thr
        215                 220                 225 tgt gat aaa atg aga caa gca gac ctc agc aac gat aag atc ctc tcg      1135
Cys Asp Lys Met Arg Gln Ala Asp Leu Ser Asn Asp Lys Ile Leu Ser
230                 235                 240 ctt gtt cac tgg ggc atg tac agt ggg cac ggg aag ctg gaa ttc gta      1183
Leu Val His Trp Gly Met Tyr Ser Gly His Gly Lys Leu Glu Phe Val
245                 250                 255                 260 tga cggagtctta tctgaactac acttactgaa cagcttgaag gccttttgag          1236
ttctgctgga caggagcact ttatctgaag acaaactcat ttaatcatct ttgagagaca    1296
aaatgacctc tgcaaacaga atcttggata tttcttctga aggattattt gcacagactt    1356
aaatacagtt aaatgtgtta tttgctttta aaattataaa aagcaaagag aagactttgt    1416
```

```
acacactgtc accagggtta tttgcatcca agggagctgg aattgagtac ctaaataaac    1476
aaaaatgtgc cctatgtaag cttctacatc ttgatttatt gtaaagattt aaaagaaata    1536
tatatatttt gtctgaaatt taatagtgtc tttcataaat ttaactggga aacgtgagac    1596
agtacatgtt aattatacaa atggccattt gctgtaata  atttgttctc aactctagga    1656
tgtggcttgg ttttttttt  tctcttttct tttttaaaca agaccaagat cttgcttatt    1716
cttccatgaa aaaaa                                                     1732

<210> SEQ ID NO 8
<211> LENGTH: 260
<212> TYPE: PRT
<213> ORGANISM: Homo sapiens

<400> SEQUENCE: 8

Met Asp Arg His Ser Ser Tyr Ile Phe Ile Trp Leu Gln Leu Glu Leu
1               5                   10                  15

Cys Ala Met Ala Val Leu Leu Thr Lys Gly Glu Ile Arg Cys Tyr Cys
                20                  25                  30

Asp Ala Ala His Cys Val Ala Thr Gly Tyr Met Cys Lys Ser Glu Leu
            35                  40                  45

Ser Ala Cys Phe Ser Arg Leu Leu Asp Pro Gln Asn Ser Asn Ser Pro
        50                  55                  60

Leu Thr His Gly Cys Leu Asp Ser Leu Ala Ser Thr Thr Asp Ile Cys
65                  70                  75                  80

Gln Ala Lys Gln Ala Arg Asn His Ser Gly Thr Thr Ile Pro Thr Leu
                85                  90                  95

Glu Cys Cys His Glu Asp Met Cys Asn Tyr Arg Gly Leu His Asp Val
            100                 105                 110

Leu Ser Pro Pro Arg Gly Glu Ala Ser Gly Gln Gly Asn Arg Tyr Gln
        115                 120                 125

His Asp Gly Ser Arg Asn Leu Ile Thr Lys Val Gln Glu Leu Thr Ser
    130                 135                 140

Ser Lys Glu Leu Trp Phe Arg Ala Ala Val Ile Ala Val Pro Ile Ala
145                 150                 155                 160

Gly Gly Leu Ile Leu Val Leu Leu Ile Met Leu Ala Leu Arg Met Leu
                165                 170                 175

Arg Ser Glu Asn Lys Arg Leu Gln Asp Gln Arg Gln Gln Met Leu Ser
            180                 185                 190

Arg Leu His Tyr Ser Phe His Gly His His Ser Lys Lys Gly Gln Val
        195                 200                 205

Ala Lys Leu Asp Leu Glu Cys Met Val Pro Val Ser Gly His Glu Asn
    210                 215                 220

Cys Cys Leu Thr Cys Asp Lys Met Arg Gln Ala Asp Leu Ser Asn Asp
225                 230                 235                 240

Lys Ile Leu Ser Leu Val His Trp Gly Met Tyr Ser Gly His Gly Lys
                245                 250                 255

Leu Glu Phe Val
            260

<210> SEQ ID NO 9
<211> LENGTH: 2322
<212> TYPE: DNA
<213> ORGANISM: Homo sapiens
<220> FEATURE:
<221> NAME/KEY: CDS
<222> LOCATION: (48)..(689)
```

<400> SEQUENCE: 9

```
agagcctgtg ctactggaag gtggcgtgcc ctcctctggc tggtacc atg cag ctc       56
                                                    Met Gln Leu
                                                    1
cca ctg gcc ctg tgt ctc gtc tgc ctg ctg gta cac aca gcc ttc cgt      104
Pro Leu Ala Leu Cys Leu Val Cys Leu Leu Val His Thr Ala Phe Arg
    5                   10                  15
gta gtg gag ggc cag ggg tgg cag gcg ttc aag aat gat gcc acg gaa      152
Val Val Glu Gly Gln Gly Trp Gln Ala Phe Lys Asn Asp Ala Thr Glu
20                  25                  30                  35
atc atc ccc gag ctc gga gag tac ccc gag cct cca ccg gag ctg gag      200
Ile Ile Pro Glu Leu Gly Glu Tyr Pro Glu Pro Pro Pro Glu Leu Glu
                40                  45                  50
aac aac aag acc atg aac cgg gcg gag aac gga ggg cgg cct ccc cac      248
Asn Asn Lys Thr Met Asn Arg Ala Glu Asn Gly Gly Arg Pro Pro His
            55                  60                  65
cac ccc ttt gag acc aaa gac gtg tcc gag tac agc tgc cgc gag ctg      296
His Pro Phe Glu Thr Lys Asp Val Ser Glu Tyr Ser Cys Arg Glu Leu
        70                  75                  80
cac ttc acc cgc tac gtg acc gat ggg ccg tgc cgc agc gcc aag ccg      344
His Phe Thr Arg Tyr Val Thr Asp Gly Pro Cys Arg Ser Ala Lys Pro
    85                  90                  95
gtc acc gag ctg gtg tgc tcc ggc cag tgc ggc ccg gcg cgc ctg ctg      392
Val Thr Glu Leu Val Cys Ser Gly Gln Cys Gly Pro Ala Arg Leu Leu
100                 105                 110                 115
ccc aac gcc atc ggc cgc ggc aag tgg tgg cga cct agt ggg ccc gac      440
Pro Asn Ala Ile Gly Arg Gly Lys Trp Trp Arg Pro Ser Gly Pro Asp
                120                 125                 130
ttc cgc tgc atc ccc gac cgc tac cgc gcg cag cgc gtg cag ctg ctg      488
Phe Arg Cys Ile Pro Asp Arg Tyr Arg Ala Gln Arg Val Gln Leu Leu
            135                 140                 145
tgt ccc ggt ggt gag gcg ccg cgc gcg cgc aag gtg cgc ctg gtg gcc      536
Cys Pro Gly Gly Glu Ala Pro Arg Ala Arg Lys Val Arg Leu Val Ala
        150                 155                 160
tcg tgc aag tgc aag cgc ctc acc cgc ttc cac aac cag tcg gag ctc      584
Ser Cys Lys Cys Lys Arg Leu Thr Arg Phe His Asn Gln Ser Glu Leu
    165                 170                 175
aag gac ttc ggg acc gag gcc gct cgg ccg cag aag ggc cgg aag ccg      632
Lys Asp Phe Gly Thr Glu Ala Ala Arg Pro Gln Lys Gly Arg Lys Pro
180                 185                 190                 195
cgg ccc cgc gcc cgg agc gcc aaa gcc aac cag gcc gag ctg gag aac      680
Arg Pro Arg Ala Arg Ser Ala Lys Ala Asn Gln Ala Glu Leu Glu Asn
                200                 205                 210
gcc tac tag agcccgcccg cgcccctccc caccggcggg cgccccggcc              729
Ala Tyr
ctgaacccgc gccccacatt tctgtcctct gcgcgtggtt tgattgttta tatttcattg    789
taaatgcctg caacccaggg cagggggctg agaccttcca ggccctgagg aatcccgggc    849
gccggcaagg ccccccctcag cccgccagct gaggggtccc acggggcagg ggagggaatt   909

gagagtcaca gacactgagc cacgcagccc cgcctctggg gccgcctacc tttgctggtc    969
ccacttcaga ggaggcagaa atggaagcat tttcaccgcc ctggggtttt aagggagcgg   1029
tgtgggagtg ggaaagtcca gggactggtt aagaaagttg gataagattc cccccttgcac  1089
ctcgctgccc atcagaaagc ctgaggcgtg cccagagcac aagactgggg gcaactgtag   1149
atgtggtttc tagtcctggc tctgccacta acttgctgtg taaccttgaa ctacacaatt   1209
ctccttcggg acctcaattt ccactttgta aaatgagggt ggaggtggga ataggatctc   1269
```

```
gaggagacta ttggcatatg attccaagga ctccagtgcc ttttgaatgg gcagaggtga    1329
gagagagaga gagaaagaga gagaatgaat gcagttgcat tgattcagtg ccaaggtcac    1389
ttccagaatt cagagttgtg atgctctctt ctgacagcca agatgaaaaa acaaacagaa    1449
aaaaaaaagt aaagagtcta tttatggctg acatatttac ggctgacaaa ctcctggaag    1509
aagctatgct gcttcccagc ctggcttccc cggatgtttg ctacctcca ccctccatc    1569 tcaaagaaat aacatcatcc attggggtag aaaaggagag ggtccgaggg tggtgggagg    1629
gatagaaatc acatccgccc caacttccca agagcagca tccctccccc gacccatagc    1689
catgttttaa agtcaccttc cgaagagaag tgaaaggttc aaggacactg ccttgcagg    1749 cccgagggag cagccatcac aaactcacag accagcacat ccctttgag acaccgcctt    1809 ctgcccacca ctcacggaca catttctgcc tagaaaacag cttcttactg ctcttacatg    1869
tgatggcata tcttacacta aaagaatatt attgggggaa aaactacaag tgctgtacat    1929
atgctgagaa actgcagagc ataatactgc cacccaaaaa tcttttttgaa aatcatttcc    1989 agacaacctc ttactttctg tgtagttttt aattgttaaa aaaaaaagt tttaaacaga    2049 agcacatgac atatgaaagc ctgcaggact ggtcgttttt ttggcaattc ttccacgtgg    2109
gacttgtcca caagaatgaa agtagtggtt tttaaagagt taagttacat atttattttc    2169
tcacttaagt tatttatgca aaagttttc ttgtagagaa tgacaatgtt aatattgctt    2229
tatgaattaa cagtctgttc ttccagagtc cagagacatt gttaataaag acaatgaatc    2289
atgaccgaaa gaaaaaaaaa aaaaaaaaaa aaa                                  2322
```

<210> SEQ ID NO 10
<211> LENGTH: 213
<212> TYPE: PRT
<213> ORGANISM: Homo sapiens

<400> SEQUENCE: 10

```
Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
```

-continued

```
                                180                         185
                                                                              190
Arg Lys Pro Arg Pro Arg Ala Arg Ser Ala Lys Ala Asn Gln Ala Glu
        195                     200                     205

Leu Glu Asn Ala Tyr
        210

<210> SEQ ID NO 11
<211> LENGTH: 1892
<212> TYPE: DNA
<213> ORGANISM: Homo sapiens
<220> FEATURE:
<221> NAME/KEY: CDS
<222> LOCATION: (526)..(1224)

<400> SEQUENCE: 11
aaaccggtgc caacgtgcgc ggacgccgcc gccgccgccg ccgctggagt ccgccgggca      60
gagccggccg cggagcccgg agcaggcgga gggaagtgcc cctagaacca gctcagccag     120
cggcgcttgc acagagcggc cggacgaaga gcagcgagag gaggagggga gagcggctcg     180
tccacgcgcc ctgcgccgcc gccggcccgg gaaggcagcg aggagccggc gcctcccgcg     240
ccccgcggtc gccctggagt aatttcggat gcccagccgc ggccgccttc cccagtagac     300
ccgggagagg agttgcggcc aacttgtgtg ccttttcttcc gccccggtgg gagccggcgc     360
tgcgcgaagg gctctcccgg cggctcatgc tgccggccct cgcctgccc agcctcgggt     420 gagccgcctc cggagagacg ggggagcgcg gcggcgccgc gggctcggcg tgctctcctc     480
cggggacgcg ggacgaagca gcagcccgg gcgcgcgcca gaggc atg gag cgc tgc     537
                                                  Met Glu Arg Cys
                                                  1 ccc agc cta ggg gtc acc ctc tac gcc ctg gtg gtg gtc ctg ggg ctg     585
Pro Ser Leu Gly Val Thr Leu Tyr Ala Leu Val Val Val Leu Gly Leu
5                  10                  15                  20 cgg gcg aca ccg gcc ggc ggc cag cac tat ctc cac atc cgc ccg gca     633
Arg Ala Thr Pro Ala Gly Gly Gln His Tyr Leu His Ile Arg Pro Ala
                25                  30                  35 ccc agc gac aac ctg ccc ctg gtg gac ctc atc gaa cac cca gac cct     681
Pro Ser Asp Asn Leu Pro Leu Val Asp Leu Ile Glu His Pro Asp Pro
        40                  45                  50 atc ttt gac ccc aag gaa aag gat ctg aac gag acg ctg ctg cgc tcg     729
Ile Phe Asp Pro Lys Glu Lys Asp Leu Asn Glu Thr Leu Leu Arg Ser
55                  60                  65 ctg ctc ggg ggc cac tac gac cca ggc ttc atg gcc acc tcg ccc ccc     777
Leu Leu Gly Gly His Tyr Asp Pro Gly Phe Met Ala Thr Ser Pro Pro
    70                  75                  80 gag gac cgg ccc ggg ggc ggg ggt gca gct ggg ggc gcg gag gac     825
Glu Asp Arg Pro Gly Gly Gly Gly Ala Ala Gly Gly Ala Glu Asp
85                  90                  95                  100 ctg gcg gag ctg gac cag ctg ctg cgg cag cgg ccg tcg ggg gcc atg     873
Leu Ala Glu Leu Asp Gln Leu Leu Arg Gln Arg Pro Ser Gly Ala Met
                105                 110                 115 ccg agc gag atc aaa ggg cta gag ttc tcc gag ggc ttg gcc cag ggc     921
Pro Ser Glu Ile Lys Gly Leu Glu Phe Ser Glu Gly Leu Ala Gln Gly
        120                 125                 130 aag aag cag cgc cta agc aag aag ctg cgg agg aag tta cag atg tgg     969
Lys Lys Gln Arg Leu Ser Lys Lys Leu Arg Arg Lys Leu Gln Met Trp
135                 140                 145 ctg tgg tcg cag aca ttc tgc ccc gtg ctg tac gcg tgg aac gac ctg    1017
Leu Trp Ser Gln Thr Phe Cys Pro Val Leu Tyr Ala Trp Asn Asp Leu
    150                 155                 160
```

-continued

| | | | | | | | | | | | | | | | |
|---|---|---|---|---|---|---|---|---|---|---|---|---|---|---|---|
| ggc | agc | cgc | ttt | tgg | ccg | cgc | tac | gtg | aag | gtg | ggc | agc | tgc | ttc | agt | 1065 |
| Gly | Ser | Arg | Phe | Trp | Pro | Arg | Tyr | Val | Lys | Val | Gly | Ser | Cys | Phe | Ser | |
| 165 | | | | 170 | | | | | 175 | | | | | 180 | | |

| | | | | | | | | | | | | | | |
|---|---|---|---|---|---|---|---|---|---|---|---|---|---|---|---|
| aag | cgc | tcg | tgc | tcc | gtg | ccc | gag | ggc | atg | gtg | tgc | aag | ccg | tcc | aag | 1113 |
| Lys | Arg | Ser | Cys | Ser | Val | Pro | Glu | Gly | Met | Val | Cys | Lys | Pro | Ser | Lys | |
| | | | | 185 | | | | 190 | | | | | 195 | | | |

| | | | | | | | | | | | | | | | |
|---|---|---|---|---|---|---|---|---|---|---|---|---|---|---|---|
| tcc | gtg | cac | ctc | acg | gtg | ctg | cgg | tgg | cgc | tgt | cag | cgg | cgc | ggg | ggc | 1161 |
| Ser | Val | His | Leu | Thr | Val | Leu | Arg | Trp | Arg | Cys | Gln | Arg | Arg | Gly | Gly | |
| | | | 200 | | | | | 205 | | | | | 210 | | | |

| | | | | | | | | | | | | | | | |
|---|---|---|---|---|---|---|---|---|---|---|---|---|---|---|---|
| cag | cgc | tgc | ggc | tgg | att | ccc | atc | cag | tac | ccc | atc | att | tcc | gag | tgc | 1209 |
| Gln | Arg | Cys | Gly | Trp | Ile | Pro | Ile | Gln | Tyr | Pro | Ile | Ile | Ser | Glu | Cys | |
| | | 215 | | | | | 220 | | | | | 225 | | | | |

| | | | | | | |
|---|---|---|---|---|---|---|
| aag | tgc | tcg | tgc | tag | aactcggggg ccccctgccc gcacccggac acttgatcga | 1264 |
| Lys | Cys | Ser | Cys | | | |
| 230 | | | | | | |

| | |
|---|---|
| tccccaccga cgccccctgc accgcctcca accagttcca ccaccctcta gcgagggttt | 1324 |
| tcaatgaact tttttttttt tttttttttt tttttctggg ctacagagac ctagctttct | 1384 |
| ggttcctgta atgcactgtt taactgtgta ggaatgtata tgtgtgtgta tatacggtcc | 1444 |
| cagtttaat ttacttatta aaaggtcagt attatacgtt aaaagttacc ggcttctact | 1504 |
| gtattttaa aaaaaagtaa gcaaagaaa aaaaaagaa cagagaaaag agagacttat | 1564 |
| tctggttgtt gctaataatg ttaacctgct atttatattc cagtgcccctt cgcatggcga | 1624 |
| agcagggggg aaaagttatt ttttttcttga agtacaaaga gacggggaa cttttgtaga | 1684 |
| ggacttttta aaagctattt tccattcttc ggaaagtgtt ttggttttcc ttggacctcg | 1744 |
| aagaagctat agagttcaat gttatttttac agtattgta aatatagaga acaaatggaa | 1804 |
| tgactaatca ttgtaaatta agagtatctg ctatttattc tttataatat cccgtgtagt | 1864 |
| aaatgagaaa gaagtgcaga gcaggatt | 1892 |

<210> SEQ ID NO 12
<211> LENGTH: 232
<212> TYPE: PRT
<213> ORGANISM: Homo sapiens

<400> SEQUENCE: 12

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Lys Leu Arg Arg Lys
    130                 135                 140

Leu Gln Met Trp Leu Trp Ser Gln Thr Phe Cys Pro Val Leu Tyr Ala
145                 150                 155                 160

```
Trp Asn Asp Leu Gly Ser Arg Phe Trp Pro Arg Tyr Val Lys Val Gly
            165                 170                 175
Ser Cys Phe Ser Lys Arg Ser Cys Ser Val Pro Glu Gly Met Val Cys
        180                 185                 190
Lys Pro Ser Lys Ser Val His Leu Thr Val Leu Arg Trp Arg Cys Gln
        195                 200                 205
Arg Arg Gly Gly Gln Arg Cys Gly Trp Ile Pro Ile Gln Tyr Pro Ile
    210                 215                 220
Ile Ser Glu Cys Lys Cys Ser Cys
225                 230

<210> SEQ ID NO 13
<211> LENGTH: 19271
<212> TYPE: DNA
<213> ORGANISM: Homo sapiens

<400> SEQUENCE: 13
```

| | | | | | |
|---|---|---|---|---|---|
| ccttcagttc | ttaaagcgct | gcaattcgct | gctgcagcca | tatttcttac | tctctcgggg | 60 |
| ctggaagctt | cctgactgaa | gatctctctg | cacttggggt | tctttctaga | acattttcta | 120 |
| gtcccccaac | acccttatg | gcgtatttct | ttaaaaaaat | cacctaaatt | ccataaaata | 180 |
| ttttttaaa | ttctatactt | tctcctagtg | tcttcttgac | acgtcctcca | tatttttta | 240 |
| aagaaagtat | ttggaatatt | ttgaggcaat | ttttaatatt | taaggaattt | ttctttggaa | 300 |
| tcattttgg | ttgacatctc | tgttttttgt | ggatcagttt | tttactcttc | cactctcttt | 360 |
| tctatatttt | gcccatcggg | gctgcggata | cctggttta | ttattttc | tttgcccaac | 420 |
| ggggccgtgg | atacctgcct | tttaattctt | ttttattcgc | ccatcggggc | cgcggatacc | 480 |
| tgcttttat | ttttttttcc | ttagcccatc | ggggtatcgg | atacctgctg | attcccttcc | 540 |
| cctctgaacc | cccaacactc | tggcccatcg | gggtgacgga | tatctgcttt | ttaaaaattt | 600 |
| tctttttttg | gcccatcggg | gcttcggata | cctgcttttt | tttttttat | ttttccttgc | 660 |
| ccatcgggc | ctcggatacc | tgctttaatt | tttgtttttc | tggcccatcg | gggccgcgga | 720 |
| tacctgcttt | gatttttttt | tttcatcgcc | catcggtgct | tttatggat | gaaaaatgt | 780 |
| tggttttgtg | ggttgttgca | ctctctggaa | tatctacact | tttttttgct | gctgatcatt | 840 |
| tggtggtgtg | tgagtgtacc | taccgctttg | gcagagaatg | actctgcagt | taagctaagg | 900 |
| gcgtgttcag | attgtggagg | aaaagtggcc | gccattttag | acttgccgca | taactcggct | 960 |
| tagggctagt | cgtttgtgct | aagttaaact | agggaggcaa | gatggatgat | agcaggtcag | 1020 |
| gcagaggaag | tcatgtgcat | tgcatgagct | aaacctatct | gaatgaattg | atttggggct | 1080 |
| tgttaggagc | tttgcgtgat | tgttgtatcg | ggaggcagta | agaatcatct | tttatcagta | 1140 |
| caagggacta | gttaaaaatg | gaaggttagg | aaagactaag | gtgcagggct | taaaatggcg | 1200 |
| attttgacat | tgcggcattg | ctcagcatgg | cgggctgtgc | tttgttaggt | tgtccaaaat | 1260 |
| ggcggatcca | gttctgtcgc | agtgttcaag | tggcgggaag | gccacatcat | gatgggcgag | 1320 |
| gctttgttaa | gtggttagca | tggtggtgga | catgtgcggt | cacacaggaa | aagatggcgg | 1380 |
| ctgaaggtct | tgccgcagtg | taaaacatgg | cgggcctctt | tgtctttgct | gtgtgctttt | 1440 |
| cgtgttgggt | tttgccgcag | ggacaatatg | gcaggcgttg | tcatatgtat | atcatggctt | 1500 |
| ttgtcacgtg | gacatcatgg | cgggcttgcc | gcattgttaa | agatggcggg | ttttgccgcc | 1560 |
| tagtgccacg | cagagcggga | gaaaaggtgg | gatggacagt | gctggattgc | tgcataaccc | 1620 |
| aaccaattag | aaatgggggt | ggaattgatc | acagccaatt | agagcagaag | atggaattag | 1680 |

```
actgatgaca cactgtccag ctactcagcg aagacctggg tgaattagca tggcacttcg   1740
cagctgtctt tagccagtca ggagaaagaa gtggaggggc cacgtgtatg tctcccagtg   1800
ggcggtacac caggtgtttt caaggtcttt tcaaggacat ttagcctttc cacctctgtc   1860
ccctcttatt tgtcccctcc tgtccagtgc tgcctcttgc agtgctggat atctggctgt   1920
gtggtctgaa cctccctcca ttcctctgta ttggtgcctc acctaaggct aagtatacct   1980
ccccccccac cccccaaccc ccccaactcc ccacccccac ccccccacccc ccacctcccc   2040
acccccctac cccctaccc ccctaccccc ctctggtctg ccctgcactg cactgttgcc   2100
atgggcagtg ctccaggcct gcttggtgtg gacatggtgg tgagccgtgg caaggaccag   2160
aatggatcac agatgatcgt tggccaacag gtggcagaag aggaattcct gccttcctca   2220
agaggaacac ctaccccttg gctaatgctg gggtcggatt ttgatttata tttatctttt   2280
ggatgtcagt catacagtct gattttgtgg tttgctagtg tttgaattta agtcttaagt   2340
gactattata gaaatgtatt aagaggcttt atttgtagaa ttcactttaa ttacatttaa   2400
tgagttttg ttttgagttc cttaaaattc cttaaagttt ttagcttctc attacaaatt   2460
ccttaacctt tttttggcag tagatagtca aagtcaaatc atttctaatg ttttaaaaat   2520
gtgctggtca ttttctttga aattgactta actattttcc tttgaagagt ctgtagcaca   2580
gaaacagtaa aaaatttaac ttcatgacct aatgtaaaaa agagtgtttg aaggtttaca   2640
caggtccagg ccttgctttg ttcccatcct tgatgctgca ctaattgact aatcacctac   2700
ttatcagaca ggaaacttga attgctgtgg tctggtgtcc tctattcaga cttattatat   2760
tggagtattt caatttttcg ttgtatcctg cctgcctagc atccagttcc tccccagccc   2820
tgctcccagc aaaccctag tctagcccca gccctactcc caccccgccc cagccctgcc   2880
ccagccccag tccctaacc ccccagccct agccccagtc ccagtcctag ttcctcagtc   2940
ccgcccagct tctctcgaaa gtcactctaa ttttcattga ttcagtgctc aaaataagtt   3000
gtccattgct tatcctatta tactgggata ttccgtttac ccttggcatt gctgatcttc   3060
agtactgact ccttgaccat tttcagttaa tgcatacaat cccatttgtc tgtgatctca   3120
ggacaaagaa tttccttact cggtacgttg aagttaggga atgtcaattg agagctttct   3180
atcagagcat tattgcccac aatttgagtt acttatcatt ttctcgatcc cctgccctta   3240
aaggagaaac catttctctg tcattgcttc tgtagtcaca gtcccaattt tgagtagtga   3300
tcttttcttg tgtactgtgt tggccaccta aaactctttg cattgagtaa aattctaatt   3360
gccaataatc ctaccattg gattagacag cactctgaac cccatttgca ttcagcaggg   3420
ggtcgcagac aacccgtctt ttgttggaca gttaaaatgc tcagtcccaa ttgtcatagc   3480
tttgcctatt aaacaaaggc accctactgc gcttttttgct gtgcttctgg agaatcctgc   3540
tgttcttgga caattaaaga acaaagtagt aattgctaat tgtctcaccc attaatcatg   3600
aagactacca gtcgcccttg catttgcctt gaggcagcgc tgactacctg agatttaaga   3660
gtttcttaaa ttattgagta aaatcccaat tatccatagt tctgttagtt acactatggc   3720
ctttgcaaac atctttgcat aacagcagtg ggactgactc attcttagag ccccttccct   3780
tggaatatta atggatacaa tagtaattat tcatggttct gcgtaacaga gaagacccac   3840
ttatgtgtat gcctttatca ttgctcctag atagtgtgaa ctacctacca ccttgcatta   3900
atatgtaaaa cactaattgc ccatagtccc actcattagt ctaggatgtc ctctttgcca   3960
ttgctgctga gttctgacta cccaagtttc cttctcttaa acagttgata tgcataattg   4020
```

```
catatattca tggttctgtg caataaaaat ggattctcac cccatcccac cttctgtggg    4080
atgttgctaa cgagtgcaga ttattcaata acagctcttg aacagttaat ttgcacagtt    4140
gcaattgtcc agagtcctgt ccattagaaa gggactctgt atcctatttg cacgctacaa    4200
tgtgggctga tcacccaagg actcttcttg tgcattgatg ttcataattg tatttgtcca    4260
cgatcttgtg cactaaccct tccactccct ttgtattcca gcaggggacc cttactactc    4320
aagacctctg tactaggaca gtttatgtgc acaatcctaa ttgattagaa ctgagtcttt    4380
tatatcaagg tccctgcatc atctttgctt tacatcaaga gggtgctggt tacctaatgc    4440
ccctcctcca gaaattattg atgtgcaaaa tgcaatttcc ctatctgctg ttagtctggg    4500
gtctcatccc ctcatattcc ttttgtctta cagcaggggg tacttgggac tgttaatgcg    4560
cataattgca attatggtct tttccattaa attaagatcc caactgctca cacccctctta   4620 gcattacagt agagggtgct aatcacaagg acatttcttt tgtactgtta atgtgctact    4680
tgcatttgtc cctcttcctg tgcactaaag accccactca cttccctagt gttcagcagt    4740
ggatgacctc tagtcaagac cttttgcacta ggatagttaa tgtgaaccat ggcaactgat   4800
cacaacaatg tctttcagat cagatccatt ttatcctcct tgttttacag caagggatat    4860
taattaccta tgttaccttt ccctgggact atgaatgtgc aaaattccaa tgttcatggt    4920
ctctcccttt aaacctatat tctacccctt ttacattata gaaagggatg ctggaaaccc    4980
agagtccttc tcttgggact cttaatgtgt atttctaatt atccatgact cttaatgtgc    5040
atattttcaa ttgcctaatt gatttcaatt gtctaagaca tttcaaatgt ctaattgatt    5100
agaactgagt cttttatatc aagctaatat ctagctttta tatcaagcta atatcttgac    5160
ttctcagcat catagaaggg ggtactgatt tcctaaagtc tttcttgaat ttctattatg    5220
caaaattgcc ctgaggccgg gtgtggtggc tcacacctgt aatcccagca ctttgggagg    5280
ctgaggtggg aagatccctt actgccagga gtttgagacc agcctggcca acattaaaaa    5340
aaaaaaaaag taagacaatt gccctggaat cccatccccc tcacacctcc ttggcaaagc    5400
agcaggagtg ctaactagct agtgcttctt ctcttatact gcttaaatgc gcataattag    5460
cagtagttga tgtgccccta tgttagagta gaatcccgct tccttgctcc atttgcatta    5520
ctgcaggagc ttctaactag cctgaattca ctctcttgga ctgttaatgt gcatacttat    5580
atttgctgct gtacttttttt accatgtaag gaccccaccc actgtattta catcccagct    5640
ggaagtacct actacttaag acccttagac tagtaaagtt agcgtgcata atcttaggtg    5700
ttatatacac attttcagtt gcatacagtt gtgccttta tcaggactcc tgtacttatc     5760
aaagcagaga gtgctaatca atattaagcc cttctcttcg aactgtagat ggcatgtaat    5820
tgcagttgtc aatggtcctt caattagact tgggtttctg acctatcaca ccctctttgc    5880
tttattgcat ggggtactat tcacttaagg cccctttctc aaactgttaa tgtgcctaat    5940
gacaattaca tcagtatcct tccttttgaa ggacagcatg gttggtgaca cctaaggccc    6000
catttcttgg cctcccaata tgtgtgattg tatttgtcga ggttgctatg cactagagaa    6060
ggaaagtgct cccctcatcc ccactttttcc cttccagcag gaagtgccca ccccataaga   6120
cccttttatt tggagagtct aggtgcacaa ttgtaagtga ccacaagcat gcatcttgga    6180
catttatgtg cgtaatcgca cactgctcat tccatgtgaa taaggtccta ctctccgacc    6240 cctttttgcaa tacagaaggg ttgctgataa cgcagtcccc ttttcttggc atgttgtgtg   6300
tgattataat cgtctgggat cctatgcact agaaaaggag ggtcctctcc acatacctca    6360
gtctcacctt tcccttccag cagggagtgc ccactccata agactctcac atttggacag    6420
```

```
tcaaggtgcg taattgttaa gtgaacacaa ccatgcacct tagacatgga tttgcataac    6480
tacacacagc tcaacctatc tgaataaaat cctactctca gaccccttttt gcagtacagc    6540 aggggtgctg atcaccaagg cccttttttcc tggcctggta tgcgtgtgat tatgtttgtc    6600
ccggttcctg tgtattagac atggaagcct ccccctgccac actccacccc caatcttcct    6660
ttcccttccg gcagggagtg ccctctccat aagacgctta cgtttggaca atcaaggtgc    6720
acagttgtaa gtgaccacag gcatacacct tggacattaa tgtgcataac cactttgccc    6780
attccatctg aataaggtcc tactctcaga cccctttttgc agtacagcag gggtgctgat    6840
caccaaggcc ccttttcttg gcctgttatg tgcgtgatta tatttgtctg ggttcctgtg    6900
tattagacaa ggaagccttc cccccgcccc cacccccact cccagtcttc ctttcccttc    6960
cagcagggag tgccccctcc ataagatcat tacatttgga caatcaaggt gcacaattat    7020
aagtgaccac agccatgcac cttggacatt attggacatt aatgtgcgta actgcacatg    7080
gcccatccca tctgaataag gtcctactct cagatgccct ttgcagtaca gcagggggtac    7140 tgaatcacca aggccccttttt tcttggcctg ttatgtgtgt gattatattt atcccagttt    7200
ctgtgtaata gacatgaaag cctcccctgc cacacccccac ctccaatctt cctttccctt    7260
ccaccaggga gtgtccactc catatacccct tacatttgga caatcaaggt gcacaattgt    7320
aagtgagcat aggcactcac cttggacatg aatgtgcata actgcacatg gcccatccca    7380
tctgaataag gtcctactct cagaccccttt ttgcagtaca gcagggggtgc tgatcaccaa    7440 ggccccttttt cctggcctgt tatgtgtgtg attatatttg ttccagttcc tgtgtaatag    7500
acatggaagc ctcccctgcc acactccacc cccaatcttc ctttcccttc tggcaggaag    7560
tacccgctcc ataagaccct tacatttgga cagtcaaggt gcacaattgt atgtgaccac    7620
aaccatgcac cttggacata aatgtgtgta actgcacatg gcccatccca tctgaataag    7680
gtcctactct cagacccctt ttgcagtaca gtaggtgtgc tgataaccaa ggcccctctt    7740
cctggcctgt taacgtatgt gattatatttt gtctgggttc cagtgtataa gacatggaag    7800
cctcccctgc cccacccccac cctcaatctt cctttccctt ctggcaggga gtgccagctc    7860
cataagaacc ttacatttgg acagtcaagg tgcacaattc taagtgaccg cagccatgca    7920
ccttggtcaa taatgtgtgt aactgcacac ggcctatctc atctgaataa ggccttactc    7980
tcagacccct tttgcagtac agcaggggtg ctgataacca aggcccatttt tcctggcctg    8040 ttatgtgtgt gattatatttt gtccaggttt ctgtgtacta gacaaggaag cctcctctgc    8100
cccatcccat ctacgcataa tctttctttt cctcccagca gggagtgctc actccataag    8160
acccttacat ttggacaatc aaggtgcaca attgtaagtg accacaacca tgcatcttgg    8220
aaatttatgt gcataactgc acatggctta tcctatttga ataaagtcct actctcagac    8280 ccccttttgca gtatagctgg ggtgctgatc actgaggcct ctttgcttgg cttgtctata    8340
ttcttgtgta ctagataagg gcaccttctc atggactccc tttgcttttc aacaaggagt    8400
acccactact tttttaagatt cttatatttg tccaaagtac atggttttaa ttgaccacaa    8460
caatgtccct tggacattaa tgtatgtaat caccacatgg ttcatcctaa ttaaacaaag    8520
ttctaccttc tcaccctcca tttgcagtat accagggttg ctgacccccct aagtccccctt    8580 ttcttggctt gttgacatgc ataattgcat ttatgttggt tcttgtgccc tagacaagga    8640
tgccccacct cttttcaata gtgggtgccc actcccttatg atctttacat ttgaacagtt    8700
aatgtgaata attgcagttg tccacaaccc tatcacttct aggaccatta tacctctttt    8760
```

-continued

```
gcattactgt ggggtatact gtttccctcc aaggcccctt ctggtggact atcaacatat    8820
aattgaaatt ttcttttgtc tttgtcagta gattaaggtc ataccccatc accttttcctt   8880 tgtagtacaa cagggtgtcc tgatcaacca aagtcctgtt gttttggact gttaatatgt    8940
gcaattacat ttgctcctga tctgtgcact agataaggat cctacctact ttcttagtgt    9000
ttttagcagg tagtgcccac tactcaagac tgtcacttgg aatgttcatg tgcacaaact    9060
caattctcta agcatgttcc tgtaccacct ttgctttaga gcaggggat gatattcact     9120 aagtgcccct tcttttggac ttaatatgca ttaatgcaat tgtccacctc ttcttttaga    9180
ctaagagttg atctccacat attcccttg catcaggggc atgttaatta tgaatgaacc     9240
cttttctttt aatattaatg tcataattgt atttgtggac ctgtgtagga gaaaaagacc    9300
ctatgttcct cccattaccc tttggattgc tgctgagaag tgttaactac tcataatctc    9360
agctcttgga caattaatag cattaataac aattatcaag ggcactgatc attagataag    9420
actcctgctt cctcgttgct tacatcgggg gtactgaccc actaaggccc cttgtactgt    9480
taatgtgaat atttgcaatt atatatgtct ccttctggta gagtgggata ttatgcccta    9540 gtatccctt tgcattactg caggggctgc tgactactca aaacttctcc tgggactgtt    9600
aataggcaca atggcagtta tcaatggttt tctccctccc tgaccttgtt aagcaagcgc    9660
cccaccccac ccttagtttc ccatggcata ataaagtata agcattggag tattccatgc    9720
acttgtctat caaacagtgg tccatactcc caaccctttt gcattgcgcc agtgtgtaaa    9780
atcacaggta gccatggtgt catgctttat atacgaagtc ttccctctct ctgccccttg    9840
tgtgcccttg gcccctttt acagactatt gctcacaatc tcaggtgtcc atatttgcag    9900
ctattaggta agattgtgct gtctccctct tcccttccct ctgccctgcc cctttttgcct   9960 ctttgctggg taatgttgac cagacaaggc cctttctctt ggacttaaac aattctcagt   10020
tgcactttcc ttggtcccac ccattataca tgaaccctc tacttccttt cgcattgctt    10080
ctgagtatgc tgactaccca aagcccttc tgtgttatta ataaacacag tactgattgt     10140 cccattttc agcccatcag tccaagatct ccctaccact ttggtgtgtt ggtgcagtgt    10200
tgactatgaa aagcaggcct gaactaggtg gataagcctt cactcatttt ctttcattta   10260
ttaatgatcc tagtttcaat tattgtcaga ttctggggac aagaaccatt cttgcccacc    10320
tgtgttactg ctttactgtg caaaatactg aaggcaagtc agacccaggg agctggattg    10380
ccatccttta ttttgtgttt ccagtgtaca ctataaaatt gtctcccag gaaggaaggt    10440 tggcactttc tctgcattct tctttccaga gcagattgcc tggttaagaa tctcttgttg    10500 tccccttttgt atattgttat tgtaaagtgc caaatgccag gatacagcca gaaaaattgc    10560
ttattattat taaaaaaatt ttttaagaa agacatctgg attgtagggt ggactcgata    10620
acctggtcat tattttttg aagccaaaat atccatttat actatgtacc tggtgaccag    10680
tgtctctcat tttaactgag ggtggtgggt ctgtggatag aacactgact cttgctattt    10740
taatatcaaa gatattctag agtggaactc ttaagaccag tatctttgtg tgggctttac    10800
cagcattcac ttttagaaaa actacctaaa ttttataatc ctttaatttc ttcatctgga   10860
gcacctgccc ctacttattt caagaagatt gcagtaaaac gattaaatga gggaacatat    10920
gcagaggtgc ttttaaaaag catatgccac ctttttttatt aattattata taaaatgaag    10980
catttaatta tagtaataat ttgaagtagt ttgaagtacc acactgaggt gaggacttaa    11040
aaatgataag acgagttccc tatttttataa gaaaaataag ccaaaattaa atattctttt    11100
ggatataaat ttcaacagtg agatagctgc ctagtggaaa tgaataatat cccagccact    11160
```

-continued

```
agtgtacagg gtgttttgtg gcacaggatt atgtaatatg gaactgctca agcaaataac   11220
tagtcatcac aacagcagtt ctttgtaata actgaaaaag aatattgttt ctcggagaag   11280
gatgtcaaaa gatcggccca gctcaggag cagtttgccc tactagctcc tcggacagct    11340
gtaaagaaga gtctctggct ctttagaata ctgatcccat tgaagatacc acgctgcatg   11400
tgtccttagt agtcatgtct ccttaggctc ctcttggaca ttctgagcat gtgagacctg   11460
aggactgcaa acagctataa gaggctccaa attaatcata tctttccctt tgagaatctg   11520
gccaagctcc agctaatcta cttggatggg ttgccagcta tctggagaaa aagatcttcc   11580
tcagaagaat aggcttgttg ttttacagtg ttagtgatcc attcccttttg acgatcccta  11640 ggtggagatg gggcatgagg atcctccagg ggaaaagctc actaccactg gcaacaacc    11700 ctaggtcagg aggttctgtc aagatacttt cctggtccca gataggaaga taaagtctca   11760
aaaacaacca ccacacgtca agctcttcat tgttcctatc tgccaaatca ttatacttcc   11820
tacaagcagt gcagagagct gagtcttcag caggtccaag aaatttgaac acactgaagg   11880
aagtcagcct tcccacctga agatcaacat gcctggcact ctagcacttg aggatagctg   11940
aatgaatgtg tatttctttg tctctttctt tcttgtcttt gctctttgtt ctctatctaa   12000
agtgtgtctt acccatttcc atgtttctct tgctaatttc tttcgtgtgt gcctttgcct   12060 catttctct ttttgttcac aagagtggtc tgtgtcttgt cttagacata tctctcattt    12120
ttcattttgt tgctatttct ctttgctctc ctagatgtgg ctcttctttc acgctttatt   12180
tcatgtctcc ttttttgggtc acatgctgtg tgcttttgt cctttttcttg ttctgtctac  12240 ctctcctttc tctgcctacc tctctttttct ctttgtgaac tgtgattatt tgttacccct  12300
tccccttctc gttcgtttta aatttcacct ttttttctgag tctggcctcc tttctgctgt  12360 ttctacttttt tatctcacat ttctcatttc tgcatttcct ttctgcctct cttgggctat   12420
tctctctctc ctccccctgcg tgcctcagca tctcttgctg tttgtgattt tctatttcag   12480
tattaatctc tgttggcttg tatttgttct ctgcttcttc cctttctact cacctttgag   12540
tatttcagcc tcttcatgaa tctatctccc tctctttgat ttcatgtaat ctctccttaa   12600
atatttcttt gcatatgtgg gcaagtgtac gtgtgtgtgt gtcatgtgtg gcagaggggc   12660
ttcctaaccc ctgcctgata ggtgcagaac gtcggctatc agagcaagca ttgtggagcg   12720
gttccttatg ccaggctgcc atgtgagatg atccaagacc aaaacaaggc cctagactgc   12780
agtaaaaccc agaactcaag tagggcagaa ggtggaaggc tcatatggat agaaggccca   12840
aagtataaga cagatggttt gagacttgag acccgaggac taagatggaa agcccatgtt   12900
ccaagataga tagaagcctc aggcctgaaa ccaacaaaag cctcaagagc caagaaaaca   12960
gagggtggcc tgaattggac cgaaggcctg agttggatgg aagtctcaag gcttgagtta   13020
gaagtcttaa gacctgggac aggacacatg gaaggcctaa gaactgagac ttgtgacaca   13080
aggccaacga cctaagatta gcccagggtt gtagctggaa gacctacaac ccaaggatgg   13140
aaggcccctg tcacaaagcc tacctagatg gatagaggac ccaagcgaaa aaggtatctc   13200
aagactaacg gccggaatct ggaggcccat gacccagaac ccaggaagga tagaagcttg   13260
aagacctggg gaaatcccaa gatgagaacc ctaaacccta cctctttttct attgtttaca   13320 cttcttactc ttagatattt ccagttctcc tgtttatctt taagcctgat tcttttgaga   13380 tgtactttttt gatgttgccg gttaccttta gattgacagt attatgcctg gccagtctt   13440 gagccagctt taaatcacag cttttaccta tttgttaggc tatagtgttt tgtaaacttc   13500
```

```
tgtttctatt cacatcttct ccacttgaga gagacaccaa aatccagtca gtatctaatc    13560
tggcttttgt taacttccct caggagcaga cattcatata ggtgatactg tatttcagtc    13620
cttctttttg accccagaag ccctagactg agaagataaa atggtcaggt tgttggggaa    13680
aaaaaagtgc caggctctct agagaaaaat gtgaagagat gctccaggcc aatgagaaga    13740
attagacaag aaatacacag atgtgccaga cttctgagaa gcacctgcca gcaacagctt    13800
ccttctttga gcttaggtga gcaggattct ggggtttggg atttctagtg atggttatgg    13860
aaagggtgac tgtgcctggg acaaagcgag gtcccaaggg gacagcctga actccctgct    13920
catagtagtg gccaaataat ttggtggact gtgccaacgc tactcctggg tttaataccc    13980
atctctaggc ttaaagatga gagaacctgg gactgttgag catgtttaat actttccttg    14040 attttttttct tcctgtttat gtgggaagtt gatttaaatg actgataatg tgtatgaaag    14100
cactgtaaaa cataagagaa aaaccaatta gtgtattggc aatcatgcag ttaacatttg    14160
aaagtgcagt gtaaattgtg aagcattatg taaatcaggg gtccacagtt tttctgtaag    14220
gggtcaaatc ataaatactt tagactgtgg gccatatggt ttctgttaca tatttgtttt    14280
ttaaacaacg tttttataag gtcaaaatca ttcttagttt ttgagccaat tggatttggc    14340
ctgctgttca tagcttacca cccccctgatg tattatttgt tattcagaga aaatttctga    14400
atactactag tttccttttc tgtgcctgtc cctgtgctag gcactaaaaa tgcaatgatt    14460
attgatatct aggtgacctg aaaaaaaata gtgaatgtgc tttgtaaact gtaaagcact    14520
tgtattctac tgtgataagc gttgtggata caaagaaagg agcaagcata aaaaagtgct    14580 cttttcaaaag gatatagtac tatgcagaca caaggaattg tttgataaat gaataaatta    14640
tatgtatatt tgaggccaat ttgtgtttgc tgctctggta attttgagta aaaatgcagt    14700
attccaggta tcagaaacga aaacacatgg aaactgcttt taaactttaa aatatactga    14760
aaacataagg gactaagctt gttgtggtca cctataatgt gccagatacc atgctgggtg    14820
ctagagctac caaaggggga aaagtattct catagaacaa aaaatttcag aaaggtgcat    14880
attaaagtgc tttgtaaact aaagcatgat acaaatgtca atgggctaca tatttatgaa    14940
tgaatgaatg gatgaatgaa tattaagtgc ctcttacata ccagctattt tgggtactgt    15000
aaaatacaag attaattctc ctatgtaata agaggaaagt ttatcctcta tactattcag    15060
atgtaaggaa tgatatattg cttaattta aacaatcaag actttactgg tgaggttaag    15120
ttaaattatt actgatacat ttttccaggt aaccaggaaa gagctagtat gaggaaatga    15180
agtaatagat gtgagatcca gaccgaaagt cacttaattc agcttgcgaa tgtgctttct    15240
aaattataaa gcacttgtaa atgaaaaatt tgatgctttc tgtatgaata aactttctg    15300 taagctaggt attgtctcta caaaattctc attgtatagt taaaccacag tgagaagggt    15360
tctataagta gttatacaaa ccaagggttt aaatacctgt taaatagatc aattttgatt    15420
gcctactatg tgaactcact gttaaaggca ctgaaaattt atcatatttc atttagccac    15480
agccaaaaat aaggcaatac ctatgttagc attttgtgaa ctctaaggca ccatataaat    15540
gtaactgttg attttctcac ttggtgctgg gtactaggtt tataaaattg tatgatagtt    15600
attatattgt gcaaataaag taggaaaatt tgaataacaa tgattatctt ttgaatacgc    15660
atacgcaagg gattggttgt ctgaagaatg ccactatagt agttatctat tgtgtgccaa    15720
tctcattgct aggcattggg gatgcaaaga taaaccatct ttattgtgtc ttgggtagca    15780
gaagaaaata tgtgtaaaat caattttaaa tttgtaaact gccacccata tataagctat    15840
atctgctgaa tgatcattga ttactcttat ccttagagat aacaactggg ggcacaaaca    15900
```

```
tttattatca ttattgaacc tacaacagag atctatgtgt agatttacaa agcctacagt    15960
tctatacaga taggaatgaa ctattggctt actgaatggt gattactttc tgtggggctc    16020
ggaactacat gccctaggat ataaaaatga tgttatcatt atagagtgct cacagaagga    16080
aatgaagtaa tataggtgtg agatccagac caaaagtcat ttaacaagtt tattcagtga    16140
tgaaaacatg ggacaaatgg actaatataa ggcagtgtac taagctgagt agagagataa    16200
agtcctgtcc agaagataca tgcttcctgg cctgattgag gagatggaaa attttgcaa     16260 aaaacaaggt gttgtggtct tccatccagt ttcttaagtg ctgatgataa aagtgaatta    16320
gacccacctt gacctggcct acagaagtaa aggagtaaaa ataaatgcct caggcgtgct    16380
ttttgattca tttgataaac aaagcatctt ttatgtggaa tataccattc tgggtcctga    16440
ggataagaga gatgagggca ttagatcact gacagctgaa gatagaagaa catctttggt    16500
ttgattgttt aaataatatt tcaatgccta ttctctgcaa ggtactatgt ttcgtaaatt    16560
aaataggtct ggcccagaag acccactcaa ttgccttcga gattaaaaaa aaaaaaaaaa    16620
agaaagaaaa atgcaagttt cttcaaaat  aaagagacat ttttcctagt ttcaggaatc    16680
ccccaaatca cttcctcatt ggcttagttt aaagccagga gactgataaa agggctcagg    16740
gtttgttctt taattcatta actaaacatt ctgcttttat tacagttaaa tggttcaaga    16800
tgtaacaact agttttaaag gtatttgctc attggtctgg cttagagaca ggaagacata    16860
tgagcaataa aaaaaagatt cttttgcatt taccaattta gtaaaaattt attaaaactg    16920
aataaagtgc tgttcttaag tgcttgaaag acgtaaacca aagtgcactt tatctcattt    16980
atcttatggt ggaaacacag gaacaaattc tctaagagac tgtgtttctt tagttgagaa    17040
gaaacttcat tgagtagctg tgatatgttc gatactaagg aaaaactaaa cagatcacct    17100
ttgacatgcg ttgtagagtg ggaataagag agggcttttt attttttcgt tcatcgagt     17160 attgatgaag atgatactaa atgctaaatg aaatatatct gctccaaaag gcatttattc    17220
tgacttggag atgcaacaaa aacacaaaaa tggaatgaag tgatactctt catcaaacag    17280
aagtgactgt tatctcaacc attttgttaa atcctaaaca gaaaacaaaa aaatcatga    17340 cgaaaagaca cttgcttatt aattggcttg gaaagtagaa tataggagaa aggttactgt    17400
ttattttttt tcatgtattc attcattcta caaatatatt cgggtgccaa taggtacttg    17460
gtataaggtt tttggcccca gagacatggg aaaaaaatgc atgccttccc agagaatgcc    17520
taatactttc cttttggctt gttttcttgt taggggcatg gcttagtccc taaataacat    17580
tgtgtggttt aattcctact ccgtatctct tctaccactc tggccactac gataagcagg    17640
tagctgggtt ttgtagtgag cttgctcctt aagttacagg aactctcctt ataatagaca    17700
cttcattttc ctagtccatc cctcatgaaa aatgactgac cactgctggg cagcaggagg    17760
gatgatgacc aactaattcc caaacccag  tctcattggt accagccttg ggaaccacc     17820 tacacttgag ccacaattgg ttttgaagtg catttacaag gtttgtctat ttcagttct     17880 ttacttttta catgctgaca catacataca ctgcctaaat agatctcttt cagaaacaat    17940
cctcagataa cgcatagcaa aatggagatg gagacatgat ttctcatgca acagcttctc    18000
taattatacc ttagaaatgt tctccttttt atcatcaaat ctgctcaaga agggcttttt    18060
atagtagaat aatatcagtg gatgaaaaca gcttaacatt ttaccatgct taagttttaa    18120
gaataaaata aaaattggaa ataattggcc aaaattgaaa ggaaaatttt ttttaaaatt    18180
tctctaaatg taggcctggc tgggctttga ccttttccgt ttttaaatca ctcacagagg    18240
```

-continued

```
gtgggacagg aggaagagtg aaggaaaagg tcaaacctgt tttaagggca acctgccttt    18300
gttctgaatt ggtcttaaga acattaccag ctccaggttt aaattgttca gtttcatgca    18360
gttccaatag ctgatcattg ttgagatgag acaaaatcc tttgtcctca ctagtttgct     18420
ttacattttt gaaaagtatt attttttgtcc aagtgcttat caactaaacc ttgtgttagg   18480
taagaatgga atttattaag tgaatcagtg tgacccttct tgtcataaga ttatcttaaa    18540
gctgaagcca aaatatgctt caaaagaaga ggactttatt gttcattgta gttcatacat    18600
tcaaagcatc tgaactgtag tttctatagc aagccaatta catccataag tggagaagga    18660
aatagataaa tgtcaaagta tgattggtgg agggagcaag gttgaagata atctgggtt     18720 gaaattttct agttttcatt ctgtacattt ttagttagac atcagatttg aaatattaat    18780
gtttaccttt caatgtgtgg tatcagctgg actcagtaac accccttcct tcagctgggg    18840
atggggaatg gattattgga aaatggaaag aagaaagtaa ctaaaagcct tccttcaca    18900 gtttctggca tcactaccac tactgattaa acaagaataa gagaacattt tatcatcatc    18960
tgctttattc acataaatga agttgtgatg aataaatctg cttttatgca gacacaagga    19020
attaagtggc ttcgtcattg tccttctacc tcaaagataa tttattccaa aagctaagat   19080
aaatggaaga ctcttgaact tgtgaactga tgtgaaatgc agaatctctt ttgagtcttt    19140
gctgtttgga agattgaaaa atattgttca gcatgggtga ccaccagaaa gtaatcttaa    19200
gccatctaga tgtcacaatt gaaacaaact ggggagttgg ttgctattgt aaaataaaat    19260
atactgtttt g                                                         19271
```

<210> SEQ ID NO 14
<211> LENGTH: 10241
<212> TYPE: DNA
<213> ORGANISM: Homo sapiens
<220> FEATURE:
<221> NAME/KEY: CDS
<222> LOCATION: (227)..(1687)

<400> SEQUENCE: 14

```
ccggcgtcgg cggcgcgcgc gctccctcct ctcggagaga gggctgtggt aaaagccgtc    60
cggaaaatgg ccgccgccgc cgccgccgcg ccgagcggga gaggaggagg aggcgaggag    120
gagagactgc tccataaaaa tacagactca ccagttcctg ctttgatgtg acatgtgact    180
ccccagaata caccttgctt ctgtagacca gctccaacag gattcc atg gta gct       235
                                                   Met Val Ala
                                                     1
```

```
ggg atg tta ggg ctc agg gaa gaa aag tca gaa gac cag gac ctc cag    283
Gly Met Leu Gly Leu Arg Glu Glu Lys Ser Glu Asp Gln Asp Leu Gln
  5                  10                  15 ggc ctc aag gac aaa ccc ctc aag ttt aaa aag gtg aag aaa gat aag    331
Gly Leu Lys Asp Lys Pro Leu Lys Phe Lys Lys Val Lys Lys Asp Lys
 20                  25                  30                  35 aaa gaa gag aaa gag ggc aag cat gag ccc gtg cag cca tca gcc cac    379
Lys Glu Glu Lys Glu Gly Lys His Glu Pro Val Gln Pro Ser Ala His
                 40                  45                  50 cac tct gct gag ccc gca gag gca ggc aaa gca gag aca tca gaa ggg    427
His Ser Ala Glu Pro Ala Glu Ala Gly Lys Ala Glu Thr Ser Glu Gly
             55                  60                  65 tca ggc tcc gcc ccg gct gtg ccg gaa gct tct gcc tcc ccc aaa cag    475
Ser Gly Ser Ala Pro Ala Val Pro Glu Ala Ser Ala Ser Pro Lys Gln
     70                  75                  80 cgg cgc tcc atc atc cgt gac cgg gga ccc atg tat gat gac ccc acc    523
Arg Arg Ser Ile Ile Arg Asp Arg Gly Pro Met Tyr Asp Asp Pro Thr
```

-continued

|  |  |  |  |  |  |  |  |  |  |  |  |  |  |  |  |  |
|---|---|---|---|---|---|---|---|---|---|---|---|---|---|---|---|---|
|  |  | 85 |  |  |  | 90 |  |  |  | 95 |  |  |  |  |  |  |

```
ctg cct gaa ggc tgg aca cgg aag ctt aag caa agg aaa tct ggc cgc      571
Leu Pro Glu Gly Trp Thr Arg Lys Leu Lys Gln Arg Lys Ser Gly Arg
100             105                 110                 115 tct gct ggg aag tat gat gtg tat ttg atc aat ccc cag gga aaa gcc      619
Ser Ala Gly Lys Tyr Asp Val Tyr Leu Ile Asn Pro Gln Gly Lys Ala
                120                 125                 130 ttt cgc tct aaa gtg gag ttg att gcg tac ttc gaa aag gta ggc gac      667
Phe Arg Ser Lys Val Glu Leu Ile Ala Tyr Phe Glu Lys Val Gly Asp
            135                 140                 145 aca tcc ctg gac cct aat gat ttt gac ttc acg gta act ggg aga ggg      715
Thr Ser Leu Asp Pro Asn Asp Phe Asp Phe Thr Val Thr Gly Arg Gly
        150                 155                 160 agc ccc tcc cgg cga gag cag aaa cca cct aag aag ccc aaa tct ccc      763
Ser Pro Ser Arg Arg Glu Gln Lys Pro Pro Lys Lys Pro Lys Ser Pro
    165                 170                 175 aaa gct cca gga act ggc aga ggc cgg gga cgc ccc aaa ggg agc ggc      811
Lys Ala Pro Gly Thr Gly Arg Gly Arg Gly Arg Pro Lys Gly Ser Gly
180                 185                 190                 195 acc acg aga ccc aag gcg gcc acg tca gag ggt gtg cag gtg aaa agg      859
Thr Thr Arg Pro Lys Ala Ala Thr Ser Glu Gly Val Gln Val Lys Arg
                200                 205                 210 gtc ctg gag aaa agt cct ggg aag ctc ctt gtc aag atg cct ttt caa      907
Val Leu Glu Lys Ser Pro Gly Lys Leu Leu Val Lys Met Pro Phe Gln
            215                 220                 225 act tcg cca ggg ggc aag gct gag ggg ggt ggg gcc acc aca tcc acc      955
Thr Ser Pro Gly Gly Lys Ala Glu Gly Gly Gly Ala Thr Thr Ser Thr
        230                 235                 240 cag gtc atg gtg atc aaa cgc ccc ggc agg aag cga aaa gct gag gcc     1003
Gln Val Met Val Ile Lys Arg Pro Gly Arg Lys Arg Lys Ala Glu Ala
    245                 250                 255 gac cct cag gcc att ccc aag aaa cgg ggc cga aag ccg ggg agt gtg     1051
Asp Pro Gln Ala Ile Pro Lys Lys Arg Gly Arg Lys Pro Gly Ser Val
260                 265                 270                 275 gtg gca gcc gct gcc gcc gag gcc aaa aag aaa gcc gtg aag gag tct     1099
Val Ala Ala Ala Ala Ala Glu Ala Lys Lys Lys Ala Val Lys Glu Ser
                280                 285                 290 tct atc cga tct gtg cag gag acc gta ctc ccc atc aag aag cgc aag     1147
Ser Ile Arg Ser Val Gln Glu Thr Val Leu Pro Ile Lys Lys Arg Lys
            295                 300                 305 acc cgg gag acg gtc agc atc gag gtc aag gaa gtg gtg aag ccc ctg     1195
Thr Arg Glu Thr Val Ser Ile Glu Val Lys Glu Val Val Lys Pro Leu
        310                 315                 320 ctg gtg tcc acc ctc ggt gag aag agc ggg aaa gga ctg aag acc tgt     1243
Leu Val Ser Thr Leu Gly Glu Lys Ser Gly Lys Gly Leu Lys Thr Cys
    325                 330                 335 aag agc cct ggg cgg aaa agc aag gag agc agc ccc aag ggg cgc agc     1291
Lys Ser Pro Gly Arg Lys Ser Lys Glu Ser Ser Pro Lys Gly Arg Ser
340                 345                 350                 355 agc agc gcc tcc tca ccc ccc aag aag gag cac cac cac cat cac cac     1339
Ser Ser Ala Ser Ser Pro Pro Lys Lys Glu His His His His His His
                360                 365                 370 cac tca gag tcc cca aag gcc ccc gtg cca ctg ctc cca ccc ctg ccc     1387
His Ser Glu Ser Pro Lys Ala Pro Val Pro Leu Leu Pro Pro Leu Pro
            375                 380                 385 cca cct cca cct gag ccc gag agc tcc gag gac ccc acc agc ccc cct     1435
Pro Pro Pro Pro Glu Pro Glu Ser Ser Glu Asp Pro Thr Ser Pro Pro
        390                 395                 400 gag ccc cag gac ttg agc agc agc gtc tgc aaa gag gag aag atg ccc     1483
```

-continued

| | | |
|---|---|---|
| Glu Pro Gln Asp Leu Ser Ser Ser Val Cys Lys Glu Lys Met Pro<br>405                  410                  415 | | |
| aga gga ggc tca ctg gag agc gac ggc tgc ccc aag gag cca gct aag<br>Arg Gly Gly Ser Leu Glu Ser Asp Gly Cys Pro Lys Glu Pro Ala Lys<br>420                  425                  430                  435 | 1531 | |
| act cag ccc gcg gtt gcc acc gcc gcc acg gcc gca gaa aag tac aaa<br>Thr Gln Pro Ala Val Ala Thr Ala Ala Thr Ala Ala Glu Lys Tyr Lys<br>                  440                  445                  450 | 1579 | |
| cac cga ggg gag gga gag cgc aaa gac att gtt tca tcc tcc atg cca<br>His Arg Gly Glu Gly Glu Arg Lys Asp Ile Val Ser Ser Ser Met Pro<br>            455                  460                  465 | 1627 | |
| agg cca aac aga gag gag cct gtg gac agc cgg acg ccc gtg acc gag<br>Arg Pro Asn Arg Glu Glu Pro Val Asp Ser Arg Thr Pro Val Thr Glu<br>                  470                  475                  480 | 1675 | |
| aga gtt agc tga ctttacacgg agcggattgc aaagcaaacc aacaagaata<br>Arg Val Ser<br>    485 | 1727 | |
| aaggcagctg ttgtctcttc tccttatggg tagggctctg acaaagcttc ccgattaact | 1787 | |
| gaaataaaaa atattttttt ttctttcagt aaacttagag tttcgtggct tcagggtggg | 1847 | |
| agtagttgga gcattgggga tgttttcctt accgacaagc acagtcaggt tgaagaccta | 1907 | |
| accagggcca gaagtagctt tgcactttc taaactaggc tccttcaaca aggcttgctg | 1967 | |
| cagatactac tgaccagaca agctgttgac caggcacctc ccctcccgcc caaacctttc | 2027 | |
| ccccatgtgg tcgttagaga cagagcgaca gagcagttga gaggacactc ccgttttcgg | 2087 | |
| tgccatcagt gccccgtcta cagctccccc agctccccc acctccccca ctcccaacca | 2147 | |
| cgttgggaca gggaggtgtg aggcaggaga gacagttgga ttctttagag aagatggata | 2207 | |
| tgaccagtgg ctatgcctg tgcgatccca cccgtggtgg ctcaagtctg ccccacacc | 2267 | |
| agccccaatc caaaactggc aaggacgctt cacaggacag gaaagtggca cctgtctgct | 2327 | |
| ccagctctgg catggctagg aggggggagt cccttgaact actgggtgta gactggcctg | 2387 | |
| aaccacagga gaggatggcc cagggtgagg tggcatggtc cattctcaag ggacgtcctc | 2447 | |
| caacgggtgg cgctagaggc catggaggca gtaggacaag gtgcaggcag gctggcctgg | 2507 | |
| ggtcaggccg gcagagcac agcggggtga gagggattcc taatcactca gagcagtctg | 2567 | |
| tgacttagtg gacaggggag ggggcaaagg gggaggagaa gaaaatgttc ttccagttac | 2627 | |
| tttccaattc tcctttaggg acagcttaga attatttgca ctattgagtc ttcatgttcc | 2687 | |
| cacttcaaaa caaacagatg ctctgagagc aaactggctt gaattggtga catttagtcc | 2747 | |
| ctcaagccac cagatgtgac agtgttgaga actacctgga tttgtatata tacctgcgct | 2807 | |
| tgttttaaag tgggctcagc acatagggtt cccacgaagc tccgaaactc taagtgtttg | 2867 | |
| ctgcaatttt ataaggactt cctgattggt ttctcttctc cccttccatt tctgcctttt | 2927 | |
| gttcatttca tcctttcact tctttccctt cctccgtcct cctccttcct agttcatccc | 2987 | |
| ttctcttcca ggcagccgcg gtgcccaacc acacttgtcg gctccagtcc cagaactct | 3047 | |
| gcctgccctt tgtcctcctg ctgccagtac cagccccacc ctgttttgag ccctgaggag | 3107 | |
| gccttgggct ctgctgagtc cgacctggcc tgtctgtgaa gagcaagaga gcagcaaggt | 3167 | |
| cttgctctcc taggtagccc cctcttccct ggtaagaaaa agcaaaaggc atttcccacc | 3227 | |
| ctgaacaacg agccttttca cccttctact ctagagaagt ggactggagg agctgggccc | 3287 | |
| gatttggtag ttgaggaaag cacagaggcc tcctgtggcc tgccagtcat cgagtggccc | 3347 | |
| aacaggggct ccatgccagc cgaccttgac ctcactcaga agtccagagt ctagcgtagt | 3407 | |

```
gcagcagggc agtagcggta ccaatgcaga actcccaaga cccgagctgg gaccagtacc    3467
tgggtcccca gcccttcctc tgctcccccct tttccctcgg agttcttctt gaatggcaat    3527
gttttgcttt tgctcgatgc agacaggggg ccagaacacc acacatttca ctgtctgtct    3587
ggtccatagc tgtggtgtag gggcttagag gcatgggctt gctgtgggtt tttaattgat    3647
cagttttcat gtgggatccc atctttttaa cctctgttca ggaagtcctt atctagctgc    3707
atatcttcat catattggta tatccttttc tgtgtttaca gagatgtctc ttatatctaa    3767
atctgtccaa ctgagaagta ccttatcaaa gtagcaaatg agacagcagt cttatgcttc    3827
cagaaacacc cacaggcatg tcccatgtga gctgctgcca tgaactgtca agtgtgtgtt    3887
gtcttgtgta tttcagttat tgtccctggc ttccttacta tggtgtaatc atgaaggagt    3947
gaaacatcat agaaactgtc tagcacttcc ttgccagtct ttagtgatca ggaaccatag    4007
ttgacagttc caatcagtag cttaagaaaa aaccgtgttt gtctcttctg gaatggttag    4067
aagtgaggga gtttgccccg ttctgttttgt agagtctcat agttggactt tctagcatat    4127
atgtgtccat ttccttatgc tgtaaaagca agtcctgcaa ccaaactccc atcagcccaa    4187
tccctgatcc ctgatccctt ccacctgctc tgctgatgac ccccccagct tcacttctga    4247
ctcttcccca ggaagggaag gggggtcaga agagagggtg agtcctccag aactcttcct    4307
ccaaggacag aaggctcctg cccccatagt ggcctcgaac tcctggcact accaaaggac    4367
acttatccac gagagcgcag catccgacca ggttgtcact gagaagatgt ttattttggt    4427
cagttgggtt tttatgtatt atacttagtc aaatgtaatg tggcttctgg aatcattgtc    4487
cagagctgct tccccgtcac ctgggcgtca tctggtcctg gtaagaggag tgcgtggccc    4547
accaggcccc cctgtcaccc atgacagttc attcagggcc gatggggcag tcgtggttgg    4607
gaacacagca tttcaagcgt cactttattt cattcgggcc ccacctgcag ctccctcaaa    4667
gaggcagttg cccagcctct ttcccttcca gtttattcca gagctgccag tggggcctga    4727
ggctccttag ggttttctct ctatttcccc cttttcttcct cattccctcg tctttcccaa    4787
aggcatcacg agtcagtcgc ctttcagcag gcagccttgg cggtttatcg ccctggcagg    4847
caggggccct gcagctctca tgctgcccct gccttgggggt caggttgaca ggaggttgga    4907
gggaaagcct taagctgcag gattctcacc agctgtgtcc ggcccagttt tggggtgtga    4967
cctcaatttc aattttgtct gtacttgaac attatgaaga tggggcctc tttcagtgaa    5027 tttgtgaaca gcagaattga ccgacagctt tccagtaccc atggggctag gtcattaagg    5087
ccacatccac agtctccccc acccttgttc cagttgttag ttactacctc ctctcctgac    5147
aatactgtat gtcgtcgagc tccccccagg tctacccctc ccggccctgc ctgctggtgg    5207
gcttgtcata gccagtggga ttgccggtct tgacagctca gtgagctgga gatacttggt    5267
cacagccagg cgctagcaca gctcccttct gttgatgctg tattcccata tcaaaagaca    5327 cagggggacac ccagaaacgc cacatccccc aatccatcag tgccaaacta gccaacggcc    5387
ccagcttctc agctcgctgg atggcggaag ctgctactcg tgagcgccag tgcgggtgca    5447
gacaatcttc tgttgggtgg catcattcca ggcccgaagc atgaacagtg cacctgggac    5507
agggagcagc cccaaattgt cacctgcttc tctgcccagc ttttcattgc tgtgacagtg    5567
atggcgaaag agggtaataa ccagacacaa actgccaagt tgggtggaga aaggagtttc    5627
tttagctgac agaatctctg aatttttaaat cacttagtaa gcggctcaag cccaggaggg    5687
agcagaggga tacgagcgga gtcccctgcg cgggaccatc tggaattggt ttagcccaag    5747
tggagcctga cagccagaac tctgtgtccc ccgtctaacc acagctcctt ttccagagca    5807
```

```
ttccagtcag gctctctggg ctgactgggc caggggaggt tacaggtacc agttctttaa    5867
gaagatcttt gggcatatac attttttagcc tgtgtcattg ccccaaatgg attcctgttt    5927
caagttcaca cctgcagatt ctaggacctg tgtcctagac ttcagggagt cagctgtttc    5987
tagagttcct accatggagt gggtctggag gacctgcccg gtgggggggc agagccctgc    6047
tccctccggg tcttcctact cttctctctg ctctgacggg atttgttgat tctctccatt    6107
ttggtgtctt tctcttttag atattgtatc aatctttaga aaaggcatag tctacttgtt    6167
ataaatcgtt aggatactgc ctcccccagg gtctaaaatt acatattaga ggggaaaagc    6227
tgaacactga agtcagttct caacaattta aaggaaaaac ctagaaaaca tttggcagaa    6287
aattacattt cgatgttttt gaatgaatac gagcaagctt ttacaacagt gctgatctaa    6347
aaatacttag cacttggcct gagatgcctg gtgagcatta caggcaaggg gaatctggag    6407
gtagccgacc tgaggacatg gcttctgaac ctgtcttttg ggagtggtat ggaaggtgga    6467
gcgttcacca gtgacctgga aggcccagca ccaccctcct tcccactctt ctcatcttga    6527
cagagcctgc cccagcgctg acgtgtcagg aaaacaccca gggaactagg aaggcacttc    6587
tgcctgaggg gcagcctgcc ttgcccactc ctgctctgct cgcctcggat cagctgagcc    6647
ttctgagctg gcctctcact gcctccccaa ggcccctgc  ctgccctgtc aggaggcaga    6707
aggaagcagg tgtgagggca gtgcaaggag ggagcacaac ccccagctcc cgctccgggc    6767
tccgacttgt gcacaggcag agcccagacc ctggaggaaa tcctacccttt gaattcaaga    6827 acatttgggg aatttggaaa tctctttgcc cccaaacccc cattctgtcc tacctttaat    6887
caggtcctgc tcagcagtga gagcagatga ggtgaaaagg ccaagaggtt tggctcctgc    6947
ccactgatag cccctctccc cgcagtgttt gtgtgtcaag tggcaaagct gttcttcctg    7007
gtgaccctga ttatatccag taacacatag actgtgcgca taggcctgct tgtctcctc     7067 tatcctgggc ttttgttttg ctttttagtt ttgcttttag ttttttctgtc cctttattt     7127 aacgcaccga ctagacacac aaagcagttg aattttttata tatatatctg tatattgcac    7187
aattataaac tcattttgct tgtggctcca cacacacaaa aaaagacctg ttaaaattat    7247
acctgttgct taattacaat atttctgata accatagcat aggacaaggg aaaataaaaa    7307
aagaaaaaaa agaaaaaaaa acgacaaatc tgtctgctgg tcacttcttc tgtccaagca    7367
gattcgtggt cttttcctcg cttctttcaa gggcttccct gtgccaggtg aaggaggctc    7427
caggcagcac ccaggttttg cactcttgtt tctcccgtgc ttgtgaaaga ggtcccaagg    7487
ttctgggtgc aggagcgctc ccttgacctg ctgaagtccg gaacgtagtc ggcacagcct    7547
ggtcgccttc cacctctggg agctggagtc cactggggtg gcctgactcc cccagtcccc    7607
ttcccgtgac ctggtcaggg tgagcccatg tggagtcagc ctcgcaggcc tccctgccag    7667
tagggtccga gtgtgtttca tccttcccac tctgtcgagc ctgggggctg gagcggagac    7727
gggaggcctg gcctgtctcg gaacctgtga gctgcaccag gtagaacgcc agggacccca    7787
gaatcatgtg cgtcagtcca aggggtcccc tccaggagta gtgaagactc cagaaatgtc    7847
cctttcttct cccccatcct acgagtaatt gcatttgctt ttgtaattct taatgagcaa    7907
tatctgctag agagtttagc tgtaacagtt cttttttgatc atctttttt  aataattaga    7967 aacaccaaaa aaatccagaa acttgttctt ccaaagcaga gagcattata atcaccaggg    8027
ccaaaagctt ccctccctgc tgtcattgct tcttctgagg cctgaatcca aaagaaaaac    8087
agccataggc cctttcagtg gccgggctac ccgtgagccc ttcggaggac cagggctggg    8147
```

|  |  |  |  |  | |
|---|---|---|---|---|---|
| gcagcctctg | ggcccacatc | cggggccagc | tccggcgtgt | gttcagtgtt | agcagtgggt | 8207 |
| catgatgctc | tttcccaccc | agcctgggat | aggggcagag | gaggcgagga | ggccgttgcc | 8267 |
| gctgatgttt | ggccgtgaac | aggtgggtgt | ctgcgtgcgt | ccacgtgcgt | gttttctgac | 8327 |
| tgacatgaaa | tcgacgcccg | agttagcctc | acccggtgac | tctagcccct | gcccggatgg | 8387 |
| agcggggccc | acccggttca | gtgtttctgg | ggagctggac | agtggagtgc | aaaaggcttg | 8447 |
| cagaacttga | agcctgctcc | ttcccttgct | accacggcct | cctttccgtt | tgatttgtca | 8507 |
| ctgcttcaat | caataacagc | cgctccagag | tcagtagtca | atgaatatat | gaccaaatat | 8567 |
| caccaggact | gttactcaat | gtgtgccgag | cccttgccca | tgctgggctc | ccgtgtatct | 8627 |
| ggacactgta | acgtgtgctg | tgtttgctcc | ccttcccctt | ccttctttgc | cctttacttg | 8687 |
| tctttctggg | gttttctgt | ttgggtttgg | tttggttttt | atttctcctt | ttgtgttcca | 8747 |
| aacatgaggt | tctctctact | ggtcctctta | actgtggtgt | tgaggcttat | atttgtgtaa | 8807 |
| tttttggtgg | gtgaaaggaa | ttttgctaag | taaatctctt | ctgtgtttga | actgaagtct | 8867 |
| gtattgtaac | tatgttaaa | gtaattgttc | cagagacaaa | tatttctaga | cacttttct | 8927 |
| ttacaaacaa | aagcattcgg | agggaggggg | atggtgactg | agatgagagg | ggagagctga | 8987 |
| acagatgacc | cctgcccaga | tcagccagaa | gccacccaaa | gcagtggagc | ccaggagtcc | 9047 |
| cactccaagc | cagcaagccg | aatagctgat | gtgttgccac | tttccaagtc | actgcaaaac | 9107 |
| caggttttgt | tccgcccagt | ggattcttgt | tttgcttccc | ctcccccga | gattattacc | 9167 |
| accatcccgt | gcttttaagg | aaaggcaaga | ttgatgtttc | cttgagggga | gccaggaggg | 9227 |
| gatgtgtgtg | tgcagagctg | aagagctggg | gagaatgggg | ctgggcccac | ccaagcagga | 9287 |
| ggctgggacg | ctctgctgtg | ggcacaggtc | aggctaatgt | tggcagatgc | agctcttcct | 9347 |
| ggacaggcca | ggtggtgggc | attctctctc | caaggtgtgc | cccgtgggca | ttactgttta | 9407 |
| agacacttcc | gtcacatccc | accccatcct | ccagggctca | acactgtgac | atctctattc | 9467 |
| cccaccctcc | ccttcccagg | gcaataaaat | gaccatggag | ggggcttgca | ctctcttggc | 9527 |
| tgtcacccga | tcgccagcaa | aacttagatg | tgagaaaacc | ccttcccatt | ccatggcgaa | 9587 |
| aacatctcct | tagaaaagcc | attaccctca | ttaggcatgg | ttttgggctc | ccaaaacacc | 9647 |
| tgacagcccc | tccctcctct | gagaggcgga | gagtgctgac | tgtagtgacc | attgcatgcc | 9707 |
| gggtgcagca | tctggaagag | ctaggcaggg | tgtctgcccc | ctcctgagtt | gaagtcatgc | 9767 |
| tcccctgtgc | cagcccagag | gccgagagct | atggacagca | ttgccagtaa | cacaggccac | 9827 |
| cctgtgcaga | agggagctgg | ctccagcctg | gaaacctgtc | tgaggttggg | agaggtcac | 9887 |
| ttggggcaca | gggagaggcc | gggacacact | tagctggaga | tgtctctaaa | agccctgtat | 9947 |
| cgtattcacc | ttcagttttt | gtgttttggg | acaattactt | tagaaaataa | gtaggtcgtt | 10007 |
| ttaaaaacaa | aaattattga | ttgctttttt | gtagtgttca | gaaaaaaggt | tctttgtgta | 10067 |
| tagccaaatg | actgaaagca | ctgatatatt | taaaaacaaa | aggcaattta | ttaaggaaat | 10127 |
| ttgtaccatt | tcagtaaacc | tgtctgaatg | tacctgtata | cgtttcaaaa | acacccccc | 10187 |
| cccactgaat | ccctgtaacc | tatttattat | ataaagagtt | tgccttataa | attt | 10241 |

<210> SEQ ID NO 15
<211> LENGTH: 486
<212> TYPE: PRT
<213> ORGANISM: Homo sapiens

<400> SEQUENCE: 15

Met Val Ala Gly Met Leu Gly Leu Arg Glu Glu Lys Ser Glu Asp Gln

-continued

```
1               5                   10                  15
Asp Leu Gln Gly Leu Lys Asp Lys Pro Leu Lys Phe Lys Lys Val Lys
                20                  25                  30
Lys Asp Lys Lys Glu Glu Lys Glu Gly Lys His Glu Pro Val Gln Pro
                35                  40                  45
Ser Ala His His Ser Ala Glu Pro Ala Glu Ala Gly Lys Ala Glu Thr
                50                  55                  60
Ser Glu Gly Ser Gly Ser Ala Pro Ala Val Pro Glu Ala Ser Ala Ser
65                  70                  75                  80
Pro Lys Gln Arg Arg Ser Ile Ile Arg Asp Arg Gly Pro Met Tyr Asp
                85                  90                  95
Asp Pro Thr Leu Pro Glu Gly Trp Thr Arg Lys Leu Lys Gln Arg Lys
                100                 105                 110
Ser Gly Arg Ser Ala Gly Lys Tyr Asp Val Tyr Leu Ile Asn Pro Gln
                115                 120                 125
Gly Lys Ala Phe Arg Ser Lys Val Glu Leu Ile Ala Tyr Phe Glu Lys
                130                 135                 140
Val Gly Asp Thr Ser Leu Asp Pro Asn Asp Phe Asp Phe Thr Val Thr
145                 150                 155                 160
Gly Arg Gly Ser Pro Ser Arg Arg Glu Gln Lys Pro Pro Lys Lys Pro
                165                 170                 175
Lys Ser Pro Lys Ala Pro Gly Thr Gly Arg Gly Arg Gly Arg Pro Lys
                180                 185                 190
Gly Ser Gly Thr Thr Arg Pro Lys Ala Ala Thr Ser Glu Gly Val Gln
                195                 200                 205
Val Lys Arg Val Leu Glu Lys Ser Pro Gly Lys Leu Leu Val Lys Met
210                 215                 220
Pro Phe Gln Thr Ser Pro Gly Gly Lys Ala Glu Gly Gly Gly Ala Thr
225                 230                 235                 240
Thr Ser Thr Gln Val Met Val Ile Lys Arg Pro Gly Arg Lys Arg Lys
                245                 250                 255
Ala Glu Ala Asp Pro Gln Ala Ile Pro Lys Lys Arg Gly Arg Lys Pro
                260                 265                 270
Gly Ser Val Val Ala Ala Ala Ala Glu Ala Lys Lys Lys Ala Val
                275                 280                 285
Lys Glu Ser Ser Ile Arg Ser Val Gln Glu Thr Val Leu Pro Ile Lys
                290                 295                 300
Lys Arg Lys Thr Arg Glu Thr Val Ser Ile Glu Val Lys Glu Val Val
305                 310                 315                 320
Lys Pro Leu Leu Val Ser Thr Leu Gly Glu Lys Ser Gly Lys Gly Leu
                325                 330                 335
Lys Thr Cys Lys Ser Pro Gly Arg Lys Ser Lys Glu Ser Ser Pro Lys
                340                 345                 350
Gly Arg Ser Ser Ser Ala Ser Ser Pro Pro Lys Lys Glu His His His
                355                 360                 365
His His His His Ser Glu Ser Pro Lys Ala Pro Val Pro Leu Leu Pro
                370                 375                 380
Pro Leu Pro Pro Pro Pro Glu Pro Glu Ser Ser Glu Asp Pro Thr
385                 390                 395                 400
Ser Pro Pro Glu Pro Gln Asp Leu Ser Ser Val Cys Lys Glu Glu
                405                 410                 415
Lys Met Pro Arg Gly Gly Ser Leu Glu Ser Asp Gly Cys Pro Lys Glu
                420                 425                 430
```

```
Pro Ala Lys Thr Gln Pro Ala Val Ala Thr Ala Ala Thr Ala Ala Glu
        435                 440                 445

Lys Tyr Lys His Arg Gly Glu Gly Glu Arg Lys Asp Ile Val Ser Ser
    450                 455                 460

Ser Met Pro Arg Pro Asn Arg Glu Glu Pro Val Asp Ser Arg Thr Pro
465                 470                 475                 480

Val Thr Glu Arg Val Ser
                485
```

METHODS FOR THE DIAGNOSIS AND TREATMENT OF SJÖGREN'S SYNDROME

CROSS REFERENCE TO RELATED APPLICATIONS

This is the U.S. National Stage of International Application No. PCT/2013/061587, filed Sep. 25, 2013, published in English under PCT Article 21(2), which claims the benefit of U.S. Provisional Application No. 61/705,517, filed Sep. 25, 2012, which is herein incorporated by reference in its entirety.

FIELD

This disclosure concerns methods for the diagnosis of Sjögren's syndrome by detecting gene expression changes in the salivary gland, detecting an increase in electrical potential of the salivary gland, or both. This disclosure further concerns the treatment of Sjögren's syndrome by modulating expression or activity of genes that are differentially expressed in Sjögren's syndrome patients.

BACKGROUND

Sjögren's syndrome is an autoimmune disorder in which immune cells attack and destroy the glands that produce tears and saliva. Sjögren's syndrome is considered a rheumatic disorder, meaning it causes inflammation in the joints, muscles, skin and/or other organs. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, and is currently the second most common autoimmune rheumatic disease in the United States. The majority of Sjögren's sufferers are at least 40 years old at the time of diagnosis, and women are nine times more likely to develop the disease. Sjögren's syndrome can occur as a primary rheumatic condition or as a secondary disorder in association with other rheumatic diseases, such as systemic lupus erythematosus ("lupus"), scleroderma biliary cirrhosis or rheumatoid arthritis.

Sjögren's syndrome can damage vital organs of the body with symptoms that may remain stable, worsen, or go into remission. Some patients experience only the mild symptoms of dry eyes and mouth, while others go through cycles of good health followed by severe disease. While many patients are able to treat problems symptomatically, others suffer from blurred vision, constant eye discomfort, recurrent mouth infections, swollen parotid glands, hoarseness, and difficulty in swallowing and eating. Debilitating fatigue and joint pain can seriously impair quality of life.

There is currently no known cure for Sjögren's syndrome, nor is there a specific treatment to restore gland secretion. Treatment is generally symptomatic and supportive, including moisture replacement therapies to relieve the symptoms of eye and mouth dryness. Non-steroidal anti-inflammatory drugs can be used to treat musculoskeletal symptoms. For individuals with severe complications, corticosteroids or immunosuppressive drugs are often prescribed. These drugs can have serious side effects. Moreover, diagnosis of the disease is currently based on a combination of indications, such as objective and subjective dryness, autoantibodies, and mononuclear infiltrates and is primarily a process of elimination of other known diseases to arrive at the diagnosis of Sjögren's syndrome. Therefore, a need exists to not only accurately diagnose patients with Sjögren's syndrome, but to identify viable therapeutic targets for treatment of the disease.

Bone morphogenetic protein 6 (BMP6) is a member of the TGF-β superfamily of growth factors. Expression of BMP6 has been detected in several different mammalian tissues and cell types, including smooth muscle cells, growth plate chondrocytes, bronchiolar epithelium, cornea, epidermis, salivary gland and cells of the nervous system (Blessing et al., *J Cell Biol* 135(1):227-239, 1996). In vitro, BMP6 has been shown to inhibit cell division, promote terminal epithelial differentiation, and induce endochondral bone formation, osteoblastic differentiation and neuronal maturation (Heikinheimo et al., *Cancer Res* 59:5815-5821, 1999).

DNA methylation is the major modification of eukaryotic genomes and plays an essential role in mammalian development. The human proteins MECP2, MBD1, MBD2, MBD3, and MBD4 comprise a family of nuclear proteins related by the presence in each of a methyl-CpG binding domain (MBD). Each of these proteins, with the exception of MBD3, is capable of binding specifically to methylated DNA. MECP2, MBD1 and MBD2 can also repress transcription from methylated gene promoters. In contrast to other MBD family members, MECP2 is X-linked and subject to X inactivation.

X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIST gene (X (inactive)-specific transcript (non-protein coding)) is expressed exclusively from the XIC of the inactive X chromosome. The transcript is spliced but does not encode a protein. The transcript remains in the nucleus where it coats the inactive X chromosome.

SUMMARY

Disclosed herein is the finding that BMP6 is overexpressed in the salivary glands of Sjögren's syndrome patients. Also disclosed is the finding that overexpression of BMP6 in the salivary gland is associated with increased electrical potential across the salivary gland.

Provided herein is a method of diagnosing a subject as having Sjögren's syndrome, or at risk for developing Sjögren's syndrome by detecting expression of BM6 in a biological sample of the subject. A diagnostically significant increase in expression of BMP6 in the biological sample of the subject relative to a control, diagnoses the subject as having Sjögren's syndrome, or being at risk for developing Sjögren's syndrome. In some embodiments, the biological sample is a salivary gland.

Also provided herein is a method of treating a subject with Sjögren's syndrome by selecting a subject with increased BMP6 expression and administering to the subject a therapeutically effective amount of an agent that inhibits expression or activity of BMP6.

Further provided is a method of diagnosing a subject as having Sjögren's syndrome, or being at risk for developing Sjögren's syndrome, by performing electrophysiologic tissue measurements, for example measuring tissue impedance or measuring electrical potential across a salivary gland of the subject. A diagnostically significant increase in the electrical potential or impedance in the subject relative to a control diagnoses the subject as having Sjögren's syndrome, or being at risk for developing Sjögren's syndrome. The disclosed diagnostic methods provide an objective, reproducible standard for diagnosing Sjögren's syndrome and assessing disease course or response to therapy without relying exclusively on subjective criteria.

Described herein is the finding that male Sjögren's syndrome patients express XIST, a non-coding RNA that is typically not expressed in males. Also described is the finding that male Sjögren's syndrome patients down-regulate MECP2, as well as other proteins involved in DNA methylation. Thus, provided herein is a method of diagnosing a male subject as having Sjögren's syndrome, or at risk for developing Sjögren's syndrome, by detecting expression of XIST, MECP2, or both, in a biological sample of the subject. A diagnostically significant increase in expression of XIST, a diagnostically significant decrease in expression of MECP2, or both, in the biological sample of the subject relative to a control, diagnoses the subject as having Sjögren's syndrome, or at risk for developing Sjögren's syndrome. In some embodiments, the biological sample is a salivary gland, such as a minor salivary gland.

Also described herein is the finding that in a subset of male Sjögren's syndrome patients, Y-chromosome gene expression is down-regulated, as is expression of ribosomal proteins that regulate RNA processing and viral replication, and proteins that regulate DNA methylation. These findings provide additional markers that can be utilized for the diagnosis and treatment of Sjögren's syndrome.

Further provided is a method of treating a male subject with Sjögren's syndrome by selecting a male subject with increased expression of XIST, and administering to the subject a therapeutically effective amount of an agent that inhibits expression of XIST. Also provided is a method of treating a male subject with Sjögren's syndrome by selecting a male subject with decreased expression of MECP2 and administering to the subject a therapeutically effective amount of a nucleic acid molecule encoding MECP2.

The foregoing and other objects, features, and advantages of the invention will become more apparent from the following detailed description, which proceeds with reference to the accompanying figures.

BRIEF DESCRIPTION OF THE FIGURES

(FIG. 1A) Shown are the top up-regulated and down-regulated genes in female Sjögren's syndrome patients. The values are presented as fold changes in expression levels of patients with respect to healthy, age and gender-matched volunteers. (FIG. 1B) Quantitative-PCR of selected genes shows agreement with microarray results. The results obtained using the custom microarray platform were validated by examining the correlation between the expression levels in the microarray and qPCR results obtained for a subset of genes. The quantitative-PCR results were obtained using representative samples from the patient population as well as the healthy volunteers in the study.

FIGS. 2A-2B: BMP6 expression is differentially expressed at the transcript as well as the protein level. Immunofluorescence studies on salivary gland tissue used for microarray analysis. (FIG. 2A) The level of expression by immunofluorescence of BMP6 in a patient when compared to a healthy volunteer. (FIG. 2B) Digital Western-Blot analysis quantifying BMP6 immunofluorescence intensity as a number of pixels of a given intensity in similar regions inside the image.

(FIG. 3A) Mice cannulated with a combination of AAV5BMP6 and AAV5 luciferase were imaged in vivo for luciferase expression. The vast majority of signal was localized within the SGs (n=9). (FIG. 3B) Immunofluorescence staining for BMP6 indicated extensive staining in the ductal cells, consistent with the ductal tropism of AAV5 vectors.

(FIG. 4A) Mice treated with AAV5BMP6 expressing vector showed a significant loss of gland activity compared with control mice. (FIG. 4B) In contrast, salivary gland delivery did not result in a systemic effect as determined by a change in lacrimal gland activity. (FIG. 4C) Delivery of AAV5BMP6 to the lacrimal glands decreased tear flow in treated mice compared with control mice.

FIG. 9: Cytokine production in serum and salivary gland. Table showing levels of murine IL-1β, IL-2, IL-4, IL-5, IL-6, IL-10, IL-12p70, Il-12p40, IL-13, IL-17, IL-18, IL-23, KC, JE, MCP5, MIP1β, MMP9, L-selectin, RANTES, TGF-β1, IFN-γ and TNF-α in salivary gland (SG) homogenates and serum of mice transduced with AAV5BMP6 or AAV5GFP. Duplicates for each sample were tested in three dilutions and the mean values of the duplicates from the optimal dilution are shown.

FIGS. 11A-11B: Transmembrane epithelial electrical potential in SMG of AAV2-Cre transduced St14$^{LoxP/LoxP}$ mice and correlation with salivary gland activity. St14$^{LoxP/LoxP}$ mice were transduced with $1.8 \times 10^{11}$ particles of adeno-associated virus expressing Cre recombinase or AAV2 expressing LacZ. Mice with pierced ducts served as controls. Twenty-two weeks following vector administration, mice were anesthetized and electrical potential in the SMG was measured (FIG. 11A). Salivary flow rate (SFR) was measured and plotted against TEER (FIG. 11B).

FIG. 16: Comparative genomic hybridization to detect copy number variance. The table summarizes the finding that a significant number of mosaic-level duplications and/or deletions are found in the opsin (OPN1LW, OPN1MW, OPN1MW2) and tex28 region in the X-chromosome of male subjects with pSS.

SEQUENCE LISTING

Figure 1A:
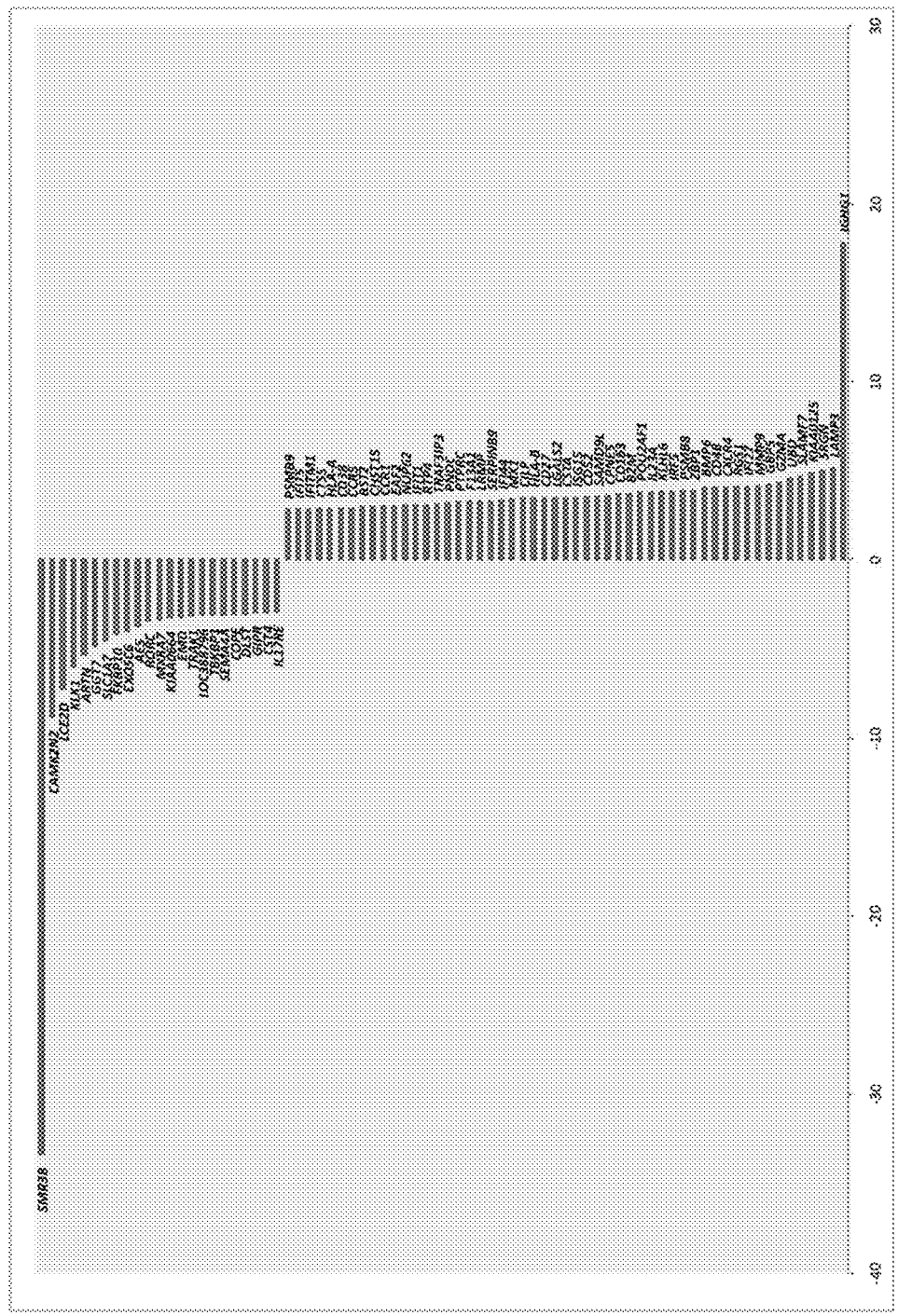
FIGS. 1A-1B: Analysis of microarray data.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 11, 2015, 107 KB, which is incorporated by reference herein. In the accompanying sequence listing:

SEQ ID NOs: 1 and 2 are the nucleotide and amino acid sequences, respectively, of human BMP6.

SEQ ID NOs: 3 and 4 are the nucleotide and amino acid sequences, respectively, of mouse BMP6.

SEQ ID NOs: 5 and 6 are the nucleotide and amino acid sequences, respectively, of human HJV.

SEQ ID NOs: 7 and 8 are the nucleotide and amino acid sequences, respectively, of human BAMBI.

SEQ ID NOs: 9 and 10 are the nucleotide and amino acid sequences, respectively, of human sclerostin.

SEQ ID NOs: 11 and 12 are the nucleotide and amino acid sequences, respectively, of human noggin.

SEQ ID NO: 13 is the nucleotide sequence of human XIST.

SEQ ID NOs: 14 and 15 are the nucleotide and amino acid sequences, respectively, of human MECP2.

DETAILED DESCRIPTION

I. Abbreviations
AAV adeno-associated virus
BMP6 bone morphogenetic protein 6
BSA bovine serum albumin
BW body weight
CGH comparative genomic hybridization
ELISA enzyme-linked immunosorbent assay
EP electrical potential
FS focus score
HTS hypotonic solution
HV healthy volunteer
IFN interferon
IL interleukin
IM intramuscular
IPA Ingenuity Pathway Analysis
MECP2 methyl CpG binding protein 2
NOD non-obese diabetic
OD optical density
O/N overnight
pSS primary Sjögren's syndrome
qPCR quantitative polymerase chain reaction
RIN RNA integrity number
RT room temperature
RT-PCR reverse transcriptase polymerase chain reaction
RVD regulated volume decrease
SFR salivary flow rate SG salivary gland
SMG submandibular gland
SS Sjögren's syndrome
TEER trans epithelial electric resistance
TGF transforming growth factor
WT wild type
XIST X (inactive)-specific transcript (non-protein coding)

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Agent that promotes salivary production: Any compound that increases the amount of saliva produced in a subject (for example, a subject with Sjögren's syndrome). In some cases, an agent that promotes salivary production is a therapeutic agent prescribed by a physician, such as pilocarpine (Salagen™) or cevimeline (Evoxac™). In some examples, the agent that promotes salivary production is an inhibitor of BMP6 expression or activity.

Alteration in expression: An alteration in expression refers to a change in the level of a gene transcript (for example, mRNA) or gene product (for example, protein) that is detectable in a biological sample (such as a sample from a patient with Sjögren's syndrome, for example, in a salivary gland biopsy) relative to a control (such as a healthy subject). An "alteration" in expression includes an increase in expression (up-regulation) or a decrease in expression (down-regulation).

Antibody: A polypeptide ligand including at least a light chain or heavy chain immunoglobulin variable region which specifically recognizes and binds an epitope of an antigen, such as BMP6 or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda and kappa. There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody will have a specific $V_H$ region and the $V_L$ region sequence, and thus specific CDR sequences. Antibodies with different specificities (such as different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "$V_L$" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds an ovarian endothelial cell tumor-associated molecule.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Antisense compound: Refers to an oligomeric compound that is at least partially complementary to the region of a target nucleic acid molecule to which it hybridizes. As used herein, a "target" nucleic acid is a nucleic acid molecule to which an antisense compound is designed to specifically hybridize. Non-limiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self-complementarity to allow for hybridization and formation of a fully or partially double-stranded compound.

Aptamer: Nucleic acid (such as RNA or DNA) aptamers are molecules that bind to a specific target molecule. Aptamers can be selected or designed to bind a variety of different types of molecular targets, including small molecules, proteins, nucleic acids, cells or tissues. Aptamers have previously been developed for therapeutic purposes, such as Macugen™, which targets VEGF for the treatment of macular degeneration, and ARC 1779, which targets von Willebrand factor for the treatment of acute coronary syndrome.

Biological sample: A biological specimen containing genomic DNA, RNA (including mRNA and microRNA), protein, or combinations thereof, obtained from a subject. Examples include, but are not limited to, saliva, peripheral blood, urine, tissue biopsy, surgical specimen, and autopsy material. In one example, a sample includes a biopsy of a salivary gland, such as from a patient with Sjögren's syndrome or a healthy control subject. In other embodiments, the biological sample is a saliva sample. In other embodiments, the biological sample is blood, or a component thereof, such as plasma or serum.

BMP and activin membrane-bound inhibitor homolog (BAMBI): A transmembrane glycoprotein related to the type I receptors of the transforming growth factor-beta (TGF-beta) family, whose members play important roles in signal transduction in many developmental and pathological processes. BAMBI is a pseudoreceptor, lacking an intracellular serine/threonine kinase domain required for signaling. Nucleotide and amino acid sequences for BAMBI are publically available, such as in the GenBank database (see NCBI Gene ID 25805 for human BAMBI). Exemplary human nucleotide and amino acid sequences are set forth herein as SEQ ID NOs: 7 and 8, respectively. In some examples herein, the complete BAMBI protein (SEQ ID NO: 8) is used as a soluble binding protein specific for BMP6. In other examples, a BAMBI fragment consisting of amino acid residues 20-152 of SEQ ID NO: 8 is used as a soluble binding protein specific for BMP6.

Bone morphogenetic protein 6 (BMP6): A member of the TGF-β superfamily of growth factors. Expression of BMP6 has been detected in several different mammalian tissues and cell types, including smooth muscle cells, growth plate chondrocytes, bronchiolar epithelium, cornea, epidermis, salivary gland and cells of the nervous system (Blessing et al., J Cell Biol 135(1):227-239, 1996). In vitro, BMP6 has been shown to inhibit cell division, promote terminal epithelial differentiation, and induce endochondral bone formation, osteoblastic differentiation and neuronal maturation (Heikinheimo et al., Cancer Res 59:5815-5821, 1999). BMP6 is also known as vegetal related growth factor (TGFB-related), VGR, VGR1 and VG-1-related protein. Genomic, mRNA and protein sequences for BMP6 from a number of different species are publically available, such as in the GenBank database from the National Center for Biotechnology Information. See, for example, Gene ID 654 (human), Gene ID 12161 (mouse), Gene ID 25644 (rat), Gene ID 503761 (zebrafish), Gene ID 420868 (chicken), Gene ID 100033934 (horse), Gene ID 443174 (sheep), Gene ID 100155536 (pig), Gene ID 695091 (rhesus macaque) and Gene ID 471851 (chimpanzee). Exemplary mRNA and protein sequences of human (SEQ ID NOs: 1 and 2) and mouse (SEQ ID NOs: 3 and 4) BMP6 are set forth herein in the Sequence Listing.

Control: A "control" refers to a sample or standard used for comparison with an experimental sample, such as a salivary gland sample obtained from a patient with Sjögren's syndrome. In some embodiments, the control is a sample obtained from a healthy volunteer (also referred to herein as a "normal" control). In some embodiments, the control is a historical control or standard value (i.e. a previously tested control sample or group of samples that represent baseline or normal values).

Corticosteroids: Steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Examples of corticosteroids include cortisol and prednisone.

Diagnosis: The process of identifying a disease by its signs, symptoms and/or results of various tests. The conclusion reached through that process is also called "a diagnosis." Forms of testing commonly performed include physical examination, blood tests, medical imaging, genetic analysis, urinalysis, and biopsy.

Diagnostically significant amount: In some embodiments, a "diagnostically significant amount" refers to an increase or decrease in the level of BMP6 (or any other gene or protein) in a biological sample that is sufficient to allow one to distinguish one patient population from another (such as a Sjögren's syndrome patient population from a group of healthy individuals). In some examples, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold. RT-PCR is provided herein as one example of how BMP6 expression can be detected Immunoassays, such as an ELISA, are another example of a method for detecting expression of BMP6. However, one of skill in the art will recognize that other methods exist to measure gene expression and variation in detected expression levels can occur depending on the method that is used. Thus, the diagnostically significant amount may vary if another method of detection is used. In other embodiments, a "diagnostically significant amount" refers to an increase or decrease in electrical potential of a salivary gland that is sufficient to allow one to distinguish one patient population from another (such as a Sjögren's syndrome patient population from a group of healthy controls). In some examples, the diagnostically significant increase or decrease is about 10%, about 20%, about 30%, about 40% or about 50%.

Dorsomorphin: A small molecule inhibitor of BMP signaling. Dorsomorphin functions through inhibition of BMP type I receptors ALK2, ALK3 and ALK6, thereby blocking BMP-mediated SMAD1/5/8 phosphorylation. In particular, dorsomorphin has been shown to inhibit signaling by BMP2, BMP4, BMP6 and BMP7 (Yu et al., *Nat Chem Biol* 4(1): 33-41, 2008).

Electrical potential: The work per unit charge necessary to move a charged body in an electrical field from a reference point to another point (such as between a salivary gland duct and adjacent tissue), measured in volts. The electrical potential (V) is related to current (I) and resistance (R) by the relationship V=IR. A fixed voltage may be applied from a voltmeter and current measured at two points with probes to determine resistance. Alternatively, voltage can be determined from using I and R.

Focus score: A measure of inflammation often used in the diagnosis of Sjögren's syndrome. Focus score is determined by measuring the number of lymphocytic foci (containing at least 50 inflammatory cells) in a 4 mm$^2$ glandular section.

Healthy control subject: A subject that is not clinically diagnosed with Sjögren's syndrome after an appropriate examination. Healthy control subjects are also referred to herein as "healthy volunteers."

Hemojuvelin (HJV): A membrane-bound and soluble protein that is responsible for the iron overload condition known as juvenile hemochromatosis. The human hemojuvelin protein is encoded by the HFE2 gene. HJV is also known as RGMc. The soluble form of HJV is referred to as sHJV. Nucleotide and amino acid sequences for HFE2 and its encoded protein HJV are publically available, such as in the GenBank database (see Gene ID 148738 for human HFE2/HJV). Exemplary human nucleotide and amino acid sequences are set forth herein as SEQ ID NOs: 5 and 6, respectively. In some embodiments of the present disclosure, sHJV comprises or consists of amino acid residues 35-426 or 35-332 of human HJV (SEQ ID NO: 6).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 60% Identity)
Hybridization: 6×SSC at RT to 55° C. for 16-20 hours
Wash at least twice: 2×-3×SSC at RT to 55° C. for 20-30 minutes each.

Immunosuppressive drug: Includes any agent or compound having the ability to decrease the body's immune system responses. In some embodiments, the immunosuppressive drug is a corticosteroid. In other embodiments, the immunosuppressive drug is a small molecule (such as cyclosporine) or a monoclonal antibody (such as a cytokine blocker).

Inhibitor: Any chemical compound, nucleic acid molecule, small molecule, peptide or polypeptide (such as an antibody) that can reduce activity of a gene product or interfere with expression of a gene. In some examples, an inhibitor can reduce or inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. In some examples, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Inhibit expression or activity: As used herein, an agent that inhibits expression or activity of a gene (such as BMP6) is an agent that reduces the level of mRNA or protein expressed by the gene (such as BMP6) in a cell or tissue, or reduces (including eliminates) one or more activities of the gene or encoded protein (such as BMP6). Similarly, an agent that inhibits BMP signaling is any compound that inhibits, blocks or prevents signaling events in the BMP signaling pathway, such as phosphorylation of downstream targets, for example phosphorylation of SMAD1/5/8.

Isolated: An "isolated" biological component (such as a nucleic acid molecule, protein, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Measuring the level of expression: Quantifying the amount of a gene product present in a sample. Quantification can be either numerical or relative. Detecting expression of the gene product (such as BMP6 mRNA or protein) can be achieved using any method known in the art or described herein, such as by RT-PCR, antibody-binding (e.g., ELISA), or immunohistochemistry. In some embodiments, the change detected is an increase or decrease in expression as compared to a control. In some examples, the detected increase or decrease is an increase or decrease of at least two-fold, at least three fold or at least four-fold compared with the control. In other embodiments of the methods, the increase or decrease is of a diagnostically significant amount, which refers to a change of a sufficient magnitude to provide a statistical probability of the diagnosis.

Methyl CpG binding protein 2 (MECP2): DNA methylation is the major modification of eukaryotic genomes and plays an essential role in mammalian development. Human proteins MECP2, MBD1, MBD2, MBD3, and MBD4 comprise a family of nuclear proteins related by the presence in each of a methyl-CpG binding domain (MBD). Each of these proteins, with the exception of MBD3, is capable of binding specifically to methylated DNA. MECP2, MBD1 and MBD2 can also repress transcription from methylated gene promoters. In contrast to other MBD family members, MECP2 is X-linked and subject to X inactivation. MECP2 is dispensable in stem cells, but is essential for embryonic development. MECP2 gene mutations are the cause of most cases of Rett syndrome, a progressive neurologic developmental disorder and one of the most common causes of mental retardation in females. MECP2 is also known as RS; RTS; RTT; PPMX; MRX16; MRX79; MRXSL; AUTSX3; MRXS13; and DKFZp686A24160. Genomic, mRNA and protein sequences for MECP2 are publically available, such as in the GenBank database from the National Center for Biotechnology Information. See, for example, Gene ID 4204 for human MECP2. Exemplary mRNA and protein sequences for human MECP2 are set forth herein as SEQ ID NOs: 14 and 15.

Noggin (NOG): A secreted protein that binds and inactivates members of the transforming growth factor-beta (TGF-beta) superfamily signaling proteins, such as BMP4 and BMP6. By diffusing through extracellular matrices more efficiently than members of the TGF-beta superfamily, this protein may have a principal role in creating morphogenic gradients. The protein appears to have pleiotropic effect, both early in development as well as in later stages. Nucleotide and amino acid sequences of noggin are publically available, such as in the GenBank database (see NCBI Gene ID 9241 for human noggin).

Non-steroidal anti-inflammatory drug (NSAID): A type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as Sjögren's syndrome) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Restoring salivary flow: The process of increasing salivary production in a subject with diminished salivary flow, such as may result from Sjögren's syndrome. In some embodiments, restoring salivary flow can be accomplished by administering a therapeutic agent. In some examples, the therapeutic agent is a pharmaceutical, such as pilocarpine (Salagen™) or cevimeline (Evoxac™). In other examples, the therapeutic agent is an inhibitor of BMP6 expression or activity.

Restoring tear production: The process of increasing tear production in a subject with diminished tearing, such as may result from Sjögren's syndrome. In some embodiments, restoring tear production can be accomplished by administering a therapeutic agent. In particular examples, the therapeutic agent is an inhibitor of BMP6 expression or activity.

Salivary glands: Exocrine glands that produce saliva. As used herein, a "salivary gland" includes any salivary gland in a human subject, including, for example, the parotid glands, minor salivary glands, submandibular glands, sublingual glands and Von Ebner's glands. There are over 600 minor salivary glands located throughout the oral cavity.

Schirmer's test: A test used to determine whether tear glands produce enough tears to keep eyes adequately moist. Calibrated strips of a non-toxic filter paper are used. One free end is placed within the lower eyelid. Both eyes are tested at the same time. Before the test, numbing eye drops may be given to prevent eyes from tearing due to irritation from the paper. After 5 minutes, the paper strips are removed from each lower eyelid and the amount of wetting of the paper strips is measured. Wetting of less than 5 mm is indicative of deficient tear production.

Sclerostin (SOST): A secreted glycoprotein with a C-terminal cysteine knot-like (CTCK) domain and sequence similarity to the DAN (differential screening-selected gene aberrative in neuroblastoma) family of bone morphogenetic protein (BMP) antagonists. Loss-of-function mutations in this gene are associated with an autosomal-recessive disorder, sclerosteosis, which causes progressive bone overgrowth. A deletion downstream of this gene, which causes reduced sclerostin expression, is associated with a milder form of the disorder called van Buchem disease. Nucleotide and amino acid sequences of sclerostin are publically available, such as in the GenBank database (see Gene ID 50964 for human sclerostin). Exemplary nucleotide and amino acid sequences of human sclerostin are set forth herein as SEQ ID NOs: 9 and 10, respectively.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Sialogogue medications: Orally available medications that increase saliva production by stimulating the muscarinic acetylcholine receptors. Currently, pilocarpine (Salagen™) and cevimeline (Evoxac™) are approved for this indication in the United States.

Sjögren's syndrome (SS): An autoimmune disorder characterized by immune cells that attack and destroy the glands that produce tears and saliva. Sjögren's syndrome is not life-threatening or life-shortening, but can significantly reduce quality of life. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis.

A number of different criteria can be used to identify a subject having Sjögren's syndrome and include one or more of: (i) ocular symptoms (for example, persistent dry eyes and/or recurrent sensation of sand or gravel in eyes); (ii) oral symptoms (for example, daily feeling of dry mouth, persistently swollen salivary glands, and/or drinking liquids to swallow dry food); (iii) objective evidence of ocular involvement defined as a positive result of a Schirmer's test performed without anesthesia (≤5 mm in 5 minutes) and/or Rose bengal score or other ocular surface staining score (≥4 according to van Bijsterveld's scoring system; (iv) histopathology in minor salivary glands (measuring focus score or Tarpley score); (v) salivary gland involvement demonstrated with objective evidence of salivary gland involvement by a positive result for unstimulated whole salivary flow (≤1.5 ml in 15 minutes), parotid sialography showing the presence of diffuse sialectasias (punctate, cavitary, or destructive pattern) without evidence of obstruction in the major ducts, and/or salivary scintigraphy showing delayed, uptake, reduced concentration and/or delayed excretion of tracer; or (vi) autoantibodies (presence in the serum of antibodies to Ro (SSA) or La (SSB) antigens, or both. Thus, in some embodiments, a subject exhibiting one or more of the above signs or symptoms is selected for treatment according to the methods disclosed herein.

The presence of sicca (dryness) symptoms (sicca symptomology) in the absence of another connective tissue disease is designated "primary Sjögren's syndrome." Primary Sjögren's syndrome can also be characterized in subjects having a positive result for any four of the six criteria listed above, as long as either histopathology (item iv) or serology (item vi) is positive, or the presence of any three of the four objective criteria listed above (that is, items iii, iv, v, vi). Patients with an autoimmune process (such as rheumatoid arthritis, systemic lupus erythematosus, progressive systemic sclerosis, scleroderma, or polymyositis), in the presence of item i or item ii listed above, plus any two criteria from items iii, iv, and v, are characterized as having "secondary Sjögren's syndrome."

Soluble binding molecule: A non-membrane bound molecule that specifically binds another molecule such as BMP6). In some embodiments, the soluble binding molecule is sHJV, BAMBI (or fragment thereof), noggin, follistatin, chordin or sclerostin.

Specific binding agent: An agent that binds substantially or preferentially only to a defined target, such as a protein, enzyme, polysaccharide, oligonucleotide, DNA, RNA or a small molecule. For example, a "specific binding agent" includes an antisense oligonucleotide that specifically hybridizes with a target nucleic acid molecule, an antibody specific for a particular protein, an RNA aptamer that binds substantially to a specified protein, a small molecule that preferentially binds a specific protein target, or soluble binding molecules (such as soluble receptors).

A protein-specific binding agent binds substantially only to the defined protein, or to a specific region within the protein. For example, a "specific binding agent" includes antibodies and other agents (such as an aptamer) that bind substantially to a specified polypeptide. The antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: Living multi-cellular vertebrate organisms, a category that includes human and non-human mammals.

Tarpley score (TS): Characterization of severity of the histopathology of Sjögren's syndrome tissue based on salivary gland biopsies, Symptomatic non-Sjögren's syndrome (dry eyes and/or dry mouth, but no histopathological lesions; also referred to as category "C") has a Tarpley score (TS)=0. Early ("E") Sjögren's syndrome (1-2 lymphocytic aggregates per salivary gland lobule, on average) has a TS=1. Intermediate ("I") Sjögren's syndrome (3 lymphocytic aggregates/lobule, on average) has a TS=2, Severe ("S") Sjögren's syndrome has a TS=3-4 (3=diffuse infiltration though acini associated with partial destruction of acinar tissue; 4=diffuse infiltration associated with complete loss of tissue architecture). Sjögren's syndrome lesions categorized as "less severe" or "focal/negligible disease" has a Tarpley score of ≤2, whereas Sjögren's syndrome lesions categorized as having "advanced lesions" or "severe/diffuse disease" has a Tarpley score of TS=$2^+$–4.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

Therapeutically effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

U7 small nuclear RNA (snRNA): An RNA molecule involved in the splicing of histone pre-mRNAs. U7 snRNA, in complex with several proteins (Smith et al., *Proc Natl Acad Sci USA* 88:9784-9788, 1991), forms a ribonucleoprotein particle (U7 snRNP), which is involved in the processing of the 3' end of histone pre-mRNAs. The snRNP contains an RNA region that base pairs with histone pre-mRNA. Methods have been previously described for exchanging the native anti-histone portion of the snRNA with a portion that specifically targets a pre-mRNA of a gene of interest, thereby producing a chimeric snRNA that is capable of specifically interacting with the targeted pre-mRNA. Chimeric snRNAs have been previously used to induce exon skipping and promote alternative splicing (see, for example, U.S. Patent Application Publication No. 2003/0036519; Madocsai et al., *Mol Ther* 12(6):1013-1022, 2005; De Angelis et al., *Proc Natl Acad Sci USA* 99(14):9456-9461, 2002; Goyenvalle et al., *Mol Ther* 17(7):1234-1270, 2009). U7 snRNAs can be designed to target, for example, splice acceptor sites, splice donor sites, branch points and exonic splicing enhancers.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector. In some examples, the viral vector is an AAV vector.

X (inactive)-specific transcript (non-protein coding) (XIST): X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIST gene is expressed exclusively from the XIC of the inactive X chromosome. The transcript is spliced but does not encode a protein. The transcript remains in the nucleus where it coats the inactive X chromosome. XIST is also known as XCE, XIC and SXI1. Genomic and RNA sequences for XIST are publically available, such as in the GenBank database from the National Center for Biotechnology Information. See, for example, Gene ID 7503 for human XIST. An exemplary mRNA sequence for human XIST is set forth herein as SEQ ID NO: 13.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is the finding that Sjögren's syndrome patients exhibit a statistically significant increase in expression of BMP6 in salivary glands compared to healthy control subjects. Also disclosed is the finding that overexpression of BMP6 in the salivary gland increases electrical potential across the salivary gland.

Provided herein is a method of diagnosing a subject as having Sjögren's syndrome, or at risk for developing Sjögren's syndrome by detecting expression of BM6 in a biological sample of the subject. A diagnostically significant increase in expression of BMP6 in the biological sample of the subject relative to a control, diagnoses the subject as having Sjögren's syndrome, or at risk for developing Sjögren's syndrome. In some embodiments, the diagnostically significant increase is an increase of at least 2-fold, at least 3-fold or at least 4-fold relative to the control. In one example, the diagnostically significant increase is an increase of at least 4-fold relative to the control.

In some embodiments, the biological sample is a tissue sample, such as salivary gland tissue (for example, tissue obtained by biopsy of a salivary gland). In some examples, the salivary gland is a minor labial salivary gland, parotid gland or a submandibular gland. In other embodiments, the biological sample is a bodily fluid sample, such as a saliva, tear, blood or serum sample.

In some embodiments, detecting expression of BMP6 in the biological sample comprises measuring the level of BMP6 mRNA in the biological sample. In other embodiments, detecting expression of BMP6 in the biological sample comprises measuring the level of BMP6 protein in the biological sample. Methods for detecting expression of gene products (including mRNA and protein) are well known in the art and a suitable method can be selected based on, for example, the gene product to be detected and the biological sample in which detection is desired. Exemplary methods for detection of gene products are provided below in section IV. In particular examples, the level of BMP6 protein is detecting using an ELISA.

In some embodiments of the disclosed methods, the method further includes measuring electrical potential between a salivary gland of the subject and adjacent tissue. An increase in the measured electrical potential relative to a control, diagnoses the subject as having Sjögren's syndrome, or at risk for developing Sjögren's syndrome.

In some embodiments, the disclosed methods further include providing an appropriate therapy to the subject diagnosed with Sjögren's syndrome. In some examples, the appropriate therapy comprises administering an agent that promotes salivary production, administering a corticosteroid, administering an immunosuppressive drug, administering a non-steroidal anti-inflammatory drug, administering an agent that inhibits expression or activity of BMP6, administering an agent that inhibits BMP signaling, or any combination thereof.

Further provided herein is a method of treating a subject with Sjögren's syndrome by selecting a subject with increased expression of BMP6 in a salivary gland, and administering to the subject a therapeutically effective amount of an agent that inhibits expression or activity of BMP6. Also provided is a method of increasing salivary flow in a subject by selecting a subject with increased expression of BMP6 in a salivary gland and administering to the subject a therapeutically effective amount of an agent that inhibits expression or activity of BMP6. In some embodiments, the salivary gland is a minor labial salivary gland, parotid gland or a submandibular gland.

In some embodiments, the agent that inhibits expression or activity of BMP6 is a BMP6 specific binding agent. In some examples, the specific binding agent specifically binds a BMP6 nucleic acid molecule. In specific non-limiting examples, the specific binding agent comprises a chimeric U7 snRNA or an antisense oligonucleotide that specifically binds a BMP6 nucleic acid molecule. In some cases, the chimeric snRNA comprises a sequence that targets exon 2 or exon 3 of BMP6 pre-mRNA such that binding of the chimeric snRNA induces exon skipping of the BMP6 pre-mRNA. Similarly, in some examples, the antisense oligonucleotide comprises a sequence that targets exon 2 or exon 3 of BMP6 pre-mRNA such that binding of the antisense oligonucleotide induces exon skipping of the BMP6 pre-mRNA. In other examples, the antisense oligonucleotide specifically hybridizes with a BMP6 mRNA and targets the mRNA for degradation.

In some examples, the specific binding agent specifically binds a BMP6 protein. In specific non-limiting examples, the specific binding agent comprises an RNA aptamer, a soluble binding molecule or a single chain antibody that specifically binds a BMP6 protein. In some instances, the soluble binding molecule or single chain antibody is administered by a vector encoding the soluble binding molecule or the single chain antibody. The vector can be any suitable vector for administration of the agent, such as an adeno-associated virus (AAV) vector or an adenovirus vector.

In some examples, the soluble binding molecule is a soluble BMP6 receptor, sHJV, NOGGIN, or BAMBI. In specific non-limiting examples, (i) the amino acid sequence of sHJV is at least 85%, at least 90%, at least 95%, at least 96%, at least 97%, at least 98% or at least 99% identical to residues 35-426 of SEQ ID NO: 6 or residues 35-332 of SEQ ID NO: 6; (ii) the amino acid sequence of BAMBI is at least 85%, at least 90%, at least 95%, at least 96%, at least 97%, at least 98% or at least 99% identical to SEQ ID NO: 8 or residues 2-152 of SEQ ID NO: 8; (iii) the amino acid sequence of sclerostin is at least 85%, at least 90%, at least 95%, at least 96%, at least 97%, at least 98% or at least 99% identical to SEQ ID NO: 10; or (iv) the amino acid sequence of noggin is at least 85%, at least 90%, at least 95%, at least 96%, at least 97%, at least 98% or at least 99% identical to SEQ ID NO: 12. In other non-limiting examples, the (i) the amino acid sequence of sHJV comprises or consists of residues 35-426 of SEQ ID NO: 6 or residues 35-332 of SEQ ID NO: 6; (ii) the amino acid sequence of BAMBI comprises or consists of SEQ ID NO: 8 or comprises or consists of residues 2-152 of SEQ ID NO: 8; (iii) the amino acid sequence of sclerostin comprises or consists of SEQ ID NO: 10; or (iv) the amino acid sequence of noggin comprises or consists of SEQ ID NO: 12.

In some embodiments, the agent that inhibits BMP signaling is a small molecule inhibitor. In particular examples, the small molecular inhibitor is dorsomorphin In some embodiments, the agent that inhibits expression or activity of BMP6, or inhibits BMP signaling, is administered locally to the salivary gland. In other embodiments, the agent that inhibits expression or activity of BMP6, or inhibits BMP signaling, is administered systemically.

Further provided herein is a method of diagnosing a subject as having Sjögren's syndrome by measuring electrical potential in a salivary gland of the subject. A diagnostically significant increase in electrical potential between the salivary gland and adjacent oral mucosa of the subject relative to a control, diagnoses the subject as having Sjögren's syndrome. In some embodiments, the diagnostically significant increase is at least 10%, at least 20%, at least 30%, at least 40%, at least 50%, at least 60%, at least 70% or at least 80%. In some embodiments, the diagnostically significant increase is at least 1 or at least 2 standard deviations beyond the mean electrical potential for healthy control subjects. A change in electrical potential can also be assessed indirectly since electrical potential (V) is related to current (I) and resistance (R) by the equation V=IR. Hence, changes in voltage can be determined by measuring changes in current and/or resistance in the tissue current measurement established by the electrodes.

In some embodiments, the salivary gland is the submandibular gland or the parotid gland.

In some embodiments, the method further includes providing an appropriate therapy to the subject diagnosed with Sjögren's syndrome. In some examples, the appropriate therapy comprises administering an agent that promotes salivary production, administering a corticosteroid, administering an immunosuppressive drug, administering a non-steroidal anti-inflammatory drug, administering an agent that inhibits expression or activity of BMP6, administering an agent that inhibits BMP signaling, or any combination thereof.

In some embodiments, the method further includes measuring electrophysiologic tissue characteristics associated with Sjögren's syndrome. For example, tissue impedance or electrical potential differences are measured in a salivary gland using a device, wherein the device comprises a voltmeter, a detection electrode and a reference electrode, wherein the detection electrode comprises a cannula having a tip of a diameter suitable for insertion into the duct of a salivary gland, the reference electrode is suitable for attachment to tissue external and adjacent to the duct of the salivary gland, and the detection and reference electrodes establish a conductive pathway for an electrical diagnostic current and determination of a voltage difference or tissue impedance between the detection and reference electrodes. In some examples, the conductive pathway comprises in part a liquid pathway. In particular examples, the conductive pathway further comprises a cannula suitable for insertion into the salivary gland and a liquid-filled syringe that provides a source of liquid for injection into the cannula, whereby the liquid at least partially establishes electrical current between the salivary gland and detection electrode.

In particular embodiments, the reference electrode is placed on oral mucosa less than 5 cm from the detection electrode, for example the reference and detection electrodes are placed 0.1 to 5 cm apart. In other embodiments, the electrodes are separated by at least 0.1, or 0.3 cm, but are no more than 5 cm, no more than 4 cm, no more than 3 cm, no more than 2 cm or no more than 1 cm apart, for example, a separation distance of 0.1 to 1 cm, or 0.3 to 0.5 cm. Although the distances can vary within these ranges, the absolute value of electrophysiologic tissue measurements could be affected by different distances between the electrodes. Hence control values and measurements to which they are compared are ideally made using substantially uniform distances between the detection and reference electrodes to assure consistency of output readings. Similarly, electrode separation distances in a given patient or patient population are ideally maintained at a consistent distance from one another to assure the most accurate comparison of values.

Also provided herein is a device for measuring electrical potential in a salivary gland, comprising a voltmeter, a detection electrode and a reference electrode, wherein the reference electrode comprises a cannula having a tip of a diameter suitable for insertion into the duct of a salivary gland, the reference electrode is suitable for attachment to tissue external and adjacent to the duct of the salivary gland, and the detection and reference electrodes establish a conductive pathway for an electrical current and determination of a voltage difference between the detection and reference electrodes. In some embodiments, the conductive pathway comprises in part a liquid pathway. In particular examples, the conductive pathway further comprises a cannula suitable for insertion into the salivary gland and a liquid-filled syringe that provides a source of liquid for injection into the cannula, whereby the liquid at least partially establishes electrical current between the salivary gland and detection electrode.

Further provided is a method for diagnosing a dry mouth syndrome in a subject by measuring electrical potential of a salivary gland of the subject using the device disclosed herein, wherein an increase in electrical potential across the electrodes indicates that the subject has a dry mouth syndrome. In some examples, the dry mouth syndrome is Sjögren's syndrome.

The present disclosure also describes the finding that male Sjögren's syndrome patients express XIST, a non-coding RNA that is not usually expressed in males. Also described is the finding that male Sjögren's syndrome patients down-regulate MECP2 compared with male controls.

Thus, provided herein is a method of diagnosing a male subject as having Sjögren's syndrome, or at risk for developing Sjögren's syndrome, by detecting expression of XIST, MECP2, or both, in a biological sample of the subject. A diagnostically significant increase in expression of XIST, a diagnostically significant decrease in expression of MECP2, or both, in the biological sample of the male subject relative to a control, diagnoses the subject as having Sjögren's syndrome, or at risk for developing Sjögren's syndrome.

In some embodiments, detecting expression of XIST comprises detecting the presence of exon 6 of XIST.

In some embodiments, the diagnostically significant increase in XIST expression is an increase of at least 2-fold, at least 3-fold, at least 4-fold, at least 5-fold, at least 6-fold, at least 7-fold, at least 8-fold, at least 9-fold or at least 10-fold relative to the control; or the diagnostically significant decrease in MECP2 expression is at least 1.5-fold, at least 2-fold, at least 2.5-fold, at least 3-fold, at least 4-fold or at least 5-fold; or both. In specific examples, the diagnostically significant increase in expression of XIST is an increase of at least 2-fold relative to the control. In other specific examples, the diagnostically significant decrease in expression of MECP2 is at least 2-fold relative to the control.

In some embodiments, the biological sample is a tissue sample, such as salivary gland tissue (for example, tissue obtained by biopsy of a salivary gland). In some examples, the salivary gland is a minor salivary gland. In other embodiments, the biological sample is a bodily fluid sample, such as a saliva, tear, blood or serum sample.

In some embodiments, detecting expression of XIST or MECP2 in the biological sample comprises measuring the level of XIST or MECP2 RNA in the biological sample. In other embodiments, detecting expression of MECP2 in the biological sample comprises measuring the level of MECP2 protein in the biological sample. Methods for detecting expression of gene products (including RNA and protein) are well known in the art and a suitable method can be selected based on, for example, the gene product to be detected and the biological sample in which detection is desired. Exemplary methods for detection of gene products are provided below in section IV.

In some embodiments of the disclosed methods for diagnosing a male subject with Sjögren's syndrome, the method further includes measuring electrical potential in a salivary gland of the subject. An increase in electrical potential in the salivary gland of the subject relative to a control, diagnoses the male subject as having Sjögren's syndrome, or at risk for developing Sjögren's syndrome.

In some embodiments, the disclosed methods further include providing an appropriate therapy to the male subject diagnosed with Sjögren's syndrome. In some examples, the appropriate therapy comprises administering an agent that promotes salivary production, administering a corticosteroid, administering an immunosuppressive drug, administering a non-steroidal anti-inflammatory drug, administering an agent that inhibits expression or activity of BMP6, administering an agent that inhibits BMP signaling, administering an agent that inhibits expression of XIST, administering a nucleic acid molecule encoding MECP2, or any combination thereof.

Further provided are methods of treating a male subject with Sjögren's syndrome by selecting a male subject with increased expression of XIST and/or decreased expression of MECP2, and (i) administering to the subject a therapeutically effective amount of an agent that inhibits expression of XIST, or (ii) administering to the subject a therapeutically effective amount of nucleic acid molecule encoding MECP2, or both (i) and (ii).

Also provided are methods of increasing salivary flow in a male subject by selecting a subject with increased expression of XIST and/or decreased expression of MECP2, and administering to the subject (i) a therapeutically effective amount of an agent that inhibits expression of XIST, or (ii) a therapeutically effective amount of a nucleic acid molecule encoding MECP2 (such as a vector encoding MECP2), or both (i) and (ii).

Exemplary XIST inhibitors include, for example, antisense oligonucleotides or siRNA molecules that specifically hybridize with a XIST nucleic acid molecule. XIST nucleic acid sequences are publically available, such as the human XIST RNA sequence deposited under GenBank™ Accession No. NR_001564. Appropriate antisense oligonucleotides or siRNAs targeting XIST can be designed by one of skill in the art using publically available XIST sequences. The XIST antisense transcript Tsix is a known inhibitor of XIST (Senner and Brockdorff, *Curr Opin Genet Dev* 19(2): 122-126, 2009; Stavropoulos et al., *Proc Natl Acad Sci USA* 98(18):10232-10237, 2001) that can be used with the disclosed methods. Tsix nucleic acid sequences are publically available, such as the human Tsix transcript deposited under GenBank™ Accession No. NR_003255.

As described herein, significant alterations in sex-chromosome gene expression were identified in male SS patients, including XIST expression, decreased MECP2 expression and apparent silencing of Y-chromosome gene expression. This gene expression pattern, called Autoimmune Xist Y-chromosome Inactivation Syndrome (AXYIS), was also identified in affected tissues from males diagnosed with autoimmune diseases associated with pSS, including rheumatoid arthritis, type II diabetes mellitus, systemic sclerosis and lymphoma.

In particular, described herein is the finding that in a subset of male Sjögren's syndrome patients, Y-chromosome gene expression is down-regulated (for example, expression of the genes RPS4Y1, RPS4Y2, JARID1D, CYORF15B and CYORF14 is down-regulated), as is expression of ribosomal proteins that regulate RNA processing and viral replication (e.g., RPS4Y1, RPS4Y2 and RPS4X), and proteins that regulate DNA methylation (such as MDB6 and NASP). In addition, a significant number of duplications and/or deletions were identified in the opsin (OPN1LW, OPN1MW and OPN1MW2) and tex28 region of the X-chromosomes of male patients with Sjögren's syndrome. These findings provide additional markers that can be utilized for the diagnosis and treatment of Sjögren's syndrome in men.

IV. Methods of Detecting Gene Expression Changes for Diagnosis of Sjögren's Syndrome Although detecting expression of BMP6, XIST and MECP2 is specifically discussed below, the techniques and methods described in this section can be applied to any gene, including any gene linked to SS as described herein.

Provided herein are methods of diagnosing a subject as having Sjögren's syndrome, or at risk for developing Sjögren's syndrome, by detecting expression of BMP6 in a biological sample (such as a salivary gland sample) of a subject. A diagnostically significant increase in expression of BMP6 in the biological sample compared with a control (such as a sample from the healthy control or a reference value) indicates the subject has Sjögren's syndrome, or is at risk for developing Sjögren's syndrome.

Further provided herein is a method of diagnosing a male subject as having Sjögren's syndrome, or at risk for developing Sjögren's syndrome, by detecting expression of XIST, MECP2, or both, in a biological sample of the subject. A diagnostically significant increase in expression of XIST, a diagnostically significant decrease in expression of MECP2, or both, in the biological sample of the male subject relative to a control, diagnoses the subject as having Sjögren's syndrome, or at risk for developing Sjögren's syndrome.

As described below, expression of BMP6, XIST and/or MECP2 can be detected using any one of a number of methods well known in the art. Expression of either mRNA (for BMP6, XIST and MECP2) or protein (for BMP6 and MECP2) is contemplated herein.

A. Methods for Detection of mRNA

In some embodiments, RNA is isolated from a sample of a subject, such as a fluid sample or tissue sample (such as salivary gland biopsy). General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., *BioTechniques* 18:42044 (1995). In one example, RNA isolation can be performed using a purification kit, buffer set and protease from commercial manufacturers. Total RNA from tissue samples can be isolated, for example, using RNeasy Mini Kit (Qiagen) or RNA Stat-60 (Tel-Test). RNA prepared from salivary gland or other biological sample can be isolated, for example, by cesium chloride density gradient centrifugation.

Methods of gene expression analysis include methods based on hybridization of polynucleotides, methods based on sequencing of polynucleotides, and proteomics-based methods. In some examples, mRNA expression in a sample is quantified using northern blotting or in situ hybridization (Parker & Barnes, Methods in Molecular Biology 106:247-283, 1999); RNAse protection assays (Hod, *Biotechniques* 13:852-4, 1992); or PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, such as in normal and Sjögren's Syndrome tissue samples to characterize patterns of gene expression.

Methods for quantitating mRNA are well known in the art. In one example, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV- RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, in some examples it typically employs the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System® (Perkin-Elmer-Applied Biosystems, Foster City, Calif.), or Lightcycler (Roche Molecular Biochemicals, Mannheim, Germany). In one example, the 5' nuclease procedure is run on a real-time quantitative PCR device such as the ABI PRISM 7700® Sequence Detection System®. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

A variation of RT-PCR is real time quantitative RT-PCR, which measures PCR product accumulation through a dual-labeled fluorogenic probe (e.g. TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., Genome Research 6:986 994, 1996). Quantitative PCR is also described in U.S. Pat. No. 5,538,848. Related probes and quantitative amplification procedures are described in U.S. Pat. Nos. 5,716,784 and 5,723,591.

The steps of a representative protocol for quantitating gene expression using fixed, paraffin-embedded tissues as the RNA source, including mRNA isolation, purification, primer extension and amplification are given in various published journal articles (see Godfrey et al., *J. Mol. Diag.* 2:84-91, 2000; Specht et al., *Am. J. Pathol.* 158:419-429, 2001).

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "housekeeping" gene or "internal control" can also be evaluated. These terms include any constitutively or globally expressed gene whose presence enables an assessment of mRNA levels. Such an assessment includes a determination of the overall constitutive level of gene transcription and a control for variations in RNA recovery.

In some examples, gene expression is identified or confirmed using the microarray technique. Thus, the expression profile can be measured in either fresh or paraffin-embedded tissue or cells, using microarray technology. In this method, BMP6 nucleic acid sequences of interest (including cDNAs and cRNAs) are plated, or arrayed, on a microchip substrate. The arrayed sequences are then hybridized with specific DNA probes from cells or tissues of interest.

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-487, 1995; and Velculescu et al., *Cell* 88:243-251, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH).

Sample cells or tissues are treated to increase their permeability to allow a probe to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a salivary gland biopsy. Since the sequences of the genes of interest are known, probes can be designed accordingly such that the probes specifically bind the gene of interest.

B. Methods for Detection of Protein

In some examples, expression of BMP6 or MECP2 protein is analyzed in a sample obtained from a subject, such as a blood sample or a tissue sample (such as a salivary gland sample). In some embodiments, an increase in the amount of BMP6 protein in the sample relative to a control (such as a sample from a healthy subject or a standard value) allows for diagnosis of Sjögren's syndrome in a subject. In some embodiments, a decrease in the amount of MECP2 protein in the sample relative to a control (such as a sample from a healthy subject or a standard value) allows for diagnosis of Sjögren's syndrome in a male subject.

Antibodies specific to BMP6 or MECP2 protein can be used for the detection and quantitation of BMP6 or MECP2 by one of a number of immunoassay methods that are well known in the art, such as those presented in Harlow and Lane (*Antibodies, A Laboratory Manual*, CSHL, New York, 1988). Methods of constructing such antibodies are known in the art. Alternatively, BMP6-specific or MECP2-specific antibodies can be obtained from commercially or publically available sources.

Any standard immunoassay format (such as ELISA, Western blot, or RIA assay) can be used to measure protein levels. Thus, BMP6 or MECP2 protein levels in a sample can readily be evaluated using these methods Immunohistochemical techniques can also be utilized for BMP6 or MECP2 protein detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating BMP6 or MECP2 protein, a biological sample (such as a salivary gland tissues sample) of the subject that includes cellular proteins can be used. Quantitation of BMP6 or MECP2 protein can be achieved by immunoassay. The amount of BMP6 or MECP2 protein can be assessed in a sample obtained a test subject, and in some cases, in a sample obtained from a healthy subject. A significant increase or decrease in the amount can be evaluated using statistical methods disclosed herein and/ or known in the art.

Quantitative spectroscopic approaches methods, such as SELDI, can be used to analyze BMP6 or MECP2 protein expression in a sample. In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

C. Obtaining and Processing Biological Samples

The methods disclosed herein include detecting BMP6, XIST or MECP2 expression in a biological sample obtained from a test subject. In some embodiments, the biological sample is a tissue sample, such as a salivary gland sample. In other embodiments, the biological sample includes saliva, tears, blood, serum or plasma.

Example 1 below provides an exemplary method for processing a biological sample to detect expression level of BMP6 when the biological sample is a salivary gland biopsy. In one non-limiting embodiment of the present disclosure, a salivary gland is obtained from a test subject and stored in RNAlater (Qiagen, Valencia, Calif.) until RNA extraction. The sample is homogenized, such as with a Bullet-Blender Homogenizer (Next Advance Inc., Averill Park, N.Y.) or with another homogenizer (OMNI-Th Internationals Inc.). The tissue is mixed with autoclaved, RNALater-soaked stainless beads containing QIAzol lysis reagent (Qiagen), homogenized for an appropriate length of time (such as about 2 minutes), and placed on ice. The total RNA is extracted with an RNeasy Mini Kit (Qiagen).

Biological samples can be obtained using either invasive or non-invasive procedures. One non-limiting example of an invasive procedure includes a biopsy, such as a biopsy of salivary gland or lacrimal gland tissue. A specific, non-limiting example of a non-invasive procedure includes obtaining a sample of saliva from the mouth or tears from the eye of a subject using a syringe, a pipette, or absorbent paper.

D. Output Devices for Diagnostic Results

Gene expression can be evaluated using any technique described above, or any other method known in the art. As described herein, gene expression can be measured, for example, using labeled probes that can be detected using standard equipment. For example, gene expression measurements using microarray or RT-PCR (which typically use labeled probes specific for a gene product) can be quantitated using a microarray scanner or other suitable scanner for detecting the label. In addition, mutations in a gene or corresponding mRNA can be detected by direct sequencing of a nucleic acid molecule, detection of an amplification product, microarray analysis or any other DNA/RNA hybridization platform. For detection of mutant proteins, an immunoassay, biochemical assay or microarray can be used.

The diagnostic results of gene expression and mutation analyses can be transmitted using any one of a number of output devices or formats known in the art. For example, the output device can be a visual output device, such as a computer screen or a printed piece of paper. In other examples, the output device can be an auditory output device, such as a speaker. In other examples, the output device is a printer. In some cases, the diagnostic results are recorded in a patient's printed or electronic medical record.

Visualization methods such as autoradiography, or fluorometric or colorimetric reactions can be used to detect or measure a change in the level of any gene product in a sample. Autoradiographic, fluorometric, or colorimetric reactions can be quantitated using, for instance, a spectrophotometer, a scintillation counter, a densitometer or a Phosphorimager (Amersham Biosciences). The Phosphorimager is able to analyze both DNA and protein samples from blots and gels using autoradiographic, direct fluorescence or chemifluorescence detection. Since the Phosphorimager is more sensitive than ordinary x-ray film, exposure times can be reduced up to ten-fold and signal quantitation of both weak and strong signals on the same blot is possible. Images can be visualized and evaluated, for example, with the aid of computer programs such as ImageQuant™.

E. Other Methods for Sjögren's Syndrome Diagnosis

In some embodiments of the diagnostic methods disclosed herein, if the diagnostic test indicates the subject has Sjögren's syndrome, or is susceptible to developing Sjögren's syndrome, the subject is subjected to additional diagnostic tests to confirm the diagnosis by other means. Alternatively, the test is used to confirm a diagnosis already indicated by other means.

Any one of a number of means known in the art of diagnosing a subject with Sjögren's syndrome can be used. Other means of diagnosing Sjögren's syndrome, or confirming a diagnosis of Sjögren's syndrome, can include one or more of: (i) ocular symptoms (for example, persistent dry eyes and/or recurrent sensation of sand or gravel in eyes); (ii) oral symptoms (for example, daily feeling of dry mouth, persistently swollen salivary glands, and/or drinking liquids to swallow dry food); (iii) objective evidence of ocular involvement defined as a positive result of a Schirmer's test performed without anesthesia (≤5 mm in 5 minutes) and/or Rose bengal score or other ocular surface staining score (≥4 according to van Bijsterveld's scoring system; (iv) histopathology in minor salivary glands (measuring focus score or Tarpley score); (v) salivary gland involvement demonstrated with objective evidence of salivary gland involvement by a positive result for unstimulated whole salivary flow (≤1.5 ml in 15 minutes), parotid sialography showing the presence of diffuse sialectasias (punctate, cavitary, or destructive pattern) without evidence of obstruction in the major ducts, and/or salivary scintigraphy showing delayed uptake, reduced concentration and/or delayed excretion of tracer; and/or (vi) autoantibodies (presence in the serum of antibodies to Ro (SSA) or La (SSB) antigens, or both. The additional diagnostic parameters can also include the measurement of electrophysiologic tissue characteristics, as described in section V.

V. Methods of Measuring Electrophysiologic Changes in the Salivary Gland for the Diagnosis of Sjögren's Syndrome Described herein is the finding that Sjögren's syndrome and/or overexpression of BMP6 in the salivary gland results in tissue changes that affect electrophysiologic characteristics of the tissue, such as an increase in electrical potential between the salivary gland and surrounding oral mucosa. Accordingly, provided herein is a method of diagnosing a subject as having Sjögren's syndrome by measuring electrophysiologic parameters, such as the electrical potential or impedance in the measuring circuit. For example, a diagnostically significant increase in the electrical potential in the measuring circuit of the subject relative to a control, diagnoses the subject as having Sjögren's syndrome. In some embodiments, the diagnostically significant increase is at least 10%, at least 20%, at least 30%, at least 40%, at least 50%, at least 60%, at least 70% or at least 80%. In some embodiments, the diagnostically significant increase is at least 1 or at least 2 standard deviations beyond the mean electrical potential for healthy control subjects. Changes in tissue impedance or electrical potential in the same patient over time can be used to measure progression of disease or response to therapy. For example, a relative increase in tissue impedance of electrical potential (compared to an initial baseline measurement) over time indicates worsening disease in the subject. Conversely, a decrease in tissue impedance or electrical potential (compared to an initial baseline measurement) over time indicates the patient is improving, for example, in response to therapy.

The salivary gland measuring circuit in which electrical potential is measured can be any salivary gland suitable for measurement of electrical potential using a device that can make such measurements, such as the device disclosed herein. Measuring circuit devices for measuring voltage differences and impedance in tissue are well known, and are disclosed for example in U.S. Pat. Nos. 7,729,756; 7,925,340; and 6,364,844; and in U.S. Patent Application Publication No. 2003/0009110, and any such suitable device can be used to monitor the changes in the measuring circuit disclosed herein. In some embodiments, the salivary gland is the submandibular gland or the parotid gland. If electrical potential is measured in a SMG, the detection electrode can be inserted into Wharton's duct; or if electrical potential is measured in a parotid gland, the detection electrode can be inserted into Stensen's duct. The reference electrode is place on adjacent tissue, such as 0.1 to 5 cm (for example, 0.1 to 1 cm, or 0.3 to 0.5 cm) away from the detection electrode.

In some embodiments, the method further includes providing an appropriate therapy to the subject diagnosed with Sjögren's syndrome. In some examples, the appropriate therapy comprises administering an agent that promotes salivary production, administering a corticosteroid, administering an immunosuppressive drug, administering a non-steroidal anti-inflammatory drug, administering an agent that inhibits expression or activity of BMP6, administering an agent that inhibits BMP signaling, or any combination thereof. The measuring circuit can also be used to monitor response to therapy.

In some embodiments, the method further includes using the measuring circuit by measuring electrical potential using a device that includes a voltmeter, a detection electrode and a reference electrode, wherein the detection electrode comprises a cannula having a tip of a diameter suitable for insertion into the duct of a salivary gland, the reference electrode is suitable for attachment to tissue (such as oral mucosa) external and adjacent to the duct of the salivary gland, and the detection and reference electrodes establish a conductive pathway for an electrical current and determination of a voltage difference or tissue impedance between the detection and reference electrodes. In some examples, the conductive pathway comprises in part a liquid pathway. In particular examples, the conductive pathway further comprises a cannula suitable for insertion into the salivary gland and a liquid-filled syringe that provides a source of liquid for injection into the cannula, whereby the liquid at least partially establishes electrical current between the salivary gland and detection electrode.

VI. Methods for the Treatment of Sjögren's Syndrome

Provided herein are methods of treating Sjögren's syndrome in a subject in need of treatment (such as a subject with increased expression of BMP6 in a salivary gland), by administering to the subject an agent that inhibits BMP6, such as a compound that inhibits expression (mRNA or protein expression) or at least one biological activity of BMP6. The agent can also be an agent that inhibits BMP signaling, such as the small molecule inhibitor dorsomorphin.

An agent that inhibits expression or activity of BMP6 can be any type of compound, such as, but not limited to, a nucleic acid molecule (such as an antisense oligonucleotide, an siRNA, an RNA aptamers, a U7 RNA that induces exon skipping, a vector encoding a single chain antibody or a vector encoding a soluble form of the BMP6 receptor), a polypeptide, an antibody, or small molecule, that is capable of inhibiting expression or activity of BMP6. Such agents can be produced chemically or biologically, or can be expressed from a recombinant plasmid or viral vector using any method known in the art. Provided below are exemplary agents that can be used to inhibit expression of BMP6.

In other embodiments, provided herein is a method of treating a male subject diagnosed with Sjögren's syndrome by selecting a male subject with increased expression of XIST, decreased expression of MECP2, or both, relative to a control, and administering to the subject a therapeutically effective amount of an agent that inhibits expression of XIST, or a therapeutically effective amount of a nucleic acid molecule encoding MECP2. Exemplary XIST inhibitors include, for example, antisense oligonucleotides or siRNA molecules that specifically hybridize with a XIST nucleic acid molecule. XIST nucleic acid sequences are publically available, such as the human XIST RNA sequence deposited under GenBank™ Accession No. NR_001564. Appropriate antisense oligonucleotides or siRNAs targeting XIST can be designed by one of skill in the art using publically available XIST sequences. The XIST antisense transcript Tsix is a known inhibitor of XIST (Senner and Brockdorff, *Curr Opin Genet Dev* 19(2):122-126, 2009; Stavropoulos et al., *Proc Natl Acad Sci USA* 98(18):10232-10237, 2001) that can be used with the disclosed methods. Tsix nucleic acid sequences are publically available, such as the human Tsix transcript deposited under GenBank™ Accession No. NR_003255.

A. Chimeric U7 snRNA Targeting BMP6

Chimeric U7 snRNAs can be generated that specifically target BMP6 pre-mRNA to induce exon skipping, thereby producing a BMP6 protein that functions as a dominant negative. The dominant negative form of BMP6 acts an inhibitor of BMP6 activity, therefore the chimeric U7 snRNA targeting BMP6 can be used as a therapeutic for the treatment of Sjögren's syndrome. In some examples, the chimeric snRNA targets exon 2 or exon 3 of BMP6 to produce the dominant negative form of the protein. One of skill in the art can design appropriate snRNAs to contain sequence that is complementary to the BMP6 pre-mRNA using publically available BMP6 sequences. Methods of making chimeric U7 snRNAs has been previously described in the art (see, for example, Goyenvalle et al., *Mol Ther* 17(7):1234-1240, 2009; De Angelis et al., *Proc Natl Acad Sci USA* 99(14):9456-9461, 2002; Madocsai et al., *Mol Ther* 12(6):1013-1022, 2005).

B. Antisense Oligonucleotides Targeting BMP6 or XIST

Antisense oligonucleotides specific for BMP6 or XIST nucleic acid molecules can also designed to either modulate splicing (including induce exon skipping) or can be designed to decrease overall transcript levels. Using publically available nucleic acid sequences, it is within the capability of one of skill in the art to design an antisense oligonucleotide, including appropriate modifications, to either modulate splicing (see, for example, U.S. Patent Application Publication No. 2010/0216238), or to target the BMP6 or XIST mRNA to degradation by RNaseH. In some examples in which the antisense oligonucleotide is designed to modulate splicing of BMP6, the antisense oligonucleotide is designed to target exon 2 or exon 3 of BMP6 to result in the production of a dominant negative form of the BMP6 protein. XIST nucleic acid sequences are publically available, such as the human XIST RNA sequence deposited under GenBank™ NR_001564.

C. RNA Aptamers Specific for BMP6

Nucleic acid aptamers are molecules that bind to a specific target molecule. Aptamers can be selected or designed to bind a variety of different types of molecular targets, including small molecules, proteins, nucleic acids, cells or tissues. Aptamers, such as RNA aptamers, can be designed or selected that specifically bind BMP6 protein and thereby inhibit its activity. Thus, RNA aptamers specific for BMP6 protein can be used for the treatment of Sjögren's syndrome. Methods of selecting RNA aptamers that specifically bind a target protein are known in the art, including SELEX (Systematic Evolution of Ligands by Exponential Enrichment).

D. Soluble Binding Molecules Specific for BMP6

A number of molecules that specifically bind BMP6 are known in the art. Some of these are soluble proteins or can be produced in a soluble form, such as by removal of the extracellular domain. Soluble binding proteins specific for BMP6 protein act as decoy molecules to prevent BMP6 from binding to native receptors or other proteins and thereby inhibit BMP6 activity. Examples of soluble binding molecules specific for BMP6 include, for example, sHJV, BAMBI, noggin, follistatin, chordin, BMPER and sclerostin. Each of these proteins, or fragments thereof, can be used to inhibit activity of BMP6 and can therefore be used as therapeutic agents for the treatment of Sjögren's syndrome.

E. BMP6-specific Single Chain Antibody

Antibodies specific for BMP6 can also be used to inhibit the activity of BMP6 protein and can therefore be utilized as therapeutic agents for the treatment of Sjögren's syndrome. In some embodiments, the antibody is a single chain antibody. However, other antibody fragments useful as therapeutic agents are well known in the art. Methods of making single-chain antibodies and other antibody fragments are well known in the art. It is also within the capabilities of one of skill in the art to generate monoclonal antibodies specific for BMP6 according to standard procedures.

F. Vectors for Administration of Therapeutic Agents

The therapeutic agents contemplated herein (such as the soluble BMP6 binding molecule, BMP6-specific single chain antibodies or nucleic acid molecules encoding MECP2) can also be expressed from a recombinant viral vector. Genomic, mRNA and protein sequences for MECP2 are publically available, such as in the GenBank database from the National Center for Biotechnology Information (see, for example, Gene ID 4204 for human MECP2). Exemplary mRNA and protein sequences for human MECP2 are set forth herein as SEQ ID NOs: 14 and 15.

The recombinant viral vectors of use with the disclosed methods include sequences encoding the therapeutic products and any suitable promoter for expressing the RNA sequences. Suitable promoters include, but are not limited to, the U6 or H1 RNA pol III promoter sequences, or a cytomegalovirus promoter. Selection of other suitable promoters is within the skill in the art. The recombinant viral vectors of the present disclosure can also comprise inducible or regulatable promoters for expression of the gene products.

Suitable viral vectors include, but are not limited to, adeno-associated virus vectors, adenovirus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Douglas and Curiel, *Science and Medicine*, March/April 1997, pages 44-53; Zern and Kresinam, *Hepatology* 25(2), 484-491, 1997). Representative adenoviral vectors which can be used for the methods provided herein are described by Stratford-Perricaudet et al. (*J. Clin. Invest.* 90: 626-630, 1992); Graham and Prevec (In Methods in Molecular Biology: Gene Transfer and Expression Protocols 7: 109-128, 1991); and Barr et al. (*Gene Therapy,* 2:151-155, 1995).

Adeno-associated virus (AAV) vectors also are suitable for administration of therapeutic agents. Methods of generating AAV vectors, administration of AAV vectors and their use are well known in the art (see, for example, U.S. Pat. No. 6,951,753; U.S. Patent Application Publication Nos. 2007-036757, 2006-205079, 2005-163756, 2005-002908; and PCT Publication Nos. WO 2005/116224 and WO 2006/119458).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Suitable herpesvirus vectors can be derived from any one of a number of different types of herpesviruses, including, but not limited to, herpes simplex virus-1 (HSV-1), HSV-2 and herpesvirus saimiri Recombinant herpesvirus vectors, their construction and uses are well described in the art (see, for example, U.S. Pat. Nos. 6,951,753; 6,379,6741 6,613,892; 6,692,955; 6,344,445; 6,319,703; and 6,261,552; and U.S. Patent Application Publication No. 2003-0083289).

G. Administration of Therapeutic Agents

As used herein, a therapeutically effective amount of a compound that inhibits expression or activity of BMP6, or inhibits expression or activity of XIST, is an amount sufficient to result in a biological effect (such as alleviating one or more signs or symptoms of Sjögren's syndrome). For example, the agent can decrease the expression level or biological activity of BMP6 or XIST (or any other gene upregulated in patients with Sjögren's syndrome) by a desired amount, for example by at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value.

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject an agent that inhibits expression or activity of BMP6 or XIST.

For example, an effective amount of a BMP6 or XIST inhibitor can be based on the approximate body weight of a subject to be treated. Such effective amounts can be administered by any suitable route, such as, for example, intravenously or locally into the salivary gland. In some examples, a therapeutically effective amount of the therapeutic agent that is administered to a subject can range from about 5 to about 3000 micrograms/kg of body weight, from about 700 to about 1000 micrograms/kg of body weight, or greater than about 1000 micrograms/kg of body weight, depending on the type of compound being administered and the route of administration.

One skilled in the art can also readily determine an appropriate dosage regimen for the administration of a therapeutic agent disclosed herein to a given subject. For example, a therapeutic agent can be administered to the subject once (e.g., as a single injection or deposition). Alternatively, a therapeutic agent can be administered once or twice daily to a subject for a period of from about three to about twenty-eight days, more particularly from about seven to about ten days.

Therapeutic agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the therapeutic agent. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local (such as directly into the salivary gland). In some embodiments of the present disclosure, administration occurs by directly delivery to the salivary gland, such as by retrograde instillation.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some embodiments, a single agent that inhibits the expression or activity of BMP6 or XIST is administered to the subject in need of treatment. In other embodiments, two or more agents (such as 2, 3, 4, 5, or more) that inhibit expression or activity of BMP6 or XIST are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

In some embodiments, an agent that inhibits expression or activity of BMP6 or XIST can be administered to a subject in combination with one or more additional treatments for Sjögren's syndrome. Exemplary Sjögren's syndrome treatments include, but are not limited to, administration of agents that promote salivary production (such as pilocarpine or cevimeline), moisture replacement therapies (such as eye drops), or administration of NSAIDS or corticosteroids, or other immunosuppressive or immunomodulatory drugs.

The following examples are provided to illustrate certain particular features and/or embodiments. These examples should not be construed to limit the disclosure to the particular features or embodiments described.

EXAMPLES

Example 1

Overexpression of BMP6 Leads to Loss of Salivary Gland Activity in Sjögren's Syndrome Patients and Mice This example describes the finding that expression of BMP6 is significantly increased in patients with Sjögren's syndrome, relative to healthy controls. In addition, overexpression of BMP6 locally in the salivary glands of mice results in the loss of salivary gland fluid secretion as well as changes in the connective tissue of the gland.
Materials and Methods
Patient Selection Criteria A subset of five female patients with primary Sjögren's Syndrome in accordance with the European-American consensus group criteria (Vitali, Bombardieri et al., *Ann. Rheum. Dis.* 61, 554-558, 2002) were selected for microarray analysis along with five age-matched healthy female volunteers. The patients used in the present analysis were all chosen based on low lymphocytic scores (FS of ≤2) and low stimulated salivary flow. The clinical features of the selected study subjects are summarized in Table 1.
RNA Extraction and Amplification, Synthesis of Fluorescent cRNA RNA extraction: Minor labial salivary glands were obtained from participants in the study and stored thereafter in RNAlater (Qiagen, Valencia, Calif.) until RNA extraction. Samples were homogenized with a Bullet-Blender Homogenizer (Next Advance Inc., Averill Park, N.Y.) or by homogenization with a homogenizer (OMNI-Th Internationals Inc). Briefly, the tissue was mixed with autoclaved, RNALater-soaked 0.5 mm stainless beads in a tube containing 600 µl of the QIAzol lysis reagent (Qiagen), homogenized for 2 minutes, and placed on ice afterwards. The total RNA was extracted with an RNeasy Mini Kit (Qiagen) according to the manufacturer's recommendations. The quality of RNA was measured with use of a 2100 Bioanalyzer (Agilent Technologies, Palo Alto, Calif.). Only RNA with a 28S/18S ribosomal RNA ratio of 1.7 with RNA integrity number (RIN) score >6.5 or greater was used for the arrays generated for the following steps of the microarray.

cRNA labeling: Total RNA from both patient and healthy volunteer samples were amplified and labeled with a low RNA input linear amplification kit (Agilent). A total of 500 ng RNA was labeled with Cyanine 3-CTP according to the manufacturer's instructions. Briefly, 500 ng of total RNA was first mixed with 2.0 µl of 1:10 diluted from stock solution of RNA spike reagent (One-Color Spike, Agilent) in a 1.5 ml reaction tube including T7 primer at 65° C. for 10 minutes. 8.5 µl from cDNA master reagent kit (Agilent) was then added into this reaction tube and incubated at 40° C. for 2 hours. For cRNA amplification with Cy3 or Cy5 dye, the reaction tube was subsequently mixed with 60 µl of transcription master reagent kit (Agilent) and incubated at 40° C. for at least 4 hours. The final product of the cRNA was then yielded by using a RNA purification kit from QIAGEN. The quality and yield of cRNA were then analyzed using a NANODROP™ ND-1000 UV-VIS Spectrophotometer (version 3.2.1). Only cRNA with a total yield >1.65 µg and specific avidity >9.0 pmol Cy3 per µg cRNA were used in the hybridization step.
Hybridization on Microarrays and Data Extraction Gene expression analysis involved the use of custom-designed 4×44K microarrays (Agilent) containing approximately 41K human oligo probes. Microarrays were hybridized according to the manufacturer's recommendations from One-Color Microarray-Based Gene Expression Analysis (Agilent). A volume of 100 µl of the labeled cRNA sample was loaded onto each 44K array, after which the slides were loaded onto a slide chamber and hybridized for 17 hours using a rotating speed of 10 rpm at 65° C. (Agilent). Following the hybridization and a washing procedure, the slides were immediately scanned using an Agilent G2565AA microarray scanner. The scanning was done immediately after washing in order to minimize noise created by ozone-induced degradation and loss of fluorescent intensity in the probes. The successfully scanned features were extracted into microarray data files using the Agilent Feature Extraction (FE) version 9.5.1 as referenced in their manual Agilent Technologies). Quality Control criteria were established by previously published experiments (Shippy et al., *Nat Biotechnol* 34(9):1123-1131, 2006). Microarrays that met 9/12 quality control criteria were deemed suitable for statistical analysis.
Statistical Analysis of Microarrays Genespring GX 11 (Agilent Technologies) was used to normalize and filter the data used in this study. The gene expression arrays were subjected to quantile normalization without a baseline transformation, an algorithm similar to RMA-5 normalization techniques widely used in Affymetrix microarrays (Quackenbush, *Nat Genet* 32 Suppl: 496-501, 2002; Do and Choi, *Mol Cells* 22(3):254-261, 2006; Zahurak et al., *BMC Bioinformatics* 8:142, 2007).

After normalization, the probes with values below the 20% percentile in more than 80% of the study samples were removed. The following filtered set was compared for genes being differentially expressed 2-fold above or below the median of normal volunteers. An unpaired, asymptotic t-test with Benjamini- and Hochberg's False Discovery Rate (FDR) correction was used to obtain statistically significant genes that had corrected p-values of <0.05, and a fold change of >2 fold with respect to the median values of healthy volunteers.

The gene list was analyzed for additional pathway information using Ingenuity Pathway Analysis software (IPA). IPA's Molecular Network Analysis algorithm was used to generate candidate gene networks as previously described (Calvano et al., Nature 437(7061):1032-1037, 2005). Similarly, biomarker analyses were used for filtering salivary gland specific-genes as well as secreted soluble factors. FDR-corrected p-values were used to generate significancy cutoffs throughout all of the analytical results obtained from IPA.

Construction of cDNA Libraries

Purified RNA from the patients was reverse-transcribed using a SuperScript VILO™ First-Strand cDNA synthesis kit for two-step quantitative RT-PCR (Invitrogen). The cDNA library constructed was used for comparative ΔΔCt quantification studies, where GAPDH was the internal housekeeping gene.

Animals

Female C57Bl/6 mice (N=28), 6-8 weeks old, were obtained from Jackson Laboratory (Bar Harbor, Me.) Animals were housed in a pathogen-free facility and all procedures involving animals were performed in compliance with the NIH Guidelines on Use of Animals in Research.

rAAV5 Vector Administration and Plasma/Saliva Collection

The construction of the AAV5 LacZ, Luciferase, and BMP6 vectors have been described previously. Vectors were delivered into the submandibular glands by retrograde instillation as previously described (Vosters et al., Arthritis Res Ther 11(6):R189, 2009). Briefly, mild anesthesia was induced by ketamine (100 mg/mL, 1 mL/kg body weight (BW); Fort Dodge Animal Health, Fort Dodge, Iowa, USA) and xylazine (20 mg/mL, 0.7 mL/kg body weight; Phoenix Scientific, St. Joseph, Mo., USA) solution given intramuscularly (IM). Ten minutes after IM injection of atropine (0.5 mg/kg BW; Sigma, St. Louis, Mo., USA), female non-obese diabetic (NOD) mice at the age of eight weeks were administered 50 µl vector into both submandibular glands by retrograde ductal instillation ($1 \times 10^{10}$ particles/gland) using a thin cannula (Intermedic PE10, Clay Adams, Parsippany, N.J., USA). The vector dose was chosen based on previously published results, which showed detectable transgene activity above $10^9$ particles/gland (Katano et al., Gene Ther 13(7):594-601, 2006). Saliva collection was done at 4-6 weeks and 22 weeks post cannulation. Mice were anesthetized as described above and saliva secretion was induced by subcutaneous (sc) injection of pilocarpine (0.5 mg/kg BW; Sigma-Aldrich, St. Louis, Mo., USA). Stimulated whole saliva was gravimetrically collected for 20 minutes from the oral cavity with a hematocrit tube (Drummond Scientific Company, Broomall, Pa., USA) placed into a preweighed 0.5 ml microcentrifuge tube, and the volume was determined by weight as previously described (Vosters et al., Arthritis Res Ther 11(6):R189, 2009). The presented saliva data are the result of two independent experiments (N=10 for LacZ and N=18 for BMP6). Blood was collected at the saliva collection time points by retro-orbital plexus bleeding, from which plasma was separated by centrifugation for five minutes in an eppendorf tube centrifuge. Plasma was stored at −80° C. until further analysis.

Plasma Preparation

For plasma preparation, blood was obtained by bleeding animals via the retro-orbital plexus with a hematocrit tube (Drummond Scientific Company, Broomall, Pa., USA) before each treatment. Furthermore, plasma was separated by centrifugation at 2300×g for 5 minutes and stored at −80° C. until further analysis.

Determination of Autoantibodies

Plasma samples were analyzed for autoantibodies against SSA/Ro and SSB/La. The ELISA method used to detect 60-kD MAP-Ro$^{273-289}$ antibodies was described earlier (Scofield et al., J Immunol 156(10):4059-4066, 1996). Briefly, 96-well plates (Nunc, Rochester, N.Y.) were incubated overnight (O/N) with 1 µg MAP-Ro$^{273-289}$ in carbonate buffer (PH 9.6). The next day, wells were blocked O/N with PBS/0.05% bovine serum albumin (BSA). Then the fluid was discarded and incubated with 1:100 dilution of serum in blocking buffer for 2 hours at room temperature (RT). The wells were washed three times with PBS/0.05% Tween and incubated with 1:5000 dilution of goat anti-mouse IgG-HRP (Dako, Carpinteria, Calif.) for 1 hour at RT. Thereafter, the wells were washed 3 times, incubated with 1:1 substrate A and B (R&D systems, Minneapolis, Minn.) for 20 minutes at RT and the reaction was stopped by stop solution (R&D systems, Minneapolis, Minn.). The optical density (OD) was measured at 450 nm using a SPECTRAMAX™ M2 plate reader (Molecular Devices Corporation, Sunnyvale, Calif.). The autoantibody against SSB/La (total Ig) was measured by a commercially available ELISA kit (Alpha Diagnostic International, San Antonio, Tex.) according the manufacturer's protocol.

Histopathology

Submandibular glands (SMG) were removed for histological analysis from mice at the time of sacrifice, and placed O/N in 10% formalin. After fixation, the tissues were dehydrated in an ethanol series and embedded in paraffin according standard techniques. Sections were cut at 5 µm and subsequently stained with hematoxylin and eosin (H&E). Histopathological scoring was performed using the focus score. A focus is an aggregate of 50 or more mononuclear cells per 4 mm$^2$. Foci were counted through the whole section, in a total of three sections (50 µm between sections) per SG using a 40× magnification. The results were calculated and expressed as foci per 4 mm$^2$. The focus scores were assessed blindly by two different examiners and the mean scores were determined Immunofluorescence Formaldehyde-fixed, paraffin-embedded tissue samples were obtained from submandibular salivary gland biopsies, mounted in 8-micron-thick sections onto poly-L-lysine coated glass slides, and adhered in a dry incubation oven at 37° C. O/N. Samples were dewaxed at 40° C. for 40 minutes, then 60° C. for 20 minutes, and rehydrated in 2 changes of xylene, a serial dilution of ethanol, and three changes of ddH$_2$O for 5 minutes each. Using a microwave pressure cooker, heat-induced epitope retrieval was performed in EDTA-T for 10 minutes.

BMP6 expression in human tissue was detected by blocking with 10% donkey serum in 0.5% BSA in PBS diluent for 30 minutes at RT in a humidity chamber. Samples were then incubated at 4° C. O/N with 100 µL of 10 µg/mL AbCam™ Mouse Monoclonal Anti-BMP6 Primary Antibody in 0.5% BSA in PBS. Controls were incubated at 4° C. O/N with 100 µL of 10 µg/mL Jackson ImmunoResearch ChromPure Mouse IgG, Whole Molecule in 0.5% BSA in PBS. Slides were washed in 5 changes of PBS for 5 minutes each, and then incubated with 1:100 dilution of 2 mg/mL Invitrogen AlexaFluor 488 Goat Anti-Mouse IgG Secondary Antibody for 1 hour at RT in the dark, followed by washing in 5 changes of PBS for 5 minutes each, and counterstaining with DAPI mounting medium.

BMP6 expression in mouse tissue was done by direct labeling of the anti-BMP6 antibody using a Zenon labeling kit (Invitrogen CA), and counterstaining with DAPI mounting medium. Controls were incubated with 100 µL of 10 µg/mL Jackson ImmunoResearch ChromPure Mouse IgG, Whole Molecule in PBS similarly conjugated.

Cytokine Assay

Murine IL-2, IL-4, IL-5, IL-6, IL-10, IL-12p70, Il-12p40, IL-17, IL-18, IL23, KC JE, MCP5, MIP1b, MMP9, L-selectin, RANTES, TGF-β1, IFN-γ and TNF-α were measured commercially using SearchLight proteome assay (Pierce Biotechnology, Woburn, Mass., USA). This assay is a multiplexed sandwich ELISA procedure for detecting multiple cytokines in the same minimal sample. The same analytes were determined in plasma samples. Lower detection limits for this assay are: mIL-4: 1.2 pg/ml, mIL-5: 2.3 pg/ml, mIL-6: 5.5 pg/ml, mIL-10: 1.6 pg/ml, mIL-12p70: 0.78 pg/ml, mIL-17: 1.6 pg/ml, MCP-1: 0.78 pg/ml, mTGF-β1: 6.8 pg/ml, mIFN-γ: 7.8 pg/ml, mTNF-α: 3.1 pg/ml. Data from SG homogenates were standardized by protein concentration as above. Duplicates for each sample were tested in three dilutions and the mean values of the duplicates from the optimal dilution were reported. BMP6 expression in serum was measured using a Duo-kit ELISA (R&D systems) and detected on a Meso Scale discovery plate reader (Gaithersburg, Md.)

Epithelial Measurement of SMG and Cell Lines

To measure the electrical potential (EP) across the duct of the SMGs, a procedure was developed to measure the EP by cannulating the duct and inserting the electrode in the cannula. The high impedance electrode was attached to an electrometer (model FD223, World Precision Instrument, Sarasota, Fla.). The electrical potential of the duct was read by placing the ground electronic rode on the adjacent tissues to the opening of the ducts.

Trans epithelial electrical resistance (TER) of an cell types was measured using a using a volt/ohm meter (Millicel; Millipore, Mass., USA) in an electrode chamber (EVOV; WPI, FL, USA). Cells were allowed to establish monolayers on 0.4-Am pore size polycarbonate filters in 6-mm Transwell chambers (Costar, Mass., USA). Only filters of cell monolayers that displayed the required TER were used in the assay (for Caco-2, 200-300 V/cm2; MDCKI, N2000 V/cm2; MDCKII, N200 V/cm).

Hypotonic Stimulated Volume Change

Regulated volume decrease was measured as described previously (Liu et al., *J Biol Chem* 281:15485-15495, 2006). Briefly SMGs from mice were removed at the end of the study and prepared as described (Liu et al., *J Biol Chem* 281:15485-15495, 2006). Cells were then loaded with the fluoroprobe calcein (Molecular Probes, Inc., Eugene, Oreg.) and excited at 490 nm Emitted fluorescence was measured at 510 nm. In situ calibration of the dye was performed. Origin 7.5 (OriginLab, Northampton, Mass.) was used for data analysis and display. Significant difference between individual groups was tested by using analysis of variance.

Results

In order to isolate microarray expression signatures of candidate genes responsible for impaired salivary gland activity in Sjögren's syndrome (SS), the SS patients that met the criteria for primary SS were stratified according to focus score and salivary flow. Patients used in the analysis had histologically normal minor salivary gland architecture on sections but low focus scores (FS≤2), positive autoantibody levels and impaired salivary flow. Most subjects also report ocular symptoms. The age and gender-matched healthy volunteers (HV) were free of lymphocytic foci, autoantibodies, and showed normal salivary flow (Table 1).

TABLE 1

Clinical characteristics of study members selected for analysis

| Patient Classification | Age at Biopsy | Focus Score | Ocular Symptoms | Flow | Auto-antibodies | SG ID |
|---|---|---|---|---|---|---|
| Healthy Volunteer | 44 | 0 | N | Normal | Negative | 102 |
| Healthy Volunteer | 30 | 0 | N | Normal | Negative | 122 |
| Healthy Volunteer | 37 | 0 | N | Normal | Negative | 85 |
| Healthy Volunteer | 53 | 0 | N | Low | Negative | 86 |
| Healthy Volunteer | 34 | 0 | Y | Low | Negative | 88 |
| Healthy Volunteer | 54 | 0 | N | Normal | Negative | 97 |
| Primary Sjogren's | 58 | 2 | Y | Low | Positive | 101 |
| Primary Sjogren's | 42 | 1 | Y | Low | Positive | 105 |
| Primary Sjogren's | 31 | 2 | N | Low | Positive | 106 |
| Primary Sjogren's | 62 | 2 | Y | Low | Positive | 37 |
| Primary Sjogren's | 60 | 2 | Y | Low | Positive | 94 |

The focal score indicated was quantified by examining the lymphocytic involvement in the labial salivary gland used for the study. Ocular involvement was determined to be present using information from the Schirmer-1 test as well as the Rose-Bengal dye score obtained during examination. Salivary flow rate was determined using stimulated as well as unstimulated salivary flow measurements. Serology denotes detection of anti-nuclear antibodies routinely screened for, as well as SSA and SSB.

Prior to analysis, signal intensity was adjusted between samples using a quantile normalization protocol. Genes that were differentially expressed between SS patients and HV were identified based on statistical significance (P<0.05, after adjustment with the Benjamin-Hochberg Multiple Testing Correction for False Discovery Rate method). The resultant gene signature efficiently clustered SS patients and HVs into two separate groups using unsupervised clustering techniques. The top 75 differentially expressed genes are shown in FIG. 1, several of which have been previously reported to be involved in disease progression of SS such as CCR5, IRF5, GZMK and MMP9 (Petrek et al., *Clin Exp Rheumatol* 20(5):701-703, 2002; Miceli-Richard et al., *Arthritis* Rheum 56(12):3989-3994, 2007, Hjelmervik et al., *Arthritis Rheum* 52(5):1534-1544, 2005, Hulkkonen et al., *Rheumatology* 43(12):1476-1479, 2004).

Figure 1B:
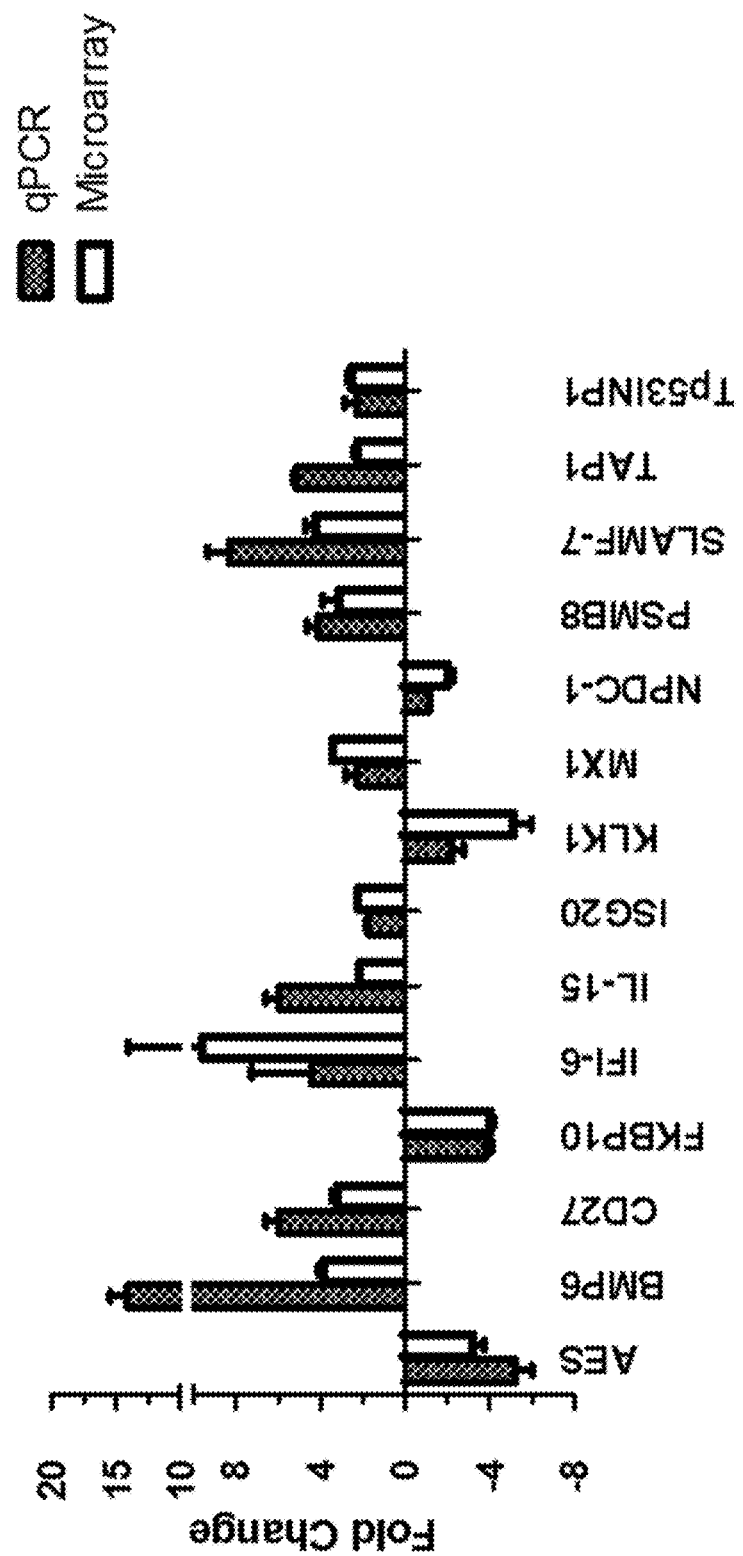

In order to validate the normalization and gene filtering process, quantitative two-step RT-PCR was performed in a subset of genes representative of the microarray signature. The validation was carried using template cDNA prepared from the biopsies of the SS patients in the microarray study (FIG. 1B). The qPCR results showed an agreement with the microarray gene expression in genes that were up-regulated as well as in genes down-regulated in SS patients, with respect to the HVs.

After validation of the microarray signature was complete, Ingenuity Pathway Analysis was used to locate gene networks based on known interactions (Table 2). The highest number of associations were found in networks relating to type 1 interferon responses (network 1 on Table 2). Top functions associated with the networks were Immunological Disease, Cellular Growth, Cellular Proliferation and Cellular Movement.

TABLE 2

Top Network Associations Identified in Microarray Study

| ID | Genes in Network | Top Functions Associated with Genes in Network |
|---|---|---|
| 1 | Ap1, ↑APOL3, ↑BIRC3, ↑CARD8, ↑CCL2, ↑CCL4, ↑CCR5, ↑CD3G, ↑CFLAR, ↑HLA-B, ↑ICAM2, ↑IFI27, ↑IFIT1, IFN Beta, ↑IL15, IL12 (complex), ↑IL23A, Interferon alpha, ↑ISG15, ↑ISG20, ↑ITGB2, ↑MX1, ↑NCF2, NFkB (complex), P38 MAPK, ↑PSMB8, ↑PSMB9, ↑RAC2, ↑SERPINB9, ↑SOD2, ↓SRC, ↑STAT1, ↑TBX21, TCR, ↑USP18 | Immunological Disease, Infectious Disease, Inflammatory Response |
| 2 | ↓ALOX15B, AR, ↑BST2, ↑CCL2, CCL3, ↑CCL4, CCL5, ↑CCR1, ↑CD47, ↑CD58, CD86, ↑CD163, CD40LG, ↑CTSS, CXCL10, EGR1, ↑GADD45A, ↑HLA-F, HMGB1 (includes EG: 3146), IL27, IL17A (includes EG: 3605), IRF1, ↑LAMP3, ↑MMP9, NAMPT, ↓NPM3, PLAUR, ↑PLSCR1, RNASE1, RNASE2, ↑SMPD3, ↑STAT1, ↑TAP1, ↓TEAD3, TNF | Immunological Disease, Cellular Movement, Hematological System Development and Function |
| 3 | ↓ADAM15, ATF2, ↑ATF3, C3, C5, CASP3, ↑CCL2, CCL20, ↑CD48, ↑CD52, CXCL1, ↑CXCR4, EGR1, ↑F13A1, ↓FTH1, IL3, IL13, IL27, IL1B, JUN, ↑LCK, ↑MGAT3, MIF, ↑MMP9, PARP1, PRKCD, ↓RORC, SERPINB5, SERPINE1, ↑SLA, ↑SLC7A7, ↑SOD2, ↑SRGN, ↑STK4, ↑TP53INP1 | Cellular Growth and Proliferation, Cell Death, Tissue Morphology |
| 4 | ACTB, Ap1 gamma, ↓APP, B2M, C1q, CCL2, CCL3, CCL5, CCL20, CD38, CD44, CD40LG, ↓CLN3, CMA1, DDX58, ↓EMD, Fibrinogen, HLA-A, HNRNPA1, IFITM1, IFNG, IgG, IL16, IL21, IRF1, IRF2, KITLG, LCK, ↓MMP14, PECAM1, PIM1, SUMO2 (includes EG: 6613), ↓TRIM29, TXN, ↓U2AF1 | Cell Death, Cellular Movement, Hematological System Development and Function |
| 5 | ACTB, ↑ADCY7, ↓ARID1B, ↑CFLAR, ↑CIITA, CTNND1, CXCL10, ↑CXCR4, FKBP5, FSH, HSD11B1, IRF1, Lh, MAP2K1, MAP3K5 (includes EG: 4217), MIR122, ↑MMP9, ↑MSMB, NFKB2, PTPASE, ↑PTPRC, ↑RAB31, ↑RAB11FIP1, ↑RGS16, ↓RPRM, SGK1, SIN3A, SMARCA4, ↑STAT1, TFPI2, THBS1, TLN1, ↑TRIB1, ↑VAV1, WT1 | Cellular Growth and Proliferation, Hematological System Development and Function, Tissue Morphology |
| 6 | ↑ADRB2, ↑ALOX5, ↑BMP6, BMP7, CASP1, CCNE1, ↑CD2, CD59, COL1A2, CRP, ↑CSTA, ERK, ↑FLI1, FOXO1, ID1, IL3, IL4, IL6, IL22, IL17A (includes EG: 3605), IL17F, ↑IL6R, ↓LTBP2, ↑MMP9, ↑NR3C1, ↑PLCG2, PRKCA, ↓PTMS, SERPINE1, ↑SLAMF7, ↑SPAG4, STAT5a/b, TGFB1, THPO, TIMP1 | Dermatological Diseases and Conditions, Cell Death, Cellular Growth and Proliferation |
| 7 | APC, ASCL2, ↑BCL2, ↑CDKN1B, COL18A1, ↑CRIP1, ↓CST4, CTNNB1, ↑CTSD, ↑E2F3, ESR1, ↑F2R, ↑HCLS1, ↓HNRNPM, ↓HSD11B2, ↑HSPA13, ID1, IGF1, IGF1R, IGFBP5, ↑IRS2, LYN, MLL2, MT1G, NCOR1, ↑NEU2, ↑NRP1, PDGFRB, RBI, SP3, TCF7L2 (includes EG: 6934), ↓TFAP2A, TNPO1, ↑TRD@, XBP1 | Cellular Growth and Proliferation, Cancer, Cellular Development |
| 8 | ↑APBBUP, BAX, ↑BCL2, BCL2L1, BID, CASP2, CASP7, CASP8, ↑CASP10, ↑CD8A, CYCS (includes EG: 54205), FYB, ↑GBP5, ↑GZMB, IFNB1, IFNG, IL1RN, ↑IRF5, IRF7, ↑LILRB3 (includes EG: 11025), MCL1, MHC Class I (complex), ↑NFIL3, NFkB (complex), NFKBIA, P38 MAPK, PARP1, SKAP1, TNF, TNFSF10, ↓TP53AIP1 | Cell Morphology, Cell Death, DNA Replication, Recombination, and Repair |

Analysis of differentially expressed genes using IPA revealed a set of gene networks based on known interactions. Genes differentially expressed in the current study are shown in bold, preceded by an arrow that signifies the expression level in patients with respect to healthy volunteers.

In order to focus on salivary gland-specific genes, a biomarker filter was used to narrow down the results to genes that have previously shown expression in normal salivary gland epithelia. Of this list of proteins, bone morphogenetic protein 6 (BMP6) was highly upregulated (Table 3). This was also confirmed by hybridization of additional microarrays with RNA isolated from additional samples of healthy volunteers and Sjögren's patients with low gland activity and low focus score.

TABLE 3

Salivary Gland Specific-Genes

| Symbol | Entrez Gene Name | p-value | Fold Change | Salivary Gland | Secreted |
|---|---|---|---|---|---|
| BMP6 | Bone morphogenetic protein 6 | 0.004 | 4.465 | X | X |
| ARSJ | Arylsulfatase family, member J | 0.032 | 2.103 | X | X |
| ND5 | NADH dehydrogenase, subunit 5 (complex I) | 0.005 | −2.007 | X | |
| SLC22A17 | Solute carrier family 22, member 17 | 0.001 | −2.008 | X | |
| STAC2 | SH3 and cysteine rich domain 2 | 0.02 | −2.134 | X | |
| CRISP3 | Cysteine-rich secretory protein 3 | 0.039 | −2.179 | X | X |
| AQP5 | Aquaporin 5 | 0.043 | −2.19 | X | |
| PITX1 | Paired-liked homeodomain 1 | 0.006 | −2.215 | X | |
| TEAD3 | TEA domain family member 3 | 0.023 | −2.464 | X | |
| CLDN3 | Claudin 3 | 0.01 | −2.605 | X | |

Bone morphogenetic protein-6 (BMP6) is a member of the transforming growth factor-β (TGF-β) signaling molecule family. It was originally found to signal mesenchymal cell lines to mature and differentiate into osteoblast and chondroblast cell lineages and it induces cartilage and bone formation in vivo (Gitelman et al., *J Cell Biol* 126(6):1595-1609, 1994; Gitelman et al., *Cell Growth Differ* 6(7):827-836, 1995). Within epidermal tissue, BMP6 has been found in the suprabasal layer (Lyons et al., *Genes Dev* 3(11): 1657-1668, 1989; Wall et al., *J Cell Biol* 120: 493-502, 1993). It has been shown to induce stratification and keratinization (Drozdoff et al., *Proc Natl Acad Sci USA*, 91: 5528-5532, 1994; Blessing et al., *J Cell Biol* 135(1):227-239, 1996). Post-mitotic keratinocytes that start going through differentiation begin to express BMP6 (Drozdoff et al., *Proc Natl Acad Sci USA*, 91: 5528-5532, 1994). BMP6 is critically important for the development of certain tissues; however, in adults, changes in the level of BMP6 have been correlated to different diseases and autoimmune disorders. Recently, BMP6 was identified as a major regulator of hepcidin expression and thereby of iron homeostasis (Andriopoulos et al., *Nat Genet* 41(4):482-487, 2009). BMP6 null mice developed massive iron overload in the liver, resembling human juvenile hemochromatosis. In keratinocytes, an increase in BMP6 expression may produce consequences similar to psoriasis (Blessing et al., *J Cell Biol* 135(1):227-239, 1996). Different magnitudes of expression of the BMP6 gene have different consequences.

High levels of expression based on staining for BMP6 are associated with strong inhibition of cell proliferation in the epidermis. However, a weaker over-expression of the gene results in hyperproliferation of the keratinocytes and parakeratosis. Lymphocytic infiltration was also seen in samples of weaker-overexpression (Blessing et al., *J Cell Biol* 135 (1):227-239, 1996). Expression of BMP6 is also reported in the salivary gland. In adult submandibular glands and parotid glands, BMP6 mRNA is normally expressed at low levels within the acinar cells, but is not expressed within the ductal or stromal cells. In addition, elevated expression of BMP6 is reported in patients with acinic cell carcinoma (Heikinheimo et al., *Cancer Res* 59: 5815-5821, 1999).

To determine if Sjögren's patients express BMP6 in their serum, an ELISA was developed with sensitivity to 50 pg/ml BMP6. Testing of serum samples from a randomly selected population of SS patients or HV did not detect BMP6 levels above the 50 ng/ml level of sensitivity of the ELISA.

Figure 2B:
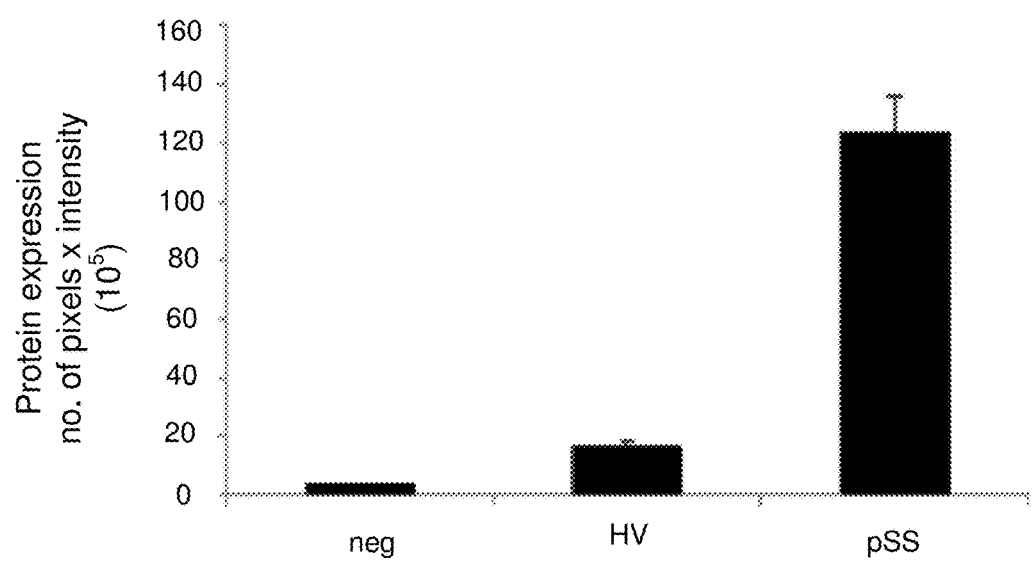

To confirm that the elevated BMP6 RNA correlated with an increase in protein, immunofluorescence detection was used to test for expression of BMP6 in the salivary glands of SS patients or HVs (FIG. 2). The results showed a clear distinction in the expression in both overall expression and tissue distribution of BMP6 protein. In agreement with previous studies, HVs express low levels of BMP6 in acinar cells. In contrast, SS patients expressed significantly elevated levels in multiple cell types with in the gland (FIG. 2A). A digital western blot analysis was used to quantify this difference in fluorescent intensity across a 3-dimensional stack of images, again showing a statistically significant difference between the diseased gland and the healthy gland (FIG. 2B).

The autoimmune prone non-obese diabetic (NOD) mouse spontaneously develops a pSS like phenotype and is often used as a model for studying Sjögren's syndrome (Chiorini et al., *J Autoimmun* 33:190-196, 2009). Female NOD mice will develop gene changes in adhesion molecule, macrophage, and dendritic cells at a young age followed by focal infiltrates in their salivary glands as early as 8 weeks of age. In addition to elevated proinflammatory cytokines and autoantibody production, NOD mice show a decline in salivary and lacrimal gland function by 20 weeks (Humphreys-Beher and Peck, *Arch Oral Biol* 44(Suppl):S21-25, 1999; Roescher et al., *Oral Dis* 18:96-106). Immunofluorescent detection of BMP6 expression indicated elevated levels of BMP6 staining in salivary glands by 8 weeks compared with balb/c mice. By 20 weeks BMP6 expression had continued to increase, suggesting a correlation between BMP6 expression and a Sjögren's syndrome like phenotype in mice as well as humans.

Figure 3A:
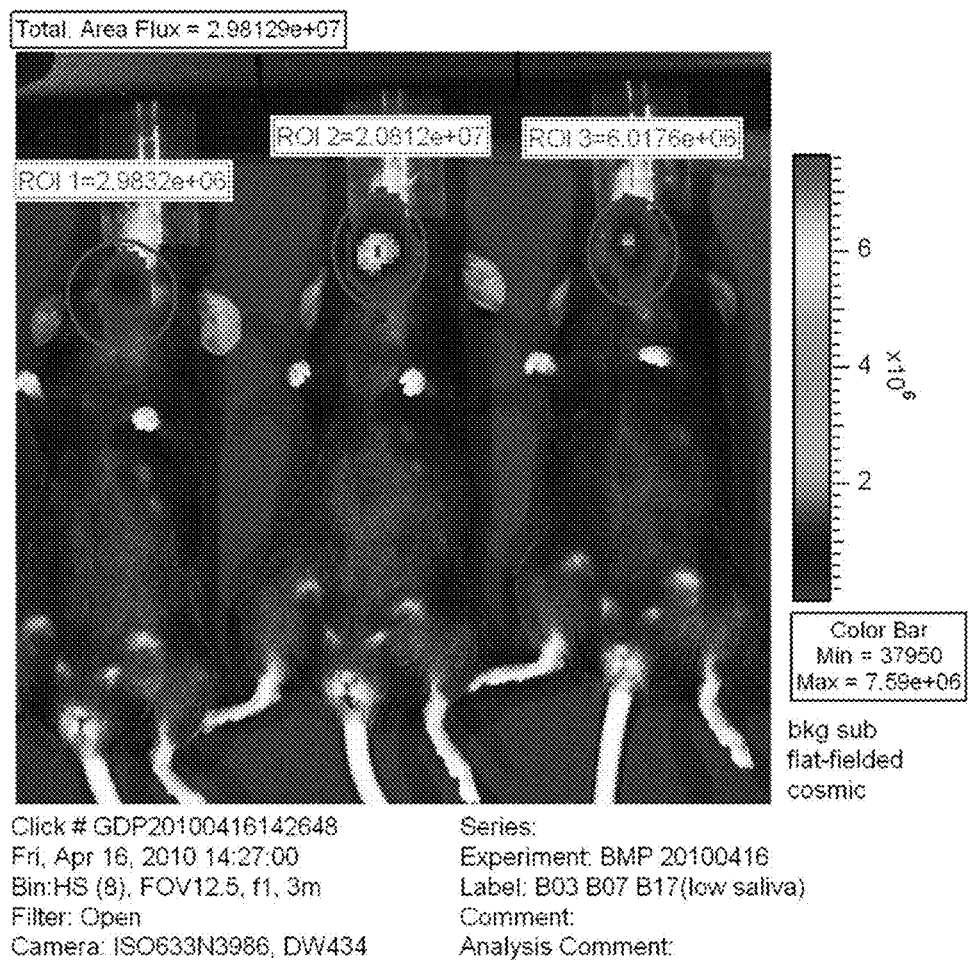
FIGS. 3A-3B: Cannulation and expression of BMP6 in the salivary glands of mice.
Figure 3B:
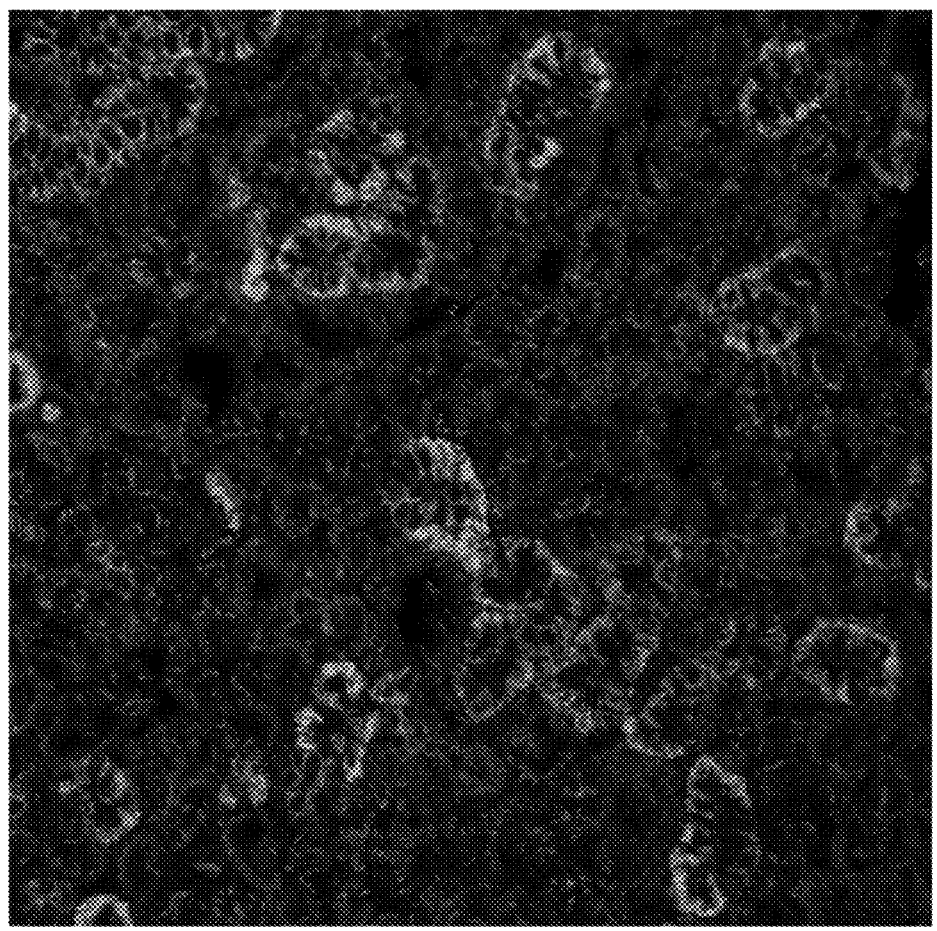

In order to better understand the role of elevated BMP6 expression in the pathology and loss of salivary gland function associated with SS, adeno-associated virus (AAV) vectors were used to stably express BMP6 specifically in the salivary glands of C57Bl/6 female mice. AAV vectors were chosen because of their ability to direct long term expression in the salivary glands of mice with minimal host response to the vector (Katano et al., *Gene Ther* 13(7):594-601, 2006). Mouse salivary glands were infused with $10^{11}$ particles of either an AAV5 vector encoding BMP6 or as a control GFP via retrograde cannulation. To aid in the confirmation of transduction, the AAV5BMP6 treated mice were co-transduced with $10^{10}$ particles of AAV5 encoding luciferase to allow visualization of transduction by xenogeny imaging. Previous work has established that over 90% of the infused vector remains in the gland and AAV5 is able to transduce 50% of the striated ductal cells within the gland. After 4-6 weeks, expression was measured using a Xenogen imaging system, which confirmed the successful infusion of the AAV5 vectors and BMP6 expression was confirmed by RT-PCR when the mice were euthanized at 20 weeks (FIG. 3A). In agreement with previous studies, expression was detected exclusively in the submandibular glands of the transduced mice following cannulation of Wharton's duct. BMP6 expression was confirmed by immunofluorescent stain for BMP6 (FIG. 3B).

Figure 4A:
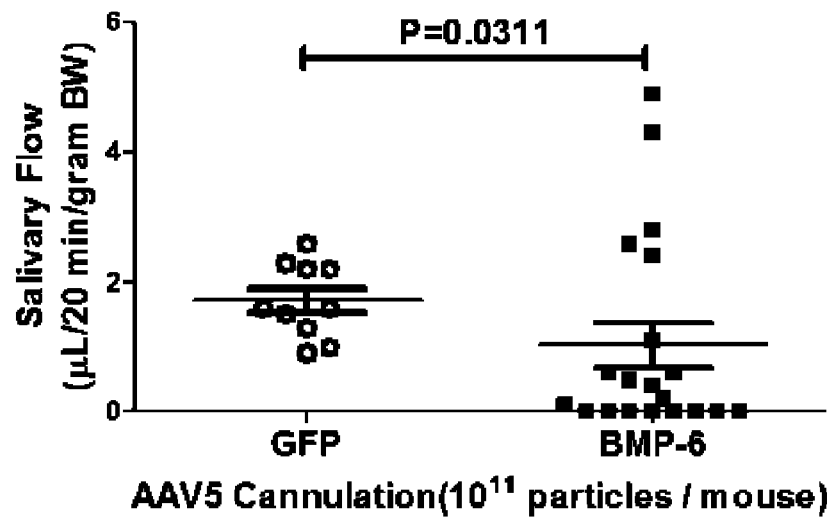
FIGS. 4A-4C: Salivary gland and lacrimal gland activity in AAV5BMP6 and AAV5GFP control treated mice. Saliva and tear flow were measured as described in Example 1. The data shown represent the mean±SEM flow per group (N=18 in AAV5BMP6 and N=10 in AAV5GFP group). Unpaired student t-test was used in this analysis.
Figure 4B:
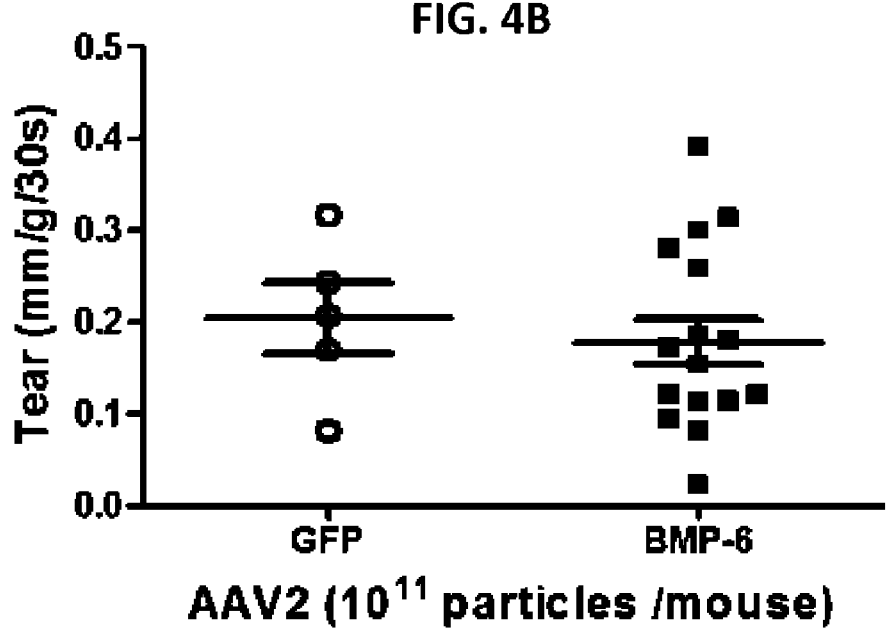

With over-expression of BMP6 in the local milieu established, salivary gland function was tested 4-6 weeks post-cannulation. Pilocarpine stimulated salivary gland flow was measure and demonstrated a statistically significant decrease in flow rates in the BMP6-treated group compared with control GFP vector-treated mice (FIG. 4). In contrast, no change in activity was observed in the lacrimal glands likely as a result of the localized expression of the BMP6.

Figure 14:
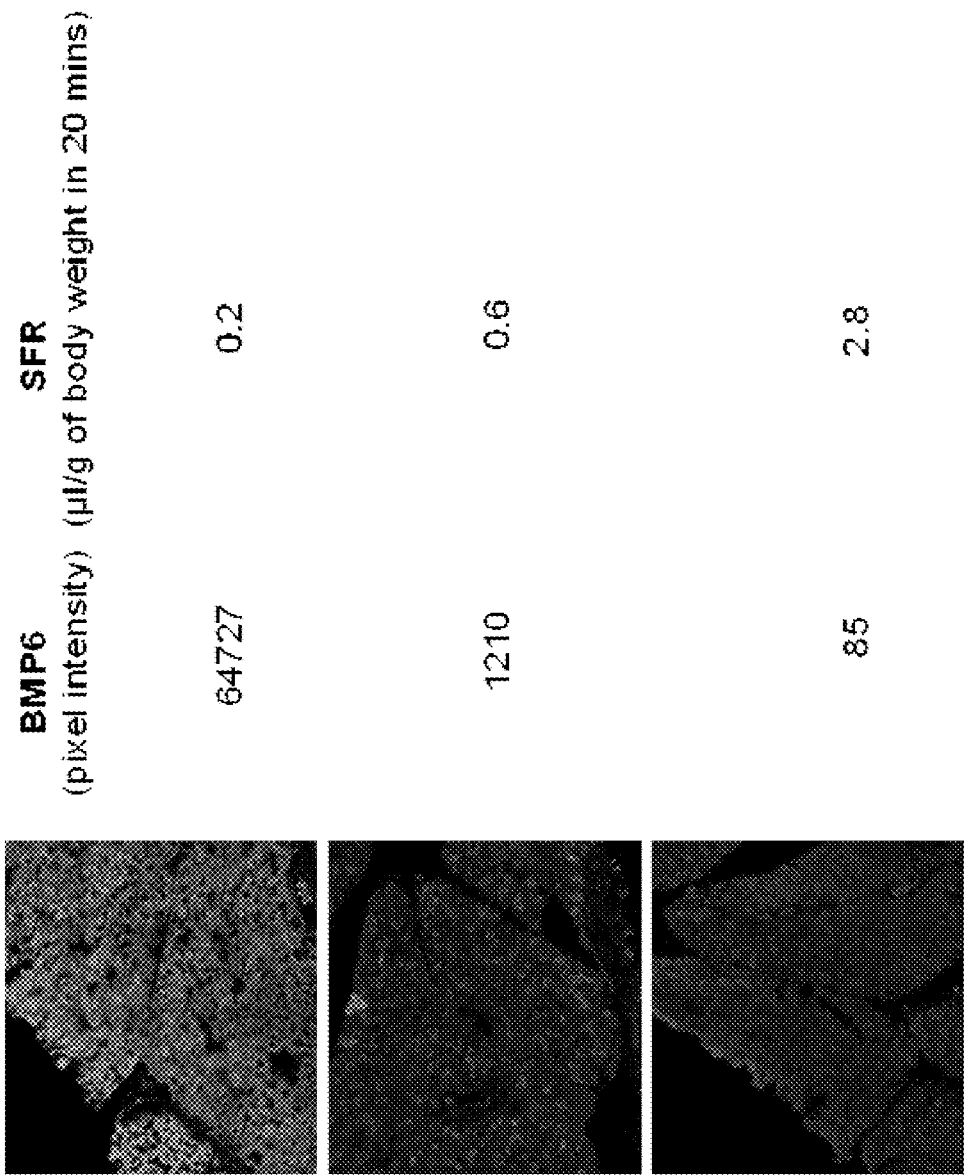
FIG. 14: BMP6 expression and flow rates. Immunofluorescence staining for BMP6 in cannulated mice with different pilocarpine stimulated flow rates.

Immunofluorescence measurements were used to examine the level of BMP6 expression in the subset of BMP6 treated mice with normal levels of saliva flow and the BMP6 fluorescent intensity staining was 10-100 times lower in these mice compared with mice with low salivary flow activity (FIG. 14). In agreement with the loss of saliva flow, ion composition also changed as a result of BMP6 expression. BMP6 treated mice had a statistically significant decrease in sodium and in their saliva (72.0 vs. 56.1, P=0.0058). Potassium was also decreased but was not statistically significant (31.41 vs. 26.1, P=0.0822).

Figure 4C:
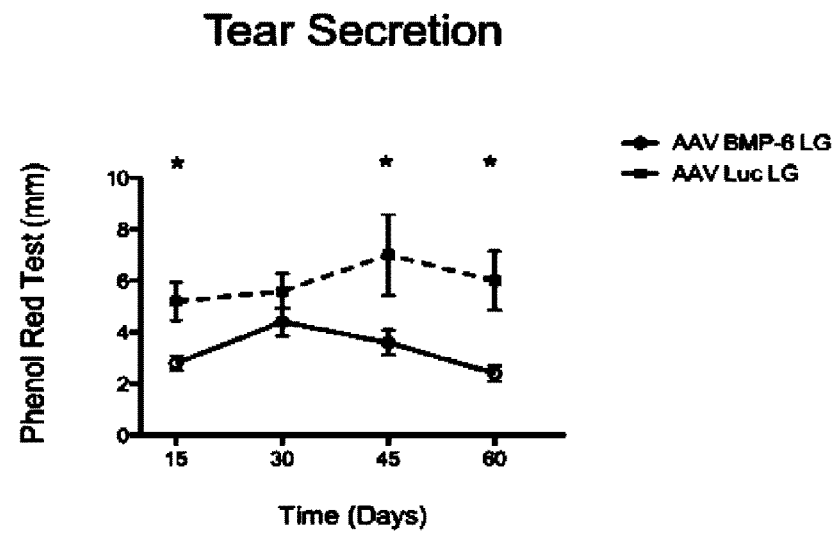

The effect of BMP is reported to be very cell specific and localized in its effect. To confirm that lacrimal glands could be responsive to BMP6, the lacrimal glands of BALB/c mice were transduced with either AAV5BMP6 or AAV5GFP by direct injection, and lacrimal gland activity was followed over time (FIG. 4C). A statistically significant decrease in lacrimal gland activity was detected as early as 15 days post vector delivery and persisted for the duration of the study (60 days). Thus, in agreement with previous studies, the effect of BMP6 is localized and like the salivary gland, secretory activity can be inhibited by BMP6 expression.

Figure 5A:
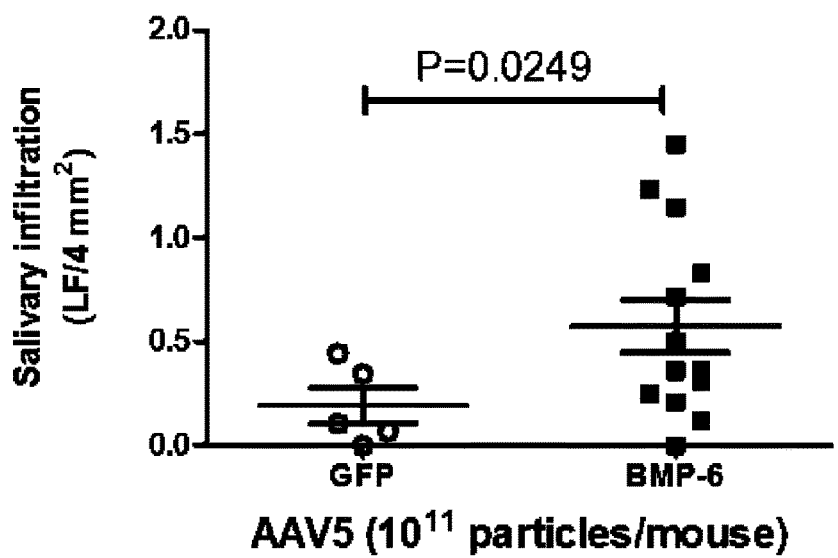
FIGS. 5A-5D: Immunological changes in AAV5BMP6 and AAV5GFP control treated mice. Graphs show representative focus score for salivary gland (FIG. 5A) and lacrimal gland (FIG. 5B) tissue. No statistically significant changes were detected. Serum samples were analyzed for anti-Ro (SSA) (FIG. 5C) and anti-La (SSB) (FIG. 5D) antibody expression in serum from AAV5GFP and AAV5BMP6 treated mice by ELISA. The data shown represent the mean±SEM in OD or U/ml from duplicate tests of pooled samples from each group. Unpaired student's t-test was used for statistical analysis. No statistically significant difference was detected.
Figure 5B:
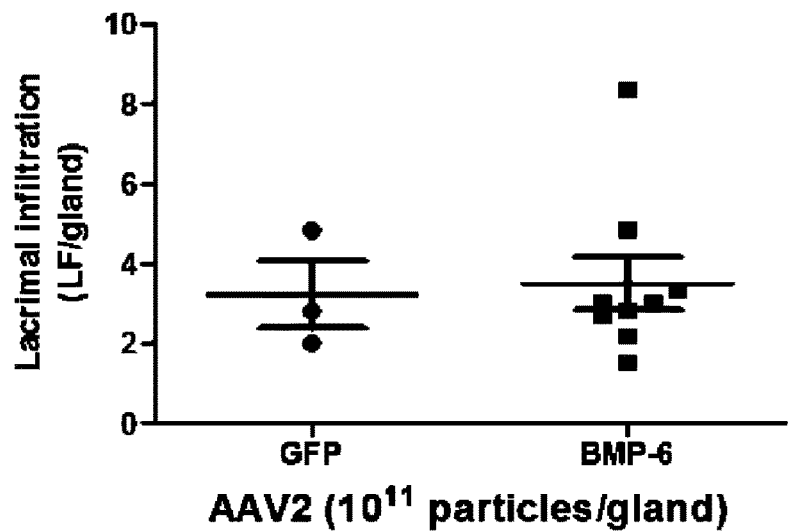
Figure 5C:
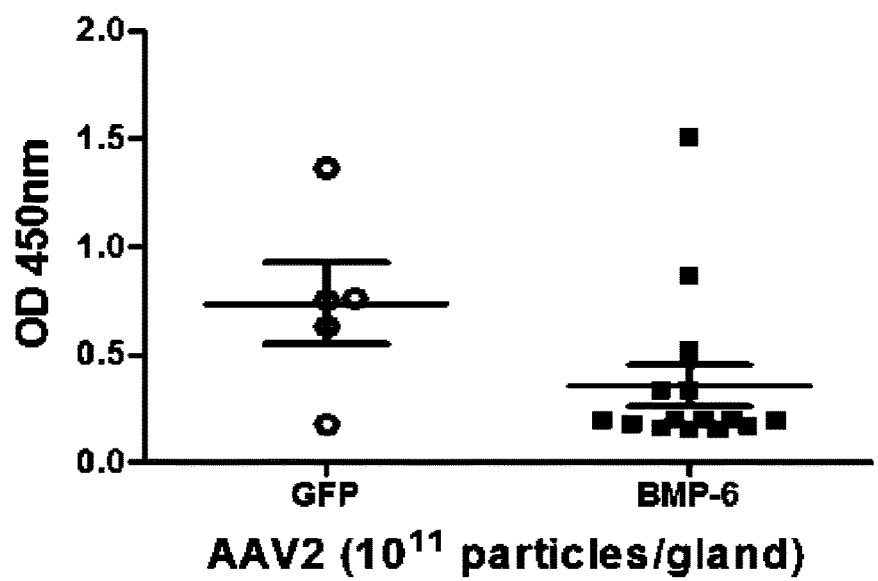
Figure 5D:
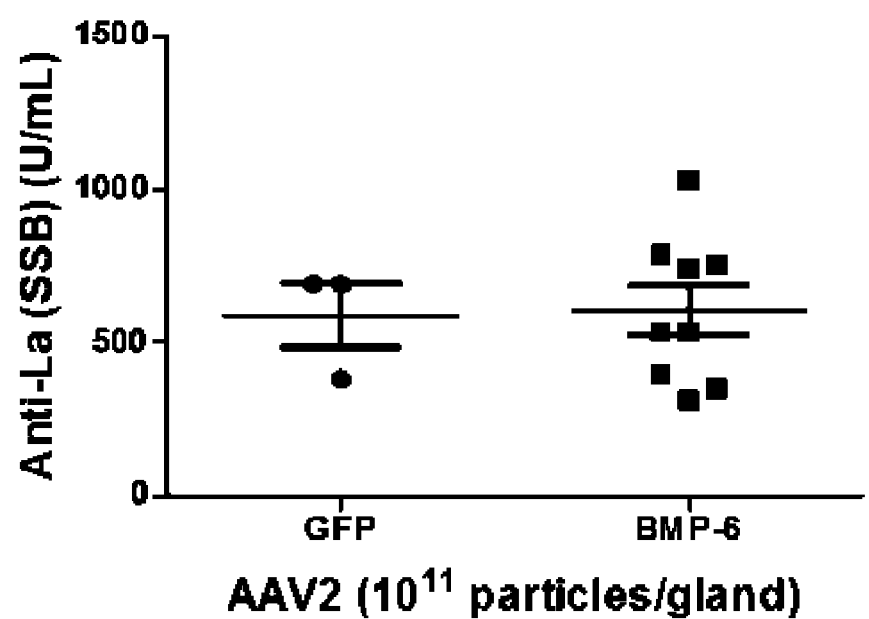

A hallmark of pSS is lymphocytic infiltration in the endocrine glands, especially salivary and lacrimal glands. To determine the effect of elevated BMP6 on the local immune environment of the salivary gland, histopathological scoring for lymphocytic infiltrates was performed on both salivary and lacrimal glands 20 weeks post cannulation. In addition to the decrease in gland function, a statistically significant increase in focus score was observed in the salivary glands (>2 fold, FIG. 5A), but not the lacrimal glands, in agreement with the localized effect of the BMP6 expression on secretory function (FIG. 5B). No difference in the focus score was observed in the lacrimal gland treated mice. Furthermore, no changes in circulating autoantibodies to anti-Ro/SSA or anti-La/SSB were detected in the animals expressing BMP6 in the salivary glands compared with control mice (FIGS. 5C and 5D). Cytokine analysis of the serum and salivary glands by multiplex bead assay indicated only minor changes in cytokine levels between BMP6 treated and GFP control mice (FIG. 9).

Figure 6:
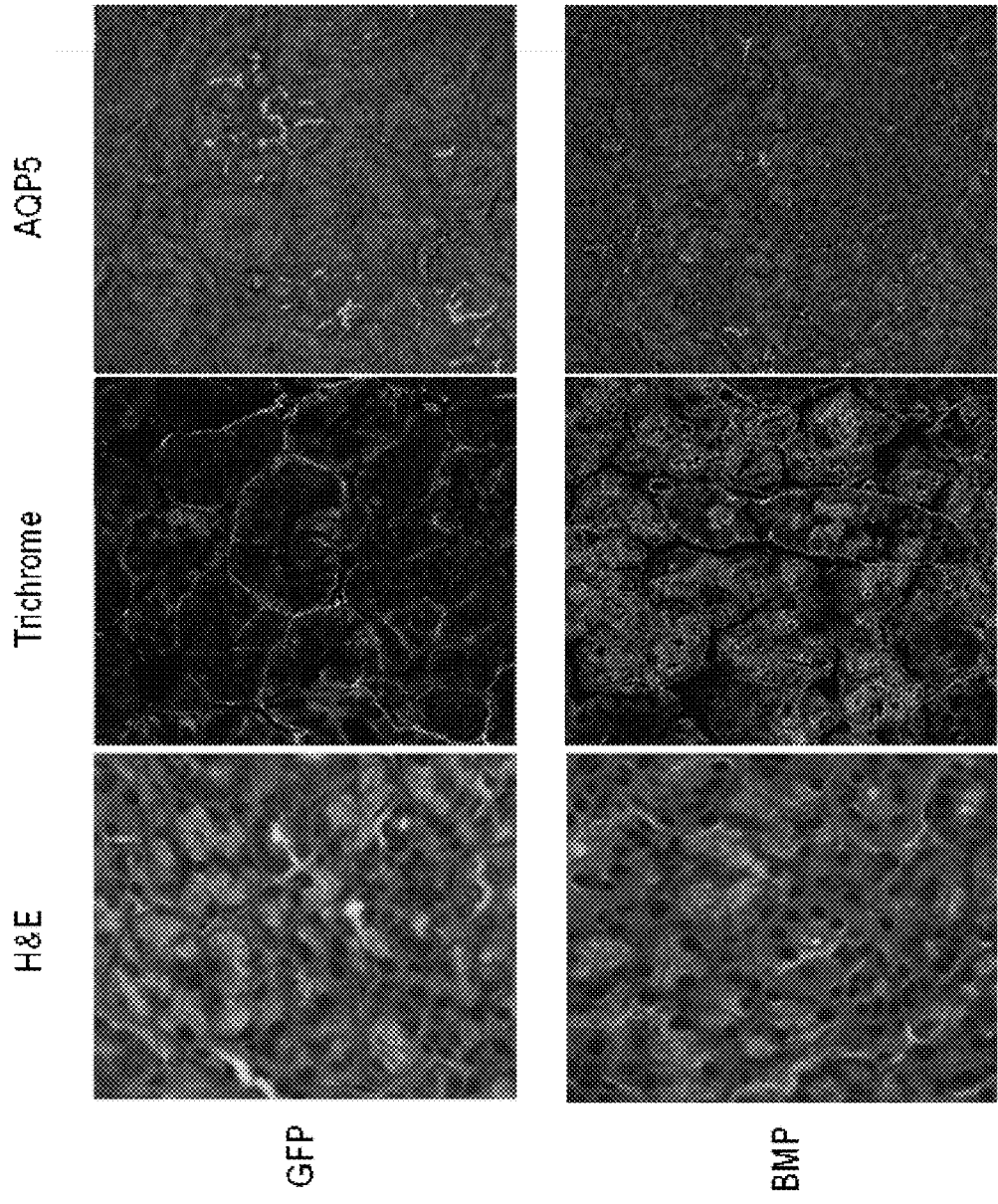
FIG. 6: Morphologic changes in the gland. Changes in morphology, protein expression or distribution were assessed by H&E (left panels) trichrome (middle panels) or immunofluorescence for AQP5 (right panels). Panels show representative images (N=4). Morphology of acini in AQP5 images were enhanced by overlay on DIC images.

To better understand the mechanism associated with the loss of salivary gland function induced by increased BMP6 expression, the overall structure of the salivary glands as well as the distribution of specific salivary gland proteins were compared (FIG. 6). Although no gross change in morphology was observed by ME staining (FIG. 6, left panels), nice that received BMP6 appeared to have a thickening of the extracellular matrix surrounding the acini and enlarged acini compared with the GET control vector treated mice. This change in extracellular matrix was confirmed by staining with trichrome and fluorescent imaging (FIG. 6, middle panels). In addition to the enhanced extracellular matrix in the BMP6 treated mice, staining for the acinar specific protein AQP5 appeared to be less well defined on the apical surfaces in the BMP6 treated mice compared with controls, suggesting alterations in protein distribution on the cell surface or acinar organization (FIG. 6, right panels).

Figure 7B:
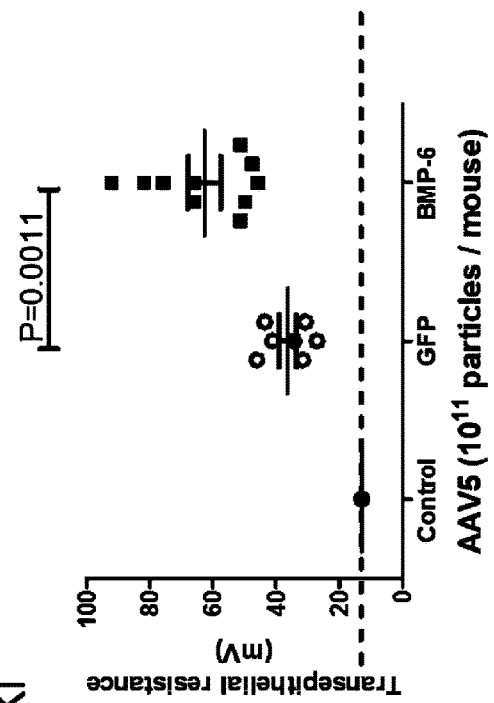
FIGS. 7A-7B: BMP6 affects the TEER and electrical potential in cultured cells and salivary glands. In order to assess the change in TEER as a result of BMP6, trans-epithelial resistance and electrical potential were measured in cultured cells (FIG. 7A) and intact salivary glands (FIG. 7B). For the measurements in intact salivary glands, mice were transduced with $10^{11}$ particles of AAV5 expressing either GFP or BMP6. The electrical potential of pierced ducts was used as a control for epithelial integrity (N=2, 27.50±2.50 mV). Overexpression of BMP6 resulted in an increase in electrical potential compared with GFP control mice.
Figure 7A:
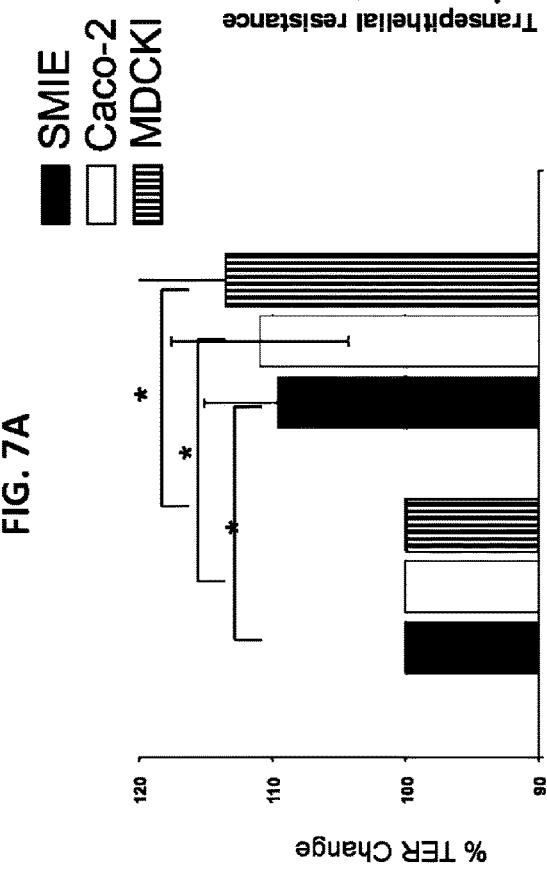

Tight junction structures are important in the correct functioning of the salivary glands. Although BMP6 has been associated with cell differentiation, this finding suggests a role for BMP6 in determining the epithelial integrity of the salivary gland. To determine if BMP6 expression could alter epithelial integrity, monolayers of three well differentiated epithelia (SMEI, Cacao-2, and MDCK1 cells) grown in the presence of 6 ng/ml BMP6 in transwells were tested for changes in trans epithelial resistance (JEER) compared with cells grown without BMP6 (FIG. 7A). In all three cell types, BMP6 treatment resulted in a statistically significant increase in TEER compared with control cells. BMP6 expression also changed the electrical potential of the glands as well (FIG. 7A). Measurement of the electrical potential across the epithelia of the gland also increased in the BMP6-treated mice compare with the GFP controls (FIG. 7B). Placement of the lead within the lumen of the duct via a cannula and the ground on the exterior of the duct recorded an increase in electrical potential compared with GFP control mice. As a control for epithelial integrity, insertion of the cannula through the epithelial layer resulted in a loss in electrical potential. Taken together, these results suggest that BMP6 can directly affect salivary gland function by changing the distribution of tight junction proteins within the gland and the overall electrical potential.

Salivary gland cells are reported to undergo regulated volume decrease (RVD) in response to cell swelling which critically impacts salivary gland fluid secretion induced by neurotransmitter stimulation of the gland (Liu et al., *J Biol Chem* 283(6):3688, 2006). Several monovalent cation and anion channels such as maxiK and NKCC1 as well as intracellular $Ca^{2+}$ transporters changes contribute to cell volume regulation. A critical protein in this process is AQP5, which showed an altered distribution following BMP6 treatment. To determine if salivary acinar cells had altered RVD following BMP6 treatment, cells were isolated from BMP6 treated and control mice and RVD was triggered by treatment with hypotonic solution to induce swelling (FIG. SA), Following the initial swelling, cells from GFP treated mice slowly recovered their cell volume over several minutes. In contrast, cells from BMP6 treated mice did not recover suggesting a change in water movement.

Figure 8A:
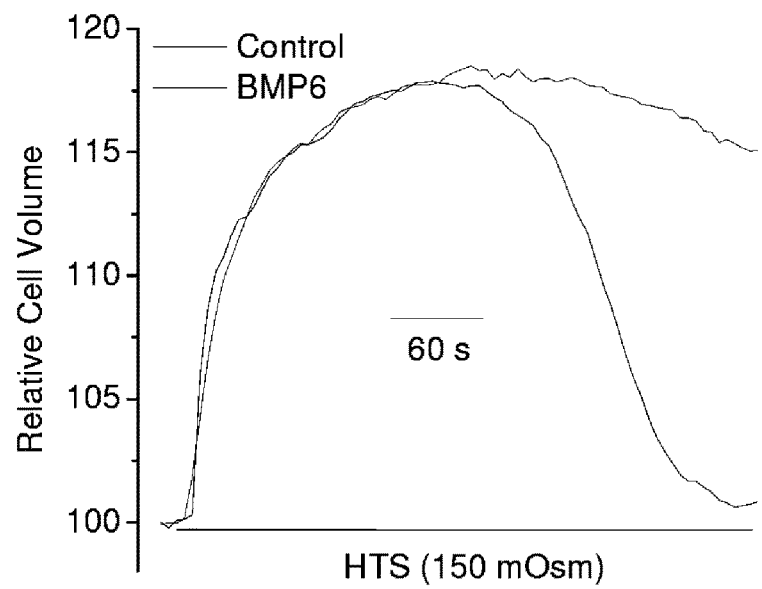
FIGS. 8A-8B: Regulated volume decrease (RVD). Salivary glands from BMP6 treated or WT control were collected and cells were isolated at the end of the study. RVD was induced by cell swelling with hypotonic solution (HTS). A significant decrease in % of RVD recovery cells was observed in the isolated primary acinar cells (FIG. 8A) compared with acinar cells from GFP treated mice. RVD was also measured in HSG cells treated with BMP6 (FIG. 8B). The data shown represents the mean±SEM in each group. Unpaired student-t test was used in this analysis. **, $P<0.001$.
Figure 8B:
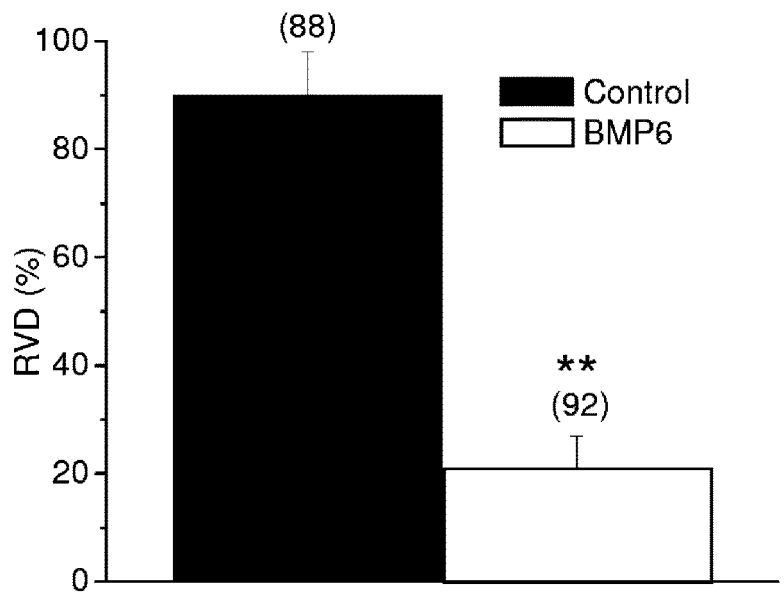

Although no increase in a number of immunological factors was detected, it is not possible to rule out the possibility that BMP6 expression is a trigger for expression of another soluble factor and is not directly causing the loss of RVD in isolated salivary gland cells from the treated mice. To test for a direct effect of BMP6 on RVD, HSG cells (a human salivary gland cell line) were treated with 6 ng/ml of BMP6 for 4 days and then assayed for a loss in RVD activity (FIG. 8B). Just as with the primary acinar cells isolated from the AAV5 BMP6 transduced mice, a loss of volume decrease was detected, suggesting the loss of RVD was directly related to the expression of BMP6.

The above data suggest that the over expression of BMP6 observed in the microarray and histology data from SS patients induces the loss of salivary gland activity in mice, indicating this is a critical trigger in the disease. Furthermore, the present data indicates that it is possible to separate the immune infiltrations and proinflammatory cytokines associated with Sjögren's syndrome from the loss of salivary gland function. To date little is known about the role of BMPs in SS and the present work represents the first association.

Example 2

Measurement Circuit for Diagnosis of Sjögren's Syndrome

This example describes a trans epithelial electronic resistance (TEER) assay in SMGs of AAV2-Cre vector treated St14$^{LoxP/LoxP}$ mice (List et al., *Am J Pathol* 175(4):1453-1463, 2009). The St14 gene encodes matriptase, which is essential for the maintenance of epithelial integrity, such as in the salivary gland. Upon expression of Cre recombinase in St14$^{LoxP/LoxP}$ mice, St14 is deleted.

Figure 10:
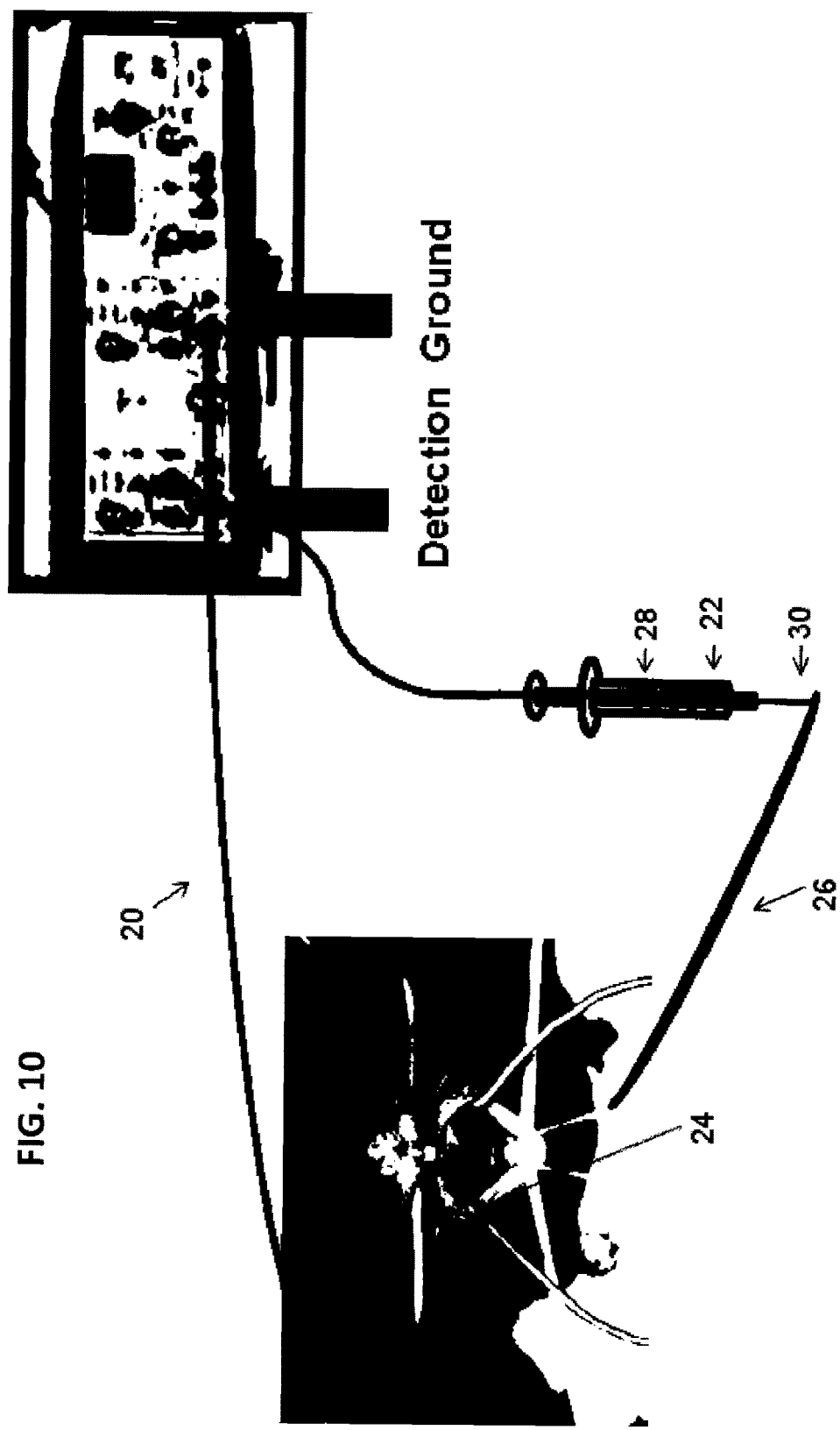
FIG. 10: Device for detection of SMG duct potential difference. To measure trans epithelial electric resistance (TEER) of the salivary gland, the electrode of a transmeter (model FD223, World Precision Instrument, Sarasota, Fla.) was cannulated in the SMG ducts of mice. The detecting electrode was placed in a 1 mL syringe and one end of the cannula was connected to the needle of the syringe. To make a circuit in the system, the syringe and cannula were filled with saline (0.09% sodium chloride, Aqualite System, Hospira, Lake Forest, Ill.). The other end of the cannula was inserted into the duct of the SMG by retrograde cannulation. The TEER was read by placing the ground electrode on the tissues adjacent to the opening of the duct. Background potential was determined by reading the potential when the detecting electrode was placed in saline only.

To measure electrophysiologic parameters associated with Sjögren's syndrome, a measurement circuit 20 (see FIG. 10) was established between a detection electrode 22 placed in a salivary gland duct and a reference electrode 24 placed in electrical contact with adjacent oral mucosa. In this particular example, the electrical potential was measured across the ducts of SMGs. A procedure was developed to measure TEER by cannulating the electrode of a transmeter (model FD223, World Precision Instrument, Sarasota, Fla.) in the ducts of SMGs of mice (FIG. 10). St14$^{LoxP/LoxP}$ mice were transduced with AAV2-Cre or AAV2-LacZ. Mice with pierced ducts served as controls. Twenty-two weeks post vector administration, mice were anesthetized as described in Example 1.

The detecting electrode included a cannula 26 placed on a 1 mL syringe 28, which was a fixed supporter. One end of the cannula 26 was then connected to the needle 30 of the syringe. To establish a circuit in the system, the syringe 28 and the cannula 26 were filled with saline (0.09% sodium chloride, Aqualite System, Hospira, Lake Forest, Ill.). The other end of cannula 26 was inserted in the duct of SMGs by retrograde cannulation as described above in Example 1. The trans-epithelial potential was read by placing the ground electrode on the tissues adjacent to the opening of the ducts. Background potential was determined by reading the potential when the detecting electronic rode was placed in saline only.

As shown in FIG. 11A, control mice and St14$^{LoxP/LoxP}$ mice expressing Cre exhibited a significantly lower electrical potential, as compared with St14$^{LoxP/LoxP}$ mice expressing LacZ. Salivary flow rate was evaluated in the mice and the results demonstrated that transmembrane epithelial electrical potential correlated with salivary gland activity (FIG. 11B).

To evaluate the effect of BMP6 overexpression in the SMG of mice, mice were transduced with AAV5 expressing either GFP or BMP6. Mice with pierced ducts served as controls. The results demonstrated that overexpression of BMP6 resulted in a significant increase in electrical potential compared with GFP controls (FIG. 7B). As expected, electrical resistance in control mice with pierced ducts was below the level of detection.

These findings demonstrate that an increase in BMP6 expression in the salivary gland (which occurs in the salivary gland of Sjögren's syndrome patients, as described in Example 1) results in an increase in electrical potential. Thus, an increase in electrical potential in the salivary gland can be used as a means for diagnosis of Sjögren's syndrome, to assess severity of disease, relative worsening of disease, or improvement in response to therapy. Relative increases in trans epithelial potential in a particular subject over time indicates worsening of disease, whereas relative decreases in trans epithelial potential in a particular subject over time indicate improvement of disease.

The present method and device for measuring electrophysiologic changes in the measurement circuit therefore provides a calibrated, objective measurement for detecting disease, determining its severity, and assessing its progress and/or response to therapy. The disclosed device and method therefore provide a needed objective test for a disease that otherwise relies on more subjective assessments, such as dry mouth and dry eyes.

Example 3

Diagnosis of Sjögren's Syndrome by Detecting BMP6 Expression in the Salivary Gland This example describes a method of diagnosing Sjögren's syndrome in a subject by measuring BMP6 levels in the salivary gland. In some examples, such diagnosis is performed before treating the subject. In some examples, the method is used to confirm a diagnosis of Sjögren's syndrome and/or is used in combination with other diagnostic measures.

A biological sample is obtained from the subject. If a tissue biopsy sample is used, about 1-100 μg of tissue is obtained, for example using a fine needle aspirate. Protein and RNA can be isolated from the tissue using routine methods (for example using a commercial kit). If saliva, tears, blood or a fraction thereof (such as serum), is used, about 1-1000 μl is collected. Saliva, tears, or serum can either be used directly or fractionated using filter cut-offs to remove high molecular weight proteins. If desired, the saliva, tears, or serum can be frozen and thawed before use.

In one example, the diagnosis of Sjögren's syndrome is determined by detecting BMP6 nucleic acid expression levels in a sample obtained from a subject (such as a salivary gland biopsy), such as by microarray analysis or RT-PCR. In another example, the diagnosis of Sjögren's syndrome is determined by detecting BMP6 protein expression levels in a sample (such as a tissue, blood or serum sample) obtained from a subject, such as by protein microarray, Western blot, or immunoassay (such as ELISA) techniques.

The relative amount of gene expression is compared to a reference or control value, such as a sample from a subject that is not clinically diagnosed with Sjögren's syndrome after an appropriate examination. An increase in expression of BMP6 as compared to the control sample (such as an increase of at least 2-fold, at least 3-fold, at least 4-fold or at least 5-fold) indicates that the subject has Sjögren's syndrome, or is at risk for developing Sjögren's syndrome.

Example 4

Diagnosis of Sjögren's Syndrome by Measuring Electrophysiologic Tissue Characteristics of the Salivary Gland This example describes a particular method of measuring electrophysiologic characteristics of the salivary gland tissue in Sjögren's syndrome patients. The disclosed measurement circuit can be used, for example, to measure tissue impedance or electrical potential in the salivary gland of a subject for the diagnosis of Sjögren's syndrome in a subject. In some examples, such diagnosis is performed before treating the subject. In some examples, the method is used to confirm a diagnosis of Sjögren's syndrome and/or is used in combination with other diagnostic measures. In other examples, the method is used over time to assess disease progression or its response to therapy. Therapeutic response can also be used to guide selection of treatment suitable or optimal for a particular patient.

In one example, the diagnosis of Sjögren's syndrome is determined by measuring electrical potential in a measurement circuit established in a salivary gland of a subject, such as the submandibular gland (SMG) or the parotid gland. The method of measuring electrical potential can include using a device for measuring electrical potential, such as a device that includes a voltmeter, a detection electrode and a reference electrode, wherein the detection electrode comprises a cannula having a tip of a diameter suitable for insertion into the duct of a salivary gland, the reference electrode is suitable for attachment to tissue external and adjacent to the duct of the salivary gland, and the detection and reference electrodes establish a conductive pathway for an electrical measurement current. The device is used, for example, to measure a voltage difference or tissue impedance between the detection and reference electrodes.

The reference and detection electrodes are generally placed approximately 0.3 to 0.5 cm apart. Any subsequent electrophysiologic measurements made in the patient (or any control values) should be made using substantially similar distances (such as within 0.5, 0.3 or 0.1 cm of the original separation distance) between the reference and detection electrodes to ensure consistent readings.

If the electrical measurement circuit is in a SMG, the detection electrode can be inserted into Wharton's duct; in a parotid gland, the detection electrode can be inserted into Stensen's duct.

A relative increase in electrical potential or tissue impedance in the measurement circuit of the subject compared to a reference or control value (such as a sample from a subject that is not clinically diagnosed with Sjögren's syndrome after an appropriate examination) indicates the subject has Sjögren's syndrome. In some examples, the increase in electrical potential or tissue impedance is about 10%, about 20%, about 30%, about 40%, about 50%, about 60%, about 70%, about 90%, about 80% or about 100%. In other examples, the increase in electrical potential or tissue impedance is about 1 or about 2 standard deviations beyond the mean electrical potential or tissue impedance of healthy control subjects.

Example 5

Treatment of Sjögren's Syndrome

This example describes a particular method that can be used to treat Sjögren's syndrome by administration of one or more agents that inhibit expression or activity of BMP6. Although particular methods, dosages, and modes of administrations are provided, one skilled in the art will appreciate that variations can be made without substantially affecting the treatment. A subject with Sjögren's syndrome can be treated by administering a therapeutically effective amount of a composition, wherein the composition comprises an agent (such as a specific binding agent) that reduces or eliminates the activity or expression of BMP6. The effectiveness of treatment can be evaluated, for example, by performing repeated electrophysiologic measurements to detect changes in electrical potential or tissue impedance, as described in Example 4. A relative decrease in electrical potential or tissue impedance in the measurement circuit of the subject after treatment indicates the therapy is effective.

Screening Subjects

In some examples, the subject is first screened using non-invasive methods (such as measuring tear production or salivary flow) to determine if the subject has symptoms characteristic of Sjögren's syndrome. In other examples, the subject is screened by detecting a change in the level of BMP6 in a sample (such as a salivary gland biopsy sample) obtained from the subject, relative to a control subject. In further examples, the subject is screened using a histopathological test to determine if the severity of the Sjögren's syndrome is categorized (using a Tarpley score) as "less severe" or "focal/negligible disease" (Tarpley score of $\leq 2$), or "advanced lesions" or "severe/diffuse disease" (Tarpley score of $TS=2^+-4$).

In some examples, the biological sample (e.g., tissue biopsy, tears, saliva, or serum) is analyzed to determine if BMP6 expression is increased relative to the control, wherein the presence of such increased expression indicates that the subject can be treated with the disclosed therapies. In one specific example, a biopsy of salivary gland tissue is obtained from the subject. RNA is isolated and purified from these cells using routine methods, such as using a commercial kit (e.g., an RNeasy Micro Kit according to the manufacturer's protocol; Qiagen; Valencia, Calif.). The purified RNA is then amplified and quantified, such as by RT-PCR or microarray analysis. The increased expression (such as an increase of at least 2-fold, at least 3-fold, or at 4-fold) of BMP6, relative to a control is indicative that the subject has Sjögren's syndrome and is a candidate for receiving the therapeutic compositions disclosed herein. However, such pre-screening is not required prior to administration of the therapeutic compositions disclosed herein.

Administration of Therapeutic Compositions

Following subject selection, a therapeutic effective dose of the composition including the agent is administered to the subject. For example, a therapeutic effective dose of an agent that inhibits expression or activity of BMP6 is administered to the subject to reduce or inhibit one or more signs or symptoms of Sjögren's syndrome. Administration can be achieved by any method known in the art, such as oral administration, inhalation, or inoculation (such as injection into the salivary gland, intramuscular, i.p., or subcutaneous). In some examples, the agent is an RNA aptamer specific for BMP6, a U7 RNA that induces exon skipping of BMP6 (to produce a dominant negative form of the protein), or a vector that encodes a BMP6-specific single chain antibody or that encodes a soluble form of the BMP6 receptor.

Assessment

Following the administration of one or more therapies, subjects having Sjögren's syndrome can be monitored to evaluate the effectiveness of the treatment, such as by evaluating a regression or reduction in symptoms, such as reduction in dry eyes and/or dry mouth. In particular examples, subjects are analyzed one or more times, such as starting 7 days following treatment. Subjects can be monitored using any method known in the art. For example, diagnostic imaging can be used (such as x-rays, CT scans, MRIs, ultrasound, fiber optic examination, and laparoscopic examination), as well as analysis of biological samples from the subject (for example analysis of saliva, tears, blood, tissue biopsy, or other biological samples), or by subjective measures. Subjects can also be monitored using electrophysiologic measurements in a measurement circuit to detect changes in electrical potential or tissue impedance, as described above.

Example 6

Gene Expression Changes in Male Sjögren's Syndrome Patients

This example describes the finding that XIST, a non-coding RNA that is not usually expressed in males, is expressed by male Sjögren's syndrome patients. In addition, the example describes data demonstrating that MECP2 is down-regulated in Sjögren's syndrome patients compared with healthy control subjects.

Figure 12A:
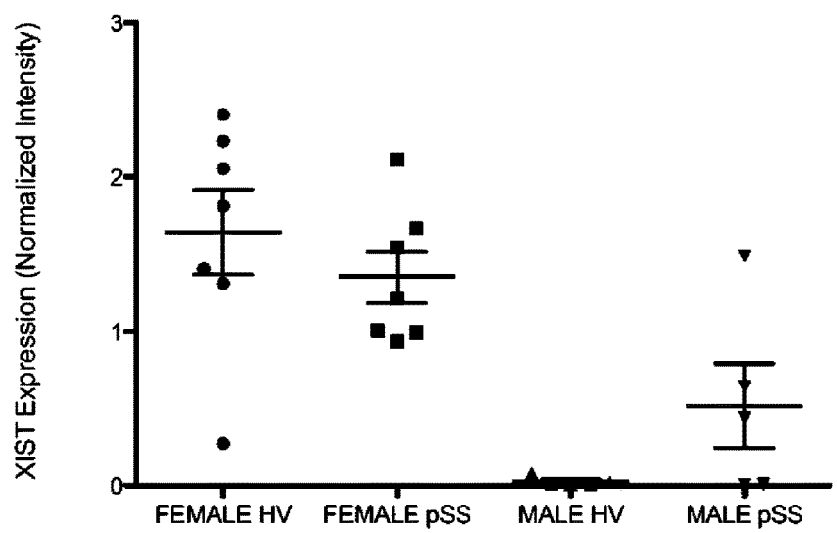
FIGS. 12A-12B: XIST expression identified in minor salivary glands of male Sjögren's syndrome patients. X (inactive)-specific transcript (non-protein coding) (XIST) expression was detected by microarray (FIG. 12A) and RT-PCR (FIG. 12B) in RNA isolated from minor salivary gland tissue obtained from male Sjögren's syndrome (SS) patients. HV=healthy volunteer; pSS=primary Sjögren's syndrome.
Figure 12B:
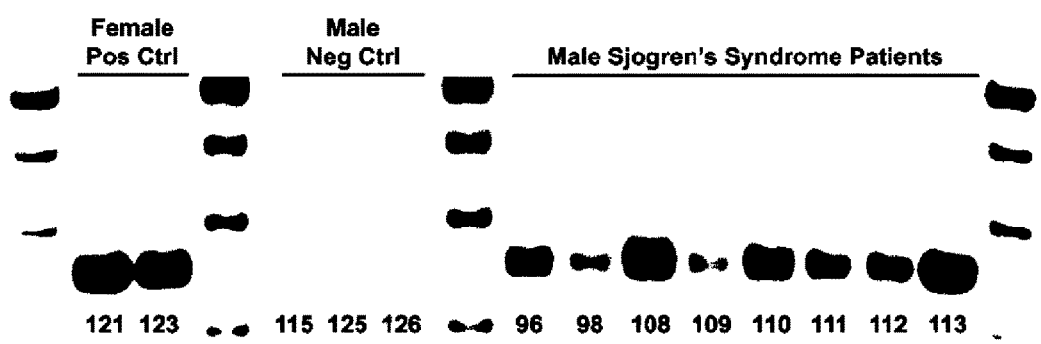

To evaluate gene expression changes in male Sjögren's syndrome patients, microarray analysis was performed. Microarray analysis of RNA obtained from minor salivary gland tissue revealed that male Sjögren's syndrome patients express XIST, a large non-coding RNA normally only expressed in the presence of 2 or more X-chromosomes, while male controls do not express this gene (FIG. 12A). These results were confirmed by RT-PCR (FIG. 12B).

Next, custom X-chromosome comparative genomic hybridization (CGH) array was used to identify copy number variants (CNV) present in the X-chromosome of male Sjögren's syndrome patients. Duplication and deletions were identified within X-chromosome regions spanning 151,680,000-153,420,000 nt (smallest region: 153,070,000-153,170,000) and 134,580,000-134,800,000 nt (smallest region: 134,670,000-134,800,000) in fragments or entirety. Mutations within these regions, including duplications, deletions or a combination of duplication and deletion, may impact gene expression profiled as suggested by microarray analysis.

Figure 13:
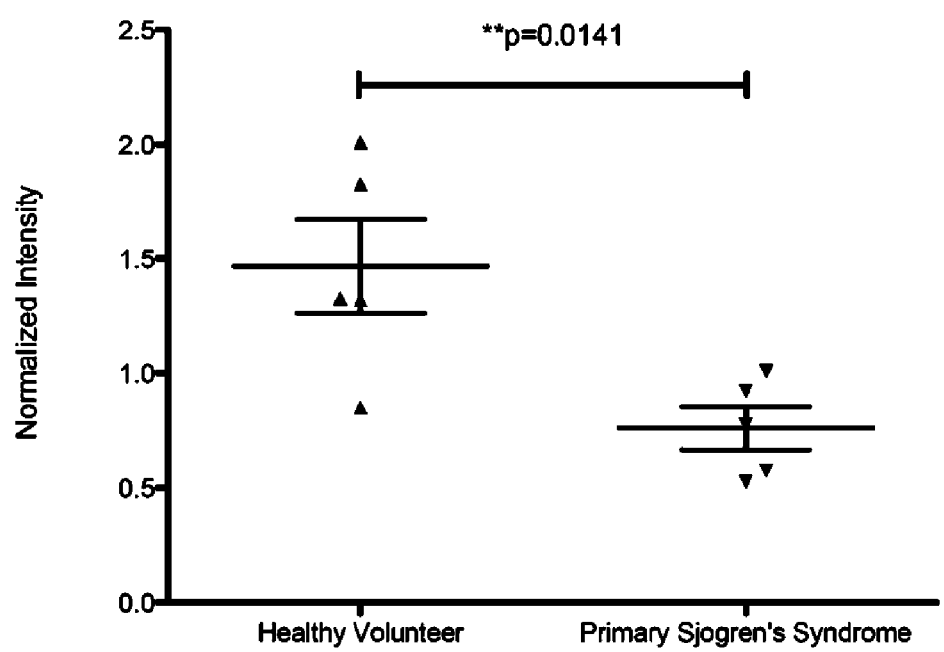
FIG. 13: Gene expression profile is disrupted in genes proximal to regions of X-chromosome containing identified duplication and/or deletions. Microarray analysis was used to measure gene expression profiles in primary Sjögren's syndrome patients compared to tissue obtained from healthy volunteers. One region of the X-chromosome with identified mutations contains elements that regulate methyl CpG binding protein 2 (MECP2) expression. Microarray analysis revealed MECP2 expression is down-regulated in minor salivary glands of male Sjögren's syndrome patients.

Microarray analysis was used to measure gene expression profiles in primary Sjögren's syndrome patients compared to tissue obtained from healthy volunteers. The findings demonstrate that the gene expression profile is disrupted in genes proximal to regions of the X-chromosome containing the identified duplication and/or deletions. In particular, one region of the X-chromosome with mutations contains elements that regulate methyl CpG binding protein 2 (MECP2) expression. Microarray analysis revealed MECP2 expression is down-regulated in minor salivary glands of male Sjögren's syndrome patients compared with male healthy volunteers (FIG. 13). Disruptions in MECP2 expression alter methylation of DNA Inhibition of DNA methylation has been shown to initiate aberrant XIST expression. Thus, XIST expression in XY males may be caused by altered methylation of the XIST promoter.

These results demonstrate that XIST and MECP2 can be used as diagnostic markers to identify male subjects with Sjögren's syndrome. XIST and MECP2 may also be therapeutic targets for the treatment of Sjögren's syndrome.

Example 7

Altered Sex Chromosome Gene Expression in Males Diagnosed with Sjögren's Syndrome and Associated Diseases Males diagnosed with primary Sjögren's syndrome (pSS) present a unique population to evaluate the factors influencing susceptibility to development of this predominantly female autoimmune disease. By evaluating the males, the aim was to identify factors impacting male susceptibility and the common thread between males and females diagnosed with SS. Microarray analysis of gene expression in minor salivary gland tissue of SS male patients was compared to healthy male and female controls. Significant alterations in sex-chromosome gene expression were identified in male SS patients, including XIST expression, decreased MECP2 expression and apparent silencing of Y-chromosome gene expression. This gene expression pattern, called Autoimmune Xist Y-chromosome Inactivation Syndrome (AXYIS), was also identified in affected tissues from males diagnosed with autoimmune diseases associated with pSS, including rheumatoid arthritis, type II diabetes mellitus, systemic sclerosis and lymphoma. Together, sex chromosome gene expression and pathways regulated by viral replication presented as a link between male and female Sjögren's syndrome populations.

Introduction

The X-chromosome has been suspect in the development of autoimmune diseases that predominantly afflict females; however, the direct link between the X-chromosome and development of autoimmunity has yet to be defined. Studying the two X-chromosome system in females presents a unique challenge due to the inherent variability of the inactivation state of the second X-chromosome under disease conditions, muddying the water between cause and effect. Therefore to simplify the system, the outliers were studied: males diagnosed with a female-predominant autoimmune disease. In using this approach, the aim was to evaluate factors influencing the development of autoimmunity in males to not only identify factors that alter the susceptibility of these males that develop a female-predominant autoimmune disease but to also identify the common thread between these atypical males and the larger female cohort.

Sjögren's syndrome (SS) is a perfect example of an autoimmune disease that predominantly afflicts females, with a female to male ratio of 9:1. Internationally, SS impacts approximately 0.6% of the population, or over 40 million people world-wide (Fox, *Annals of the New York Academy of Sciences* 1098:15-21, 2007; Helmick et al., *Arthritis and Rheumatism* 58:15-25, 2008). This autoimmune disease is primarily characterized by restricted saliva and tear production, lymphocytic infiltration of exocrine glands and development of autoantibodies. Patients are most commonly diagnosed in the 5th decade of life with a subset of patients being diagnosed earlier in their twenties and thirties (Ramos-Casals et al., *Lupus* 7:202-206, 1998). A limited number of studies have specifically evaluated clinical parameters of males diagnosed with Sjögren's syndrome (Anaya et al., *Annals of the Rheumatic Diseases* 54:748-751, 1995; Brennan and Fox, *The Journal of Rheumatology* 26:2373-2376, 1999; Drosos et al., *Annals of the Rheumatic Diseases* 56:333-335, 1997; Gondran et al., *Scandinavian Journal of Rheumatology* 37:300-305, 2008; Molina et al., *The American Journal of Medicine* 80:23-31, 1986). Males were noted to present similar clinical and immunological characteristics as females diagnosed with Sjögren's syndrome, with the exception of lower SSA autoantibody frequency in males. Overall, the prior studies of males diagnosed with Sjögren's syndrome suggest a similar pathway in phenotypic disease development and presentation between males and female.

The copy number of the X-chromosome has been associated with an increased risk of development of female-dominated autoimmune disease, including Sjögren's syndrome and lupus. Females with triple X syndrome (47,XXX) and males with Klinefelter's syndrome (47,XXY) have an increased risk of development of autoimmune diseases with a high female to male ratio, including Sjögren's syndrome, systemic lupus erythematosus, and autoimmune thyroiditis (Scofield et al., *Arthritis and Rheumatism* 58:2511-7251, 2008; Goswami et al., *Fertility and Sterility* 80:1052-1054, 2003). Recent studies have identified 0.3% of the female Sjögren's syndrome patient population and 2.5% of male and females diagnosed with systemic lupus erythematosus possess an X-chromosome aneuploidy (Dillon et al., *Arthritis and Rheumatism* 63:S251-S251, 2011; Dillon et al., *Journal of Autoimmunity* 38:J129-J134, 2012). Inversely, females with Turner syndrome (45,X) have a similar autoimmune risk profile as the XY,46 male population (Jorgensen et al., *Arthritis and Rheumatism* 62:658-666, 201). While these studies have suggested a link between X-chromosome copy number and an increased risk of development of female predominant autoimmunity, the simple presence of 2 or more X-chromosome in females or males does not equate to development of autoimmunity. Therefore, it must be assumed that other factors beyond X-chromosome copy number and associated cellular environment are triggering the development of autoimmunity. This current study was outlined to enable better understanding of the factors present in the female cellular environment that appear to favor development of autoimmunity and the connection shared with males diagnosed with predominantly female autoimmune diseases.

To further define the common thread between males and females diagnosed with Sjögren's syndrome, expression profiles were evaluated by microarray analysis of affected salivary gland tissue from SS male and female cohorts and compared to healthy male and female salivary gland tissue. This analysis revealed a subset of males with altered sex chromosome gene expression, including detection of XIST, decreased MECP2 expression and silencing of Y-chromosome gene expression in a subset of SS males. Expanding beyond Sjögren's syndrome, data-mining experiments identified this male SS profile, Autoimmune Xist Y-chromosome Inactivation Syndrome/Simplex (AXYIS), in subsets of males diagnosed with SS-associated diseases, including rheumatoid arthritis, type II diabetes and lymphoma. Together this data suggests a subset of males diagnosed with Sjögren's syndrome and associated diseases possess altered sex-chromosome gene expression that shifts the cellular environment of the affected tissue to a more female-like state, thereby altering susceptibility to development of female predominant autoimmunity.

Results

Males with SjöGren's Syndrome Cluster with Females in Sex-based Differential Gene Expression in Minor Salivary Gland Tissue Microarray analysis was performed using RNA isolated from minor salivary gland tissue from male and female healthy controls and males diagnosed with primary Sjögren's syndrome. Sex-based differential gene expression was performed to identify genes that are differentially expressed between healthy males and healthy females. Cluster analysis was then performed using the sex-based differential gene list between healthy males and females and males diagnosed with primary Sjögren's syndrome. This cluster analysis revealed a gene expression profile across the male Sjögren's syndrome patient population that was more similar to females than to their healthy male counterparts. Sex-based differential gene expression significantly correlated between healthy females and male pSS (Pearson Correlation Coefficient 0.96 $R^2$), with a 100% match on fold-change directionality. The cluster analysis was heavily weighted by the sex-chromosome gene expression.

XIST RNA was Detected in Salivary Gland Tissue of pSS Males

XIST is a large non-coding RNA thought to be expressed in the presence of 2 or more X-chromosomes and is utilized in dosage compensation. Males express XIST in the testes during spermatogenesis and limited expression has been reported in cardiac tissue. Males (XY,46) are not known to express XIST in the salivary gland. Using a probe targeting exon 6, three out of the five male samples showed high levels of XIST expression in minor salivary gland tissue. Subsequent PCR confirmation of XIST in minor salivary gland confirmed the presence of XIST in all males tested with primers targeting exon 1, 2, 3, 4 and 5 of XIST. The only deviation in the male Sjögren's syndrome patient population was the presence or absence of XIST in exon 6.

A Significant Down-Regulation of Y-chromosome Genes Expressed in Minor Salivary Gland Tissue was Observed in the Subset of pSS Males with Strong XIST Expression Genes that are expressed in the salivary gland of healthy male controls, including RPS4Y1, RPS4Y2, JARID1D, CYORF15B, and CYORF14 among others, were all down-regulated in the male pSS population that had high levels of XIST (exon 6) expression. In males that did not express XIST (exon 6), Y-chromosome gene expression was similar to that of healthy males. Fluorescent in situ hybridization was used to evaluate copy number of X- and Y-chromosome in paraffin-embedded salivary gland tissue. An experiment confirmed the presence of both X- and Y-chromosome in minor salivary gland of male pSS. This data confirms the presence of Y-chromosome in the salivary gland tissue of male pSS and suggests silencing of Y-chromosome gene expression in males that express XIST (exon 6).

Figure 15:
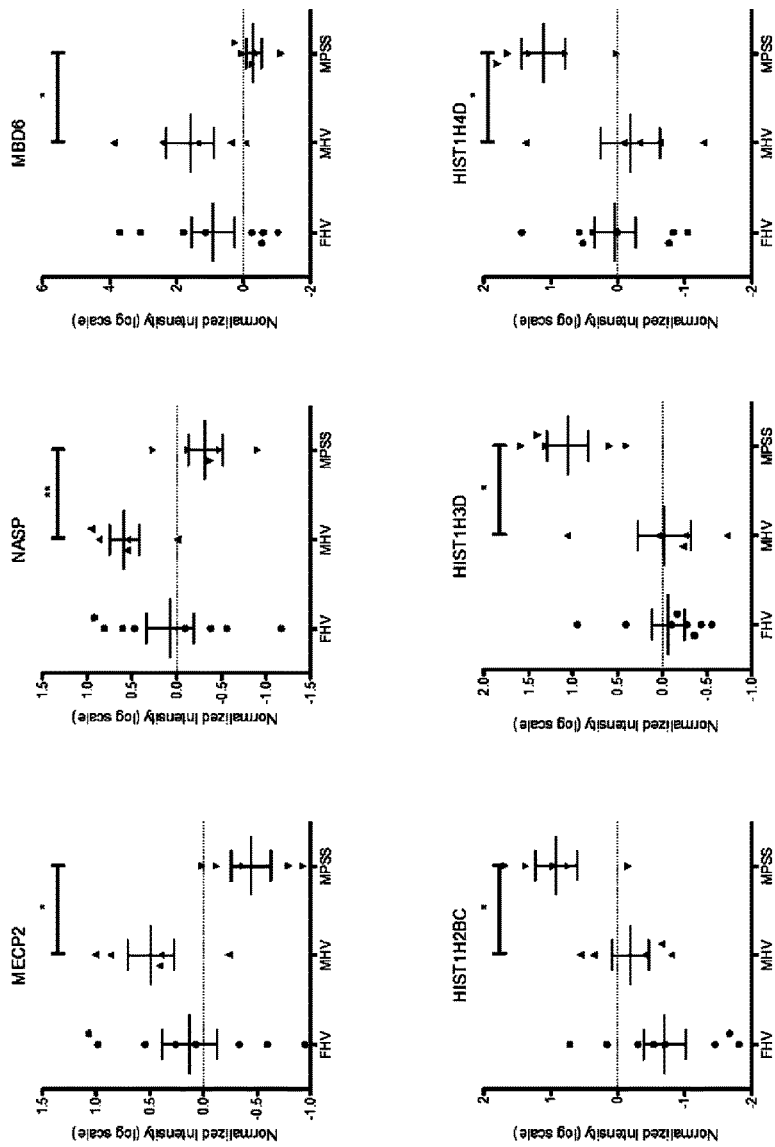
FIG. 15: Genes differentially expressed between males with pSS and healthy males. The graphs show that MECP2, NASP, MBD6, HIST1H2BC, HIST1H3D and HIST1H4D are differentially expressed between male healthy volunteers (MHV) and male patients with primary Sjögren's syndrome. Expression of these genes was also evaluated in female healthy volunteers (FHV).

Pathways Regulating RNA Processing, Viral Replication and Protein Localization are Altered in Males with Sjögren's Syndrome Differential gene expression between healthy male controls and males diagnosed with primary Sjögren's syndrome revealed significant downregulation in MECP2 in pSS males (FIG. 15). MECP2 is known to bind methylated DNA to regulate gene expression through maintenance of DNA methylation state. MECP2 is known to regulate expression of several genes including miR-212 and miR-132 and BDNF (Feng et al., *Nature Neuroscience* 13:1039-1041, 2010). Beyond MECP2, other proteins regulating DNA methylation, including MDB6 and NASP, were significantly down-regulated (FIG. 15). MBD1 was upregulated in male pSS and correlates with expression in the presence of MECP2 knockdown.

Expression of ribosomal proteins that are known to regulate RNA processing and viral replication was significantly down-regulated in pSS males. RPS4X, RPS4Y1, and RPS4Y2 were all significantly down-regulated in pSS males and showed a more similar expression pattern to healthy females than to healthy males.

Mosaic Level, Regional Amplifications and Deletions were Detected in X-chromosome of Male pSS Compared to Healthy Males A custom X-chromosome comparative genomic hybridization array was used to evaluate whole or partial X-chromosome copy number variants in the male Sjögren's syndrome patient population compared to healthy male control DNA. As detailed in FIG. 16, a significant number of mosaic-level duplications and/or deletions were observed in the opsin (OPN1LW, OPN1MW, OPN1MW2) and tex28 region in the X-chromosome of male pSS. This region is known to possess CNV in a reported 10-40% of samples tested. Mosaic-level mutations were observed in several of the male pSS population. Sequencing of the region spanning the deletion confirmed the presence of mosaic level deletions in the opsin region of the X-chromosome. Interestingly, the CNV initiation sites in the opsin region are just upstream of the MECP2 promoter.

Figure 17:
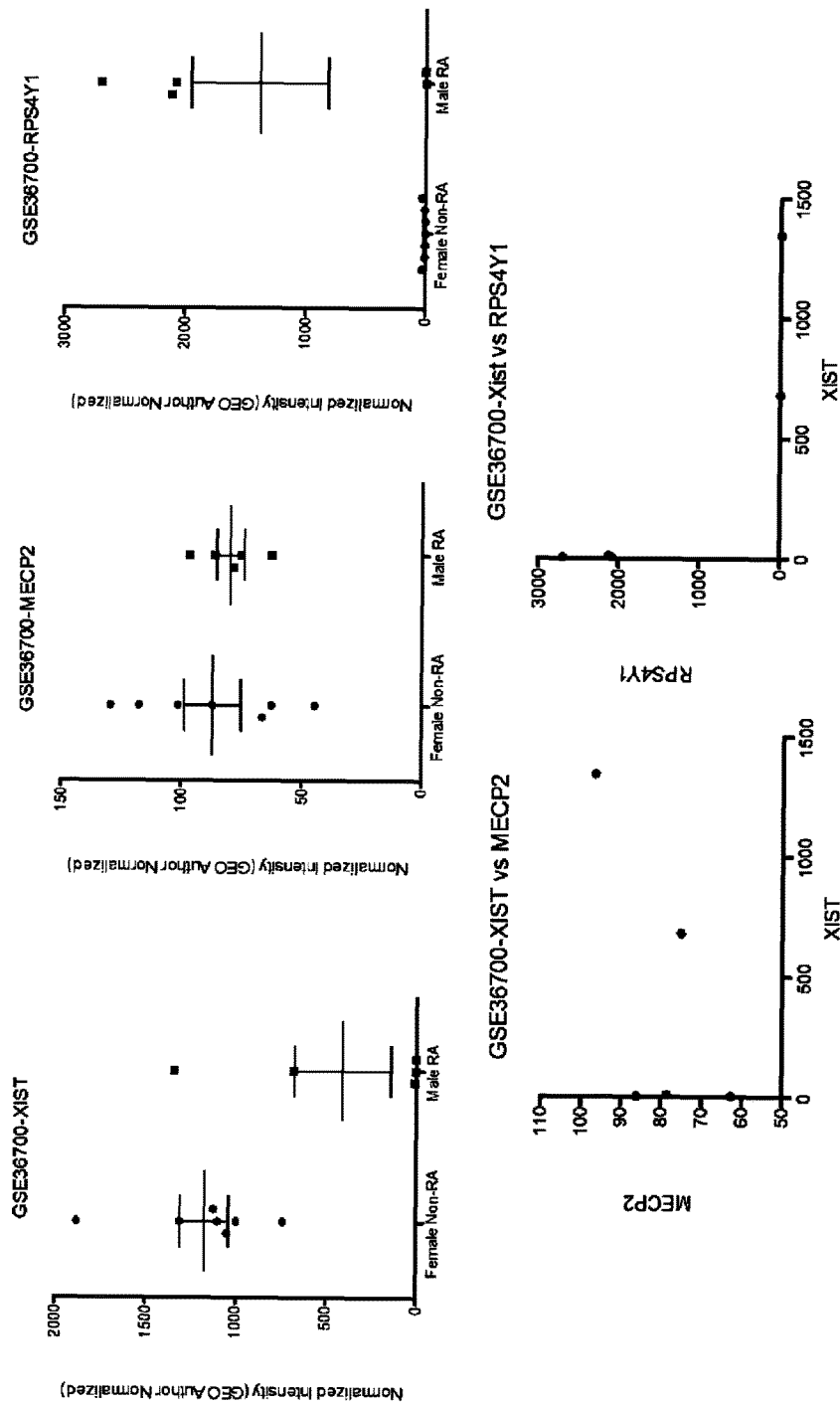
FIG. 17: Gene expression profiles of male patients with rheumatoid arthritis (RA). Expression of XIST, RPS4Y1 and MECP2 in male and female patients with RA is shown in the upper graphs. A comparison of XIST and MECP2, as well as XIST and RPS4Y1, expression in male patients is shown in the lower graphs.

Evidence of XIST Expression and Silencing or Loss of Y-chromosome Gene Expression Present in Males Diagnosed with Associated Diseases, Including Rheumatoid Arthritis, Type II Diabetes and Lymphoma Multiple diseases are associated with Sjögren's syndrome, including systemic lupus erythematosus (SLE), rheumatoid arthritis, fibromyalgia, autoimmune thyroiditis, and primary systemic sclerosis. Data-mining of publically available gene expression datasets were used to evaluate the presence of AXYIS in males diagnosed with autoimmune diseases associated with SS. Studies of rheumatoid arthritis (RA) gene expression in blood and synovial membrane identified samples possessing gene expression profiles similar to the AXYIS pSS males. As noted in FIG. 17, a subset of male RA samples had detectable levels of XIST that correlated (PCC) with the drop in Y-chromosome gene expression. No significant correlation was noted between XIST and MECP2. Evaluation of Y-chromosome genes present on the microarray platforms used showed a consistent negative correlation between XIST and a majority of Y-chromosome genes evaluated. Therefore, RPS4Y1 or KDM5D (JARID1D) will be used in representation of AXYIS correlations.

Figure 18:
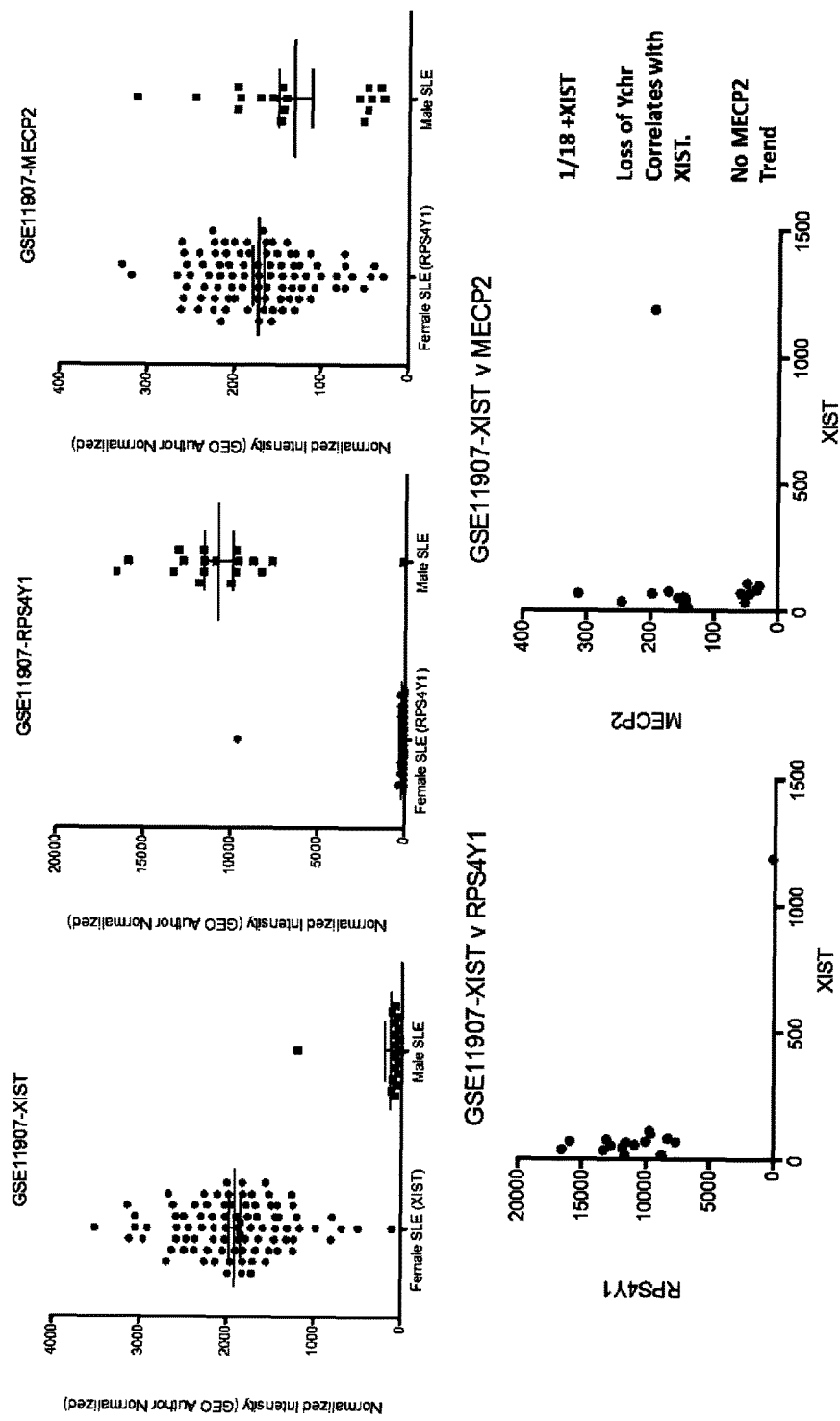
FIG. 18: Gene expression profiles of male patients with systemic lupus erythematosus (SLE). Expression of XIST, RPS4Y1 and MECP2 in male and female patients with SLE is shown. A comparison of XIST and MECP2, as well as XIST and RPS4Y1, expression in male patients is shown in the lower graphs.

Expression profiles were evaluated for systemic lupus erythematosus (SLE) blood and affected skin biopsy. As detailed in FIG. 18, gene expression in blood revealed 5.5% (1/18) of male SLE samples possessing the AXYIS gene expression profile. Dermal tissue and synovial tissue obtained from active and inactive SLE patients contained males that had significant increase in XIST expression and correlated decreased in Y-chromosome gene expression.

In addition to autoimmune diseases, studies evaluating gene expression from healthy male and female controls, and individuals diagnosed with cardiovascular disease (CVD), were also assessed for background presence of AXYIS. Control studies did not present evidence of XIST gene expression in male controls or in males with CVD.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method, comprising:
   obtaining a biological sample from a human or mouse subject who has symptoms of dry eyes and/or dry mouth, wherein the biological sample is a salivary gland sample, a saliva sample or a serum sample;
   detecting expression of bone morphogenic protein 6 (BMP6) in the biological sample of the human or mouse subject;
   diagnosing the subject as having Sjögren's syndrome by (i) detecting at least a 2-fold increase in expression of BMP6 in the biological sample of the human or mouse subject relative to expression of BMP6 in a corresponding biological sample from a healthy control human or mouse subject, respectively, who does not have Sjögren's syndrome, and (ii) detecting the presence of autoantibodies to Ro (SSA) or La (SSB) antigens in the serum of the human or mouse subject; and
   treating Sjögren's syndrome in the subject by administering a therapeutically effective amount of a corticosteroid to the subject.

2. The method of claim 1, wherein the salivary gland sample is a minor labial salivary gland, parotid gland or a submandibular gland.

3. The method of claim 1, wherein the increase is at least 3-fold or at least 4-fold relative to the healthy control human or mouse subject.

4. The method of claim 1, wherein the biolgical sample is a salivary gland sample and detecting expression of BMP6 in the salivary gland sample comprises measuring the level of BMP6 mRNA in the salivary gland sample.

5. The method of claim 1, wherein detecting expression of BMP6 in the biological sample comprises measuring the level of BMP6 protein in the biological sample.

6. The method of claim 1, wherein the corticosteroid is cortisol or prednisone.

7. The method of claim 4, wherein the level of BMP6 mRNA in the salivary gland sample is measured using RT-PCR.

8. The method of claim 5, wherein the level of BMP6 protein in the salivary gland sample is measured using an immunoassay.

9. The method of claim 8, wherein the immunoassay is an enzyme-linked immunosorbent assay (ELISA), an immunohistochemistry (IHC) assay, or a Western blot.

10. The method of claim 1, wherein the subject is a human.

11. The method of claim 1, wherein the subject is a mouse.

12. The method of claim 1, wherein the biological sample is a salivary gland sample.

13. The method of claim 1, wherein the biological sample is a saliva sample.

14. The method of claim 1, wherein the biological sample is a serum sample.

* * * * *